(12) United States Patent
Simpson et al.

(10) Patent No.: US 9,732,329 B2
(45) Date of Patent: *Aug. 15, 2017

(54) CELLS GENETICALLY MODIFIED TO COMPRISE PANCREATIC ISLET GLUCOKINASE AND USES THEREOF

(71) Applicant: University of Technology, Sydney, Broadway (AU)

(72) Inventors: Ann Margaret Simpson, Killarney Heights (AU); Chang Tao, Westmead (AU)

(73) Assignee: University of Technology, Sydney, Broadway (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/053,992

(22) Filed: Feb. 25, 2016

(65) Prior Publication Data

US 2016/0244733 A1  Aug. 25, 2016

Related U.S. Application Data

(63) Continuation of application No. 14/185,716, filed on Feb. 20, 2014, now Pat. No. 9,365,829, which is a continuation of application No. 12/672,832, filed as application No. PCT/AU2008/001160 on Aug. 8, 2008, now abandoned.

(30) Foreign Application Priority Data

Aug. 10, 2007 (AU) ................. 2007904310

(51) Int. Cl.
| | | |
|---|---|---|
| *C12N 5/071* | (2010.01) | |
| *A61K 35/407* | (2015.01) | |
| *A61K 38/45* | (2006.01) | |
| *C12N 9/12* | (2006.01) | |
| *A61K 38/28* | (2006.01) | |
| *C07K 14/62* | (2006.01) | |
| *C12N 15/85* | (2006.01) | |
| *A61K 35/12* | (2015.01) | |
| *A61K 48/00* | (2006.01) | |

(52) U.S. Cl.
CPC .......... *C12N 9/1205* (2013.01); *A61K 35/407* (2013.01); *A61K 38/28* (2013.01); *A61K 38/45* (2013.01); *C07K 14/62* (2013.01); *C12N 5/067* (2013.01); *C12N 15/85* (2013.01); *A61K 35/12* (2013.01); *A61K 48/00* (2013.01); *C12N 2501/33* (2013.01); *C12N 2510/00* (2013.01); *C12N 2830/20* (2013.01); *C12Y 207/01002* (2013.01)

(58) Field of Classification Search
CPC ...... A61K 35/12; A61K 35/407; A61K 38/28; A61K 38/45; A61K 48/00; C07K 14/62; C12N 15/85; C12N 2501/33; C12N 2510/00; C12N 2830/20; C12N 5/067; C12N 9/1205; C12Y 207/01002

USPC ................ 424/93.21; 435/325, 370
See application file for complete search history.

(56) References Cited

U.S. PATENT DOCUMENTS

| | | | |
|---|---|---|---|
| 5,427,940 A | 6/1995 | Newgard | |
| 5,427,950 A | 6/1995 | Shigematsu et al. | |
| 9,365,829 B2* | 6/2016 | Simpson ................ | C12N 5/067 |
| 2002/0104110 A1 | 8/2002 | Lipes et al. | |

FOREIGN PATENT DOCUMENTS

| | | |
|---|---|---|
| WO | WO 95/32740 A1 | 12/1995 |
| WO | WO 00/62862 A1 | 10/2000 |
| WO | WO 02/092756 A2 | 11/2002 |
| WO | WO 2007/019646 A1 | 2/2007 |

OTHER PUBLICATIONS

Auricchio, A. et al., "Constitutive and regulated expression of processed insulin following in vivo hepatic gene transfer" Gene Therapy, 2002, pp. 963-971, vol. 9.

Bartlett, R.J. et al., "Toward Engineering Skeletal Muscle to Release Peptide Hormone From the Human Pre-Proinsulin Gene" Transplantation Proceedings, 1998, p. 451, vol. 30.

Beckman, Joshua A. et al., "Diabetes and Atherosclerosis, Epidemiology, Pathophysiolgy, and Management" JAMA, May 15, 2002, pp. 2570-2581, vol. 287, No. 19.

Ber, Idit et al., "Functional, Persistent, and Extended Liver to Pancreas Transdifferentiation" The Journal of Biological Chemistry, Aug. 22, 2003, pp. 31950-31957, vol. 278, No. 34.

Bochan, M.R. et al., "Stable Transduction of Human Pancreatic Adenocarcinoma Cells, Rat Fibroblasts, and Bone Marrow-Derived Stem Cells With Recombinant Adeno-Associated Virus Containing the Rat Preproinsulin II Gene" Transplantation Proceedings, 1998, pp. 453-454, vol. 30.

Cardozo, Alessandra K. et al., "A Comprehensive Analysis of Cytokine-induced and Nuclear Factor-κB-dependent Genes in Primary Rat Pancreatic β-Cells" The Journal of Biological Chemistry, 2001, pp. 48879-48886, vol. 276, No. 52.

(Continued)

*Primary Examiner* — Janet Epps-Smith
(74) *Attorney, Agent, or Firm* — Knobbe, Martens, Olson & Bear, LLP

(57) ABSTRACT

The present invention relates generally to a population of cells genetically modified to produce insulin in a glucose responsive manner and uses thereof. More particularly, the present invention relates to a population of cells genetically modified to produce insulin in response to physiologically relevant levels of glucose and uses thereof. The cells of the present invention are useful in a wide variety of applications, in particular in the context of therapeutic and prophylactic regimes directed to the treatment of diabetes and/or the amelioration of symptoms associated with diabetes, based on the transplantation of the cells of the present invention into mammals requiring treatment. Also facilitated is the design of in vitro based screening systems for testing the therapeutic effectiveness and/or toxicity of potential adjunctive treatment regimes.

4 Claims, 33 Drawing Sheets

(56) References Cited

OTHER PUBLICATIONS

Cheung, Anthony T. et al., "Glucose-Dependent Insulin Release from Genetically Engineered K Cells" Science, 2000, pp. 1959-1962, vol. 290.
Clark, Samuel A. et al., "Novel Insulinoma Cell Lines Produced by Iterative Engineering of GLUT2, Glucokinase, and Human Insulin Expression" Diabetes, Jun. 1997, pp. 958-967, vol. 46.
Efrat, Shimon "Regulation of Insulin Secretion Insights from Engineered β-cell Lines" Ann. N.Y. Acad. Sci. 2004, pp. 88-96, vol. 1014.
Falqui, Luca et al., "Reversal of Diabetes in Mice by Implantation of Human Fibroblasts Genetically Engineered to Release Mature Human Insulin" Human Gene Therapy, Jul. 20, 1999, pp. 1753-1762, vol. 10.
Falqui, Luca "Insulin-Secreting Cells for Diabetes" Human Gene Therapy, Jul. 20, 1999, pp. 1741-1742, vol. 10.
Ferber, Sarah et al., "Pancreatic and duodenal homeobox gene 1 induces expression of insulin genes in liver and ameliorates streptozotocin-induced hyperglycemia" Nature Medicine, May 2000, pp. 568-572, vol. 6, No. 5.
Hathout, E. et al., "Islet transplant: an option for childhood diabetes?" Arch Dis Child, 2003, pp. 591-594, vol. 88.
Heremans, Yves et al., "Recapitulation of embryonic neuroendocrine differentiation in adult human pancreatic duct cells expressing neurogenin 3" The Journal of Cell Biology, Oct. 28, 2002, pp. 303-311, vol. 159, No. 2.
Huang, Manley T.F. et al., "Intervening sequences increase efficiency of RNA 3' processing and accumulation of cytoplasmic RNA" Nucleic Acids Research, 1990, pp. 937-947, vol. 18, No. 4.
Hughes, Steven D. et al., "Engineering of glucose-stimulated insulin secretion and biosynthesis in non-islet cells" Proc. Natl. Acad. Sci. USA, Jan. 1992, pp. 688-692, vol. 89.
Hughes S D et al: "Expression of normal and novel glucokinase messenger RNAs in anterior pituitary and islet cells", Journal of Biological Chemistry, vol. 266, No. 7, 1991, pp. 4521-4530.
Imai, Junta et al., "Constitutively active PDX1 induced efficient insulin production in adult murine liver" Biochemical and Biophysical Research Communications, 2005, pp. 402-409, vol. 326.
Jackson, Richard J. et al., "The novel mechanism of initiation of picornavirus RNA translation" Trends in Biochemical Sciences, Dec. 1990, pp. 477-483, vol. 15, Issue 12—Abstract.
Jang, Sung K. et al., "A Segment of the 5' Nontranslated Region of Encephalomyocarditis Virus RNA Directs Internal Entry of Ribosomes during In Vitro Translation" Journal of Virology, Aug. 1988, pp. 2636-2643, vol. 62, No. 8.
Janssens, S. et al., "Signals from within: the DNA-damage-induced NF-κB response" Cell Death and Differentiation, 2006, pp. 773-784, vol. 13.
Kasten-Jolly, J. et al., "Reversal of Hyperglycemia in Diabetic NOD Mice by Human Proinsulin Gene Therapy" Transplantation Proceedings, 1997, pp. 2216-2218, vol. 29.
Kim, Jung Ju et al., "Modulated insulin delivery from glucose-sensitive hydrogel dosage forms" Journal of Controlled Release, 2001, pp. 39-47, vol. 77.
Kojima, Hideto et al., "NeroD-betacellulin gene therapy induces islet neogenesis in the liver and reverses diabetes in mice" Nature Medicine, May 2003, pp. 596-603, vol. 9, No. 5.
Kolodka, Tadeusz et al., "Gene therapy for diabetes mellitus in rats by hepatic expression of insulin" Proc. Natl. Acad. Sci. USA, Apr. 1995, pp. 3293-3297, vol. 92.
Kutlu, Burak et al., "Molecular Regulation of Monocyte Chemoattractant Protein-1 Expression in Pancreatic β-Cells" Diabetes, Feb. 2003, pp. 348-355, vol. 52.
Kuwajima, Masamichi et al., "The Glucose-phosphorylating Capacity of Liver as Measured by Three Independent Assays" The Journal of Biological Chemistry, Jul. 5, 1986, pp. 8849-8853, vol. 261, No. 19.
Levine, Fred et al., "Towards gene therapy of diabetes mellitus" Molecular Medicine Today, Apr. 1999, pp. 165-171, vol. 5.
Lipes, Myra A. et al., "Insulin-secreting non-islet cells are resistant to autoimmune destruction" Proc. Natl. Acad. Sci. USA, Aug. 1996, pp. 8595-8600, vol. 93.
Luna, Susana De La et al., "Efficient transformation of mammalian cells with constructs containing a puromycin-resistance marker" Gene, 1988, pp. 121-126, vol. 62.
Mandrup-Poulsen, Thomas "β-Cell Apoptosis—Stimuli and Signaling" Diabetes, Feb. 2001, pp. S58-S63, vol. 50, Supplement 1.
McAlister, Vivian C. et al., "Sirolimus-tacrolimus combination immunosuppression" The Lancet, Jan. 29, 2000, pp. 376-377, vol. 355.
Monges, G. et al., "Gastrointestinal hormone mRNA expression in human colonic adenocarcinomas, hepatic metastases and cell lines" J Clin Pathol:Mol Pathol, 1996, pp. M159-M165, vol. 49.
Nakayama, Maki et al., "Prime role for an insulin epitope in the development of type 1 diabetes in NOD mice" Nature, May 12, 2005, pp. 220-223, vol. 435.
Ortis, Fernanda et al., "Cytokine-Induced Proapoptotic Gene Expression in Insulin-Producing Cells is Related to Rapid, Sustained, and Nonoscillatory Nuclear Factor-κB Activation" Molecular Endocrinology, 2006, pp. 1867-1879, vol. 20, No. 8.
Permutt, M. Alan et al., "Cloning and functional expression of a human pancreatic islet glucose-transporter cDNA" Proc. Natl. Acad. Sci. USA, Nov. 1989, pp. 8688-8692, vol. 86.
Pinkse, Gabrielle G. M. et al., "Autoreactive CD8 T cells associated with β cell destruction in type 1 diabetes" PNAS, Dec. 20, 2005, pp. 18425-18430, vol. 102, No. 51.
Rees, S. et al., "Bicistronic Vector for the Creation of Stable Mammalian Cell Lines that Predisposes All Antibiotic-Resistant Cells to Express Recombinant Protein" BioTechniques, Jan. 1996, pp. 102-110, vol. 20.
Sapir, Tamar et al., "Cell-replacement therapy for diabetes: Generating functional insulin-producing tissue from adult human liver cells" PNAS, May 31, 2005, pp. 7964-7969, vol. 102, No. 22.
Seewaldt, Sonja et al., "Virus-Induced Autoimmune Diabetes—Most β-Cells Die Through Inflammatory Cytokines and Not Perforin From Autoreactive (Anti-viral) Cytotoxic T-Lymphocytes" Diabetes, Nov. 2000, pp. 1801-1809, vol. 49.
Selden, Richard F. et al., "Regulation of Insulin-Gene Expression—Implications for Gene Therapy" The New England Journal of Medicine, Oct. 22, 1987, pp. 1067-1076, vol. 317, No. 17.
Simpson, A.M. et al., "Transformation of Pituitary and Fibroblast Cell Lines Using Human Insulin c-DNA and a Dexamethasone-Inducible Promoter" Transplantation Proceedings, Oct. 1993, pp. 2915-2916, vol. 25, No. 5.
Tabiin, Muhammad T. et al., "Susceptibility of Insulin-secreting Hepatocytes to the Toxicity of Pro-inflammatory Cytokines" Journal of Autoimmunity, 2001, pp. 229-242, vol. 17.
Taniguchi, Hideki et al., "Constant Delivery of Proinsulin by Encapsulation of Transfected Cells" Journal of Surgical Research, 1997, pp. 41-45, vol. 70.
Thulé, PM et al., "Glucose regulated production of human insulin in rat hepatocytes" Gene Therapy, 2000, pp. 205-214, vol. 7.
Truong, Wayne et al., "Clinical Islet Transplantation at the University of Alberta—The Edmonton Experience" Clinical Transplants, 2005, pp. 153-172, Chapter 13.
Truong, Wayne et al., "Clinical Islet Transplantation at the University of Alberta—The Edmonton Experience" Clinical Transplants, 2005, pp. 153-172, Abstract.
Tuch, B.E. et al., "Function of a genetically modified human liver cell line that stores, processes and secretes insulin" Gene Therapy, 2003, pp. 490-503, vol. 10.
Verge, Charles F. et al., "Prediction of Type I Diabetes in First-Degree Relatives Using a Combination of Insulin, GAD, and ICA512bdc/IA-2 Autoantibodies" Diabetes, Jul. 1996, pp. 926-933, vol. 45.
Vermes, István et al., "A novel assay for apoptosis Flow cytometric detection of phosphatidylserine expression on early apoptotic cells using fluorescein labelled Annexin V" Journal of Immunological Methods, 1995, pp. 39-51, vol. 84.
Vollenweider, Florence et al., "Processing of Proinsulin by Transfected Hepatoma (FAO) Cells" The Journal of Biological Chemistry, Jul. 25, 1992, pp. 14629-14636, vol. 267, No. 21.

(56) References Cited

OTHER PUBLICATIONS

Westerman, Bart A. et al., "NEUROD1 acts in vitro as an upstream regulator of NEUROD2 in trophoblast cells" Biochimica et Biophysica Acta, 2004, pp. 96-103, vol. 1676.

Zalzman, Michal et al., "Reversal of hyperglycemia in mice by using human expandable insulin-producing cells differentiated from fetal liver progenitor cells" PNAS, Jun. 10, 2003, pp. 7253-7258, vol. 100, No. 12.

International Search Report for PCT/AU2008/001160 dated Sep. 30, 2008.

* cited by examiner

FIGURE 2

```
  1 gacggatcgg gagatctccc gatccccctat ggtcgactct cagtacaatc tgctctgatg
 61 ccgcatagtt aagccagtat ctgctccctg cttgtgtgtt ggaggtcgct gagtagtgcg
121 cgagcaaaat ttaagctaca acaaggcaag gcttgaccga caattgcatg aagaatctgc
181 ttagggttag gcgttttgcg ctgcttcgcg atgtacgggc cagatatacg cgttgacatt
241 gattattgac tagttattaa tagtaatcaa ttacggggtc attagttcat agcccatata
301 tggagttccg cgttacataa cttacggtaa atggcccgcc tggctgaccg cccaacgacc
361 cccgcccatt gacgtcaata atgacgtatg ttcccatagt aacgccaata gggactttcc
421 attgacgtca atgggtggac tatttacggt aaactgccca cttggcagta catcaagtgt
481 atcatatgcc aagtacgccc cctattgacg tcaatgacgg taaatggccc gcctggcatt
541 atgcccagta catgacctta tgggactttc ctacttggca gtacatctac gtattagtca
601 tcgctattac catggtgatg cggttttggc agtacatcaa tgggcgtgga tagcggtttg
661 actcacgggg atttccaagt ctccaccccca ttgacgtcaa tgggagtttg ttttggcacc
721 aaaatcaacg ggactttcca aaatgtcgta acaactccgc cccattgacg caaatgggcg
781 gtaggcgtgt acggtgggag gtctatataa gcagagctct ctggctaact agagaaccca
841 ctgcttactg gcttatcgaa attaatacga ctca *ctatag ggagacccaa gctggta cc* (24 base pair sequence primer)
901 gagctcggat cgatatctgc ggcctagcta gcgcttaagg ccgttaacc ggtcgtacgt
961 ctccggattcg
```

```
   1 cGAGCGGCGCCTGAGCCCCAGGGAAGCAGGCTAGGATGTGAGAGACACAGTCACCTGCA
  61 GCCTAATTACTCAAAAGCTGTCCCCAGGTCACAGAAGGGAGAGGACATTTCCCACTGAAT
 121 CTGTCTGAAGGACACTAAGCCCCACAGCTCAACACAACCAGGAGAGAAAGCGCTGAGGAC
 181 GCCACCCAAGCGCCCAGCAATGGCCCTGCCTGGAGAACATCCAGGCTCAGTGAGGAAGGG
 241 TCCAGAAGGGAATGCTTGCCGACTCGTTGGAGAACAATGAAAAGGAGGAAACTGTGACTG
 301 AACCTCAAACCCCAAACCAGCCCGAGGAGACACATTCTCCCAGGGACCCAGGGCCGGGC
 361 CGTGACCCCTGCGGCGGAGAAGCCTTGGATATTTCCACTTCAGAAGCCTACTGGGGAAGG
 421 CTGAGGGGTCCCAGCTCCCCACGCTGGCTGCTGTGCAGATGCTGGACGACAGAGCCAGGA
 481 TGGAGGCCGCCAAGAAGGAGAAGGTAGAGCAGATCCTGGCAGAGTTCCAGCTGCAGGAGG
 541 AGGACCTGAAGAAGGTGATGAGACGGATGCAGAAGGAGATGGACCGCGGCCTGAGGCTGG
 601 AGACCCATGAAGAGGCCAGTGTGAAGATGCTGCCCACCTACGTGCGCTCCACCCCAGAAG
 661 GCTCAGAAGTCGGGGACTTCCTCTCCCTGGACCTGGGTGGCACTAACTTCAGGGTGATGC
 721 TGGTGAAGGTGGGAGAAGGTGAGGAGGGGCAGTGGAGCGTGAAGACCAAACACCAGATGT
 781 ACTCCATCCCCGAGGACGCCATGACCGGCACTGCTGAGATGCTCTTCGACTACATCTCTG
 841 AGTGCATCTCCGACTTCCTGGACAAGCATCAGATGAAACACAAGAAGCTGCCCCTGGGCT
 901 TCACCTTCTCCTTTCCTGTGAGGCACGAAGCACATCGATAAGGGCATCCTTCTCAACTGA
 961 CCAAGGGCTTCAAGGCCTCAGGAGCAGAAGGGAACAATGTCGTGGGGCTTCTGCGAGACG
1021 CTATCAAACGGAGAGGGGACTTTGAAATGGATGTGGTGGCAATGGTGAATGACACGGTGG
1081 CCACGATGATCTCCTGCTACTACGAAGACCATCAGTGCGAGGTCGGCATGATCGTGGGCA
1141 CGGGCTGCAATGCCTGCTACATGGAGGAGATGCAGAATGTGGAGCTGGTGGAGGGGGACG
1201 AGGGCCGCATGTGCGTCAATACCGAGTGGGGCGCCTTCGGGGACTCCGGCGAGCTGGACG
1261 AGTTCCTGCTGGAGTATGACCGCCTGGTGGACGAGAGCTCTGCAAACCCCGGTCAGCAGC
1321 TGTATGAGAAGCTCATAGGTGGCAAGTACATGGGCGAGCTGGTGCGGCTTGTGCTGCTCA
1381 GGCTCGTGGACGAAAACCTGCTCTTCCACGGGGAGGCCTCCGAGCAGCTGCGCACACGCG
1441 GAGCCTTCGAGACGCGCTTCGTGTCGCAGGTGGAGAGCGACACGGGCGACCGCAAGCAGA
1501 TCTACAACATCCTGAGCACGCTGGGGCTGCGACCCTCGACCACCGACTGCGACATCGTGC
1561 GCCGCGCCTGCGAGAGCGTGTCTACGCGCGCTGCGCACATGTGCTCGGCGGGGCTGGCGG
1621 GCGTCATCAACCGCATGCGCGAGAGCCGCAGCGAGGACGTAATGCGCATCACTGTGGGCG
1681 TGGATGGCTCCGTGTACAAGCTGCACCCCAGCTTCAAGGAGCGGTTCCATGCCAGCGTGC
1741 GCAGGCTGACGCCCAGCTGCGAGATCACCTTCATCGAGTCGGAGGAGGGCAGTGGCCGGG
1801 GCGCGGCCCTGGTCTCGGCGGTGGCCTGTAAGAAGGCCTGTATGCTGGGCCAGTGAGAGC
1861 AGTGGCCGCAAGCGCAGGGAGGATGCCACAGCCCCACAGCACCCAGGCTCCATGGGGAAG
1921 TGCTCCCCACACGTGCTCGCAGCCTGGCGGGGCAGGAGGCCTGGCCTTGTCAGGACCCAG
1981 GCCGCCTGCCATACCGCTGGGGAACAGAGCGGGCCTCTTCCCTCAGTTTTTCGGTGGGAC
2041 AGCCCCAGGGCCCTAACGGGGGTGCGGCAGGAGCAGGAACAGAGACTCTGGAAGCCCCCC
2101 ACCTTTCTCGCTGGAATCAATTTCCCAGAAGGGAGTTGCTCACTCAGGACTTTGATGCAT
2161 TTCCACACTGTCAGAGCTGTTGGCCTCGCCTGGGCCCAGGCTCTGGGAAGGGGTGCCCTC
```

FIGURE 2 (cont'd)

```
2221 TGGATCCTGCTGTGGCCTCACTTCCCTGGGAACTCATCCTGTGTGGGGAGGCAGCTCCAA
2281 CAGCTTGACCAGACCTAGACCTGGGCCAAAAGGGCAGGCCAGGGGCTGCTCATCACCCAG
2341 TCCTGGCCATTTTCTTGCCTGAGGCTCAAGAGGCCCAGGGAGCAATGGGAGGGGGCTCCA
2401 TGGAGGAGGTGTCCCAAGCTTTGAATACCCCCAGAGACCTTTTCTCTCCCATACCATCA
2461 CTGAGTGGCTTGTGATTCTGGGATGGACCCTCGCAGCAGGTGCAAGAGACAGAGCCCCCA
2521 AGCCTCTGCCCCAAGGGGCCCACAAAGGGGAGAAGGGCCAGCCCTACATCTTCAGCTCCC
2581 ATAGCGCTGGCTCAGGAAGAAACCCCAAGCAGCATTCAGCACACCCCAAGGGACAACCCC
2641 ATCATATGACATGCCACCCTCTCCATGCCCAACCTAAGATTGTGTGGGTTTTTTAATTAA
2701 AAATGTTAAAAGTTTTAAACATGAAAAAAAA G
     aattcggat ccgcggccgc atagataact gatccagtgt gctggaatta
1021 attcgctgtc tgcgagggcc agctgttggg gtgagtactc cctctcaaaa gcgggcatga
1081 cttctgcgct aagattgtca gtttccaaaa acgaggagga tttgatattc acctggcccg
1141 cggtgatgcc tttgagggtg gccgcgtcca tctggtcaga aaagacaatc ttttgttgt
1201 caagcttgag gtgtggcagg cttgagatct ggccatacac ttgagtgaca atgacatcca
1261 ctttgcctt ctctccacag gtgtccactc ccaggtccaa ctgcaggtcg agcatgcatc
1321 tagggcggcc aattccgccc ctctccctcc ccccccccta acgttactgg ccgaagccgc
1381 ttggaataag gccggtgtgc gtttgtctat atgtgatttt ccaccatatt gccgtctttt
1441 gcaatgtga gggcccggaa acctggccct gtcttcttga cgagcattcc taggggtctt
1501 tcccctctcg ccaaaggaat gcaaggtctg ttgaatgtcg tgaaggaagc agttcctctg
1561 gaagcttctt gaagacaaac aacgtctgta gcgacccttt gcaggcagcg gaaccccca
1621 cctggcgaca ggtgcctctg cggccaaaag ccacgtgtat aagatacacc tgcaaaggcg
1681 gcacaacccc agtgccacgt tgtgagttgg atagttgtgg aaagagtcaa atggctctcc
1741 tcaagcgtat tcaacaaggg gctgaaggat gccagaaggg taccccattg tatgggatct
1801 gatctggggc ctcggtgcac atgctttaca tgtgtttagt cgaggttaaa aaaacgtcta
1861 ggccccccga accacgggga cgtggttttc ctttgaaaaa cacgatgata agcttgccac
1921 aacccacaag gagacgacct tccatgaccg agtacaagcc cacggtgcgc ctcgccaccc
1981 gcgacgacgt cccccgggcc gtacgcaccc tcgccgccgc gttcgccgac taccccgcca
2041 cgcgccacac cgtcgacccg gaccgccaca tcgagcgggt caccgagctg caagaactct
2101 tcctcacgcg cgtcgggctc gacatcggca aggtgtgggt cgcggacgac ggcgccgcgg
2161 tggcggtctg gaccacgccg gagagcgtcg aagcggggc ggtgttcgcc gagatcggcc
2221 cgcgcatggc cgagttgagc ggttcccggc tggccgcgca gcaacagatg gaaggcctcc
2281 tggcgccgca ccggccaag gagcccgcgt ggttcctggc caccgtcggc gtctcgcccg
2341 accaccaggg caagggtctg ggcagcgccg tcgtgctccc cggagtggag gcggccgagc
2401 gcgccggggt gccccgccttc ctggagacct ccgcgccccg caacctcccc ttctacgagc
2461 ggctcggctt caccgtcacc gccgacgtcg agtgcccgaa ggaccgcgcg acctggtgca
2521 tgacccgcaa gcccggtgcc tgacgcccgc cccacgaccc gcagcgcccg accgaaagga
2581 gcgcacgacc ccatggctcc gaccgaagcc gacccgggcg gcccgccga ccccgcaccc
2641 gcccccgagg cccaccgact ctagataact gatcataatc agccatacca catttgtaga
2701 ggttttactt gctttaaaaa acctcccaca cctcccctg aacctgaaac ataaaatgaa
2761 tgcaattgtt gttgttaact tgtttattgc agcttataat ggttacaaat aaagcaatag
2821 catcacaaat ttcacaaata aagcatttt ttcactgcat tctagttgtg gtttgtccaa
2881 actcatcaat gtatcttaac gcgtcgagtg cattctagtt gtggtttgtc caaactcatc
2941 aatgtatctt atcatgtctg tataccgtcg acctctagct agagcttggc gtaatcatgg
3001 tcatagctgt ttcctgtgtg aaattgttat ccgctcacaa ttccacacaa catacgagcc
3061 ggaagcataa agtgtaaagc ctggggtgcc taatgagtga gctaactcac attaattgcg
3121 ttgcgctcac tgcccgcttt ccagtcggga aacctgtcgt gccagctgca ttaatgaatc
3181 ggccaacgcg cggggagagg cggtttgcgt attgggcgct cttccgcttc ctcgctcact
3241 gactcgctgc gctcggtcgt tcggctgcgg cgagcggtat cagctcactc aaaggcggta
3301 atacggttat ccacagaatc aggggataac gcaggaaaga acatgtgagc aaaaggccag
3361 caaaaggcca ggaaccgtaa aaaggccgcg ttgctggcgt ttttccatag gctccgcccc
3421 cctgacgagc atcacaaaaa tcgacgctca agtcagaggt ggcgaaaccc gacaggacta
3481 taaagatacc aggcgtttcc ccctggaagc tccctcgtgc gctctcctgt tccgaccctg
3541 ccgcttaccg gatacctgtc cgcctttctc ccttcgggaa gcgtggcgct ttctcaatgc
```

FIGURE 2 (cont'd)

```
3601 tcacgctgta ggtatctcag ttcggtgtag gtcgttcgct ccaagctggg ctgtgtgcac
3661 gaaccccccg ttcagcccga ccgctgcgcc ttatccggta actatcgtct tgagtccaac
3721 ccggtaagac acgacttatc gccactggca gcagccactg gtaacaggat tagcagagcg
3781 aggtatgtag gcggtgctac agagttcttg aagtggtggc ctaactacgg ctacactaga
3841 aggacagtat ttggtatctg cgctctgctg aagccagtta ccttcggaaa aagagttggt
3901 agctcttgat ccggcaaaca aaccaccgct ggtagcggtg gtttttttgt ttgcaagcag
3961 cagattacgc gcagaaaaaa aggatctcaa gaagatcctt tgatcttttc tacggggtct
4021 gacgctcagt ggaacgaaaa ctcacgttaa gggattttgg tcatgagatt atcaaaaagg
4081 atcttcacct agatcctttt aaattaaaaa tgaagtttta aatcaatcta agtatatat
4141 gagtaaactt ggtctgacag ttaccaatgc ttaatcagtg aggcacctat ctcagcgatc
4201 tgtctatttc gttcatccat agttgcctga ctccccgtcg tgtagataac tacgatacgg
4261 gagggcttac catctggccc cagtgctgca atgataccgc gagacccacg ctcaccggct
4321 ccagatttat cagcaataaa ccagccagcc ggaagggccg agcgcagaag tggtcctgca
4381 actttatccg cctccatcca gtctattaat tgttgccggg aagctagagt aagtagttcg
4441 ccagttaata gtttgcgcaa cgttgttgcc attgctacag gcatcgtggt gtcacgctcg
4501 tcgtttggta tggcttcatt cagctccggt tcccaacgat caaggcgagt tacatgatcc
4561 cccatgttgt gcaaaaaagc ggttagctcc ttcggtcctc cgatcgttgt cagaagtaag
4621 ttggccgcag tgttatcact catggttatg gcagcactgc ataattctct tactgtcatg
4681 ccatccgtaa gatgcttttc tgtgactggt gagtactcaa ccaagtcatt ctgagaatag
4741 tgtatgcggc gaccgagttg ctcttgcccg gcgtcaatac gggataatac cgcgccacat
4801 agcagaactt taaaagtgct catcattgga aaacgttctt cggggcgaaa actctcaagg
4861 atcttaccgc tgttgagatc cagttcgatg taacccactc gtgcacccaa ctgatcttca
4921 gcatctttta ctttcaccag cgtttctggg tgagcaaaaa caggaaggca aaatgccgca
4981 aaaaagggaa taagggcgac acggaaatgt tgaatactca tactcttcct ttttcaatat
5041 tattgaagca tttatcaggg ttattgtctc atgagcggat acatatttga atgtatttag
5101 aaaaataaac aataggggt tccgcgcaca tttccccgaa aagtgccacc tgacgtc
```

FIGURE 8
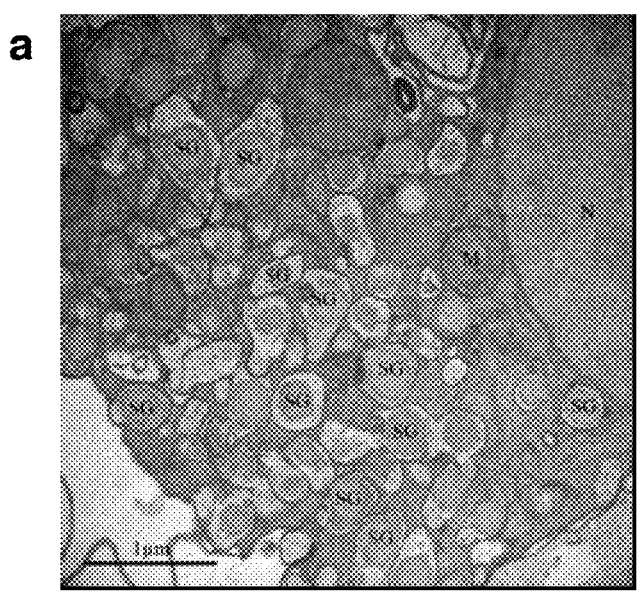
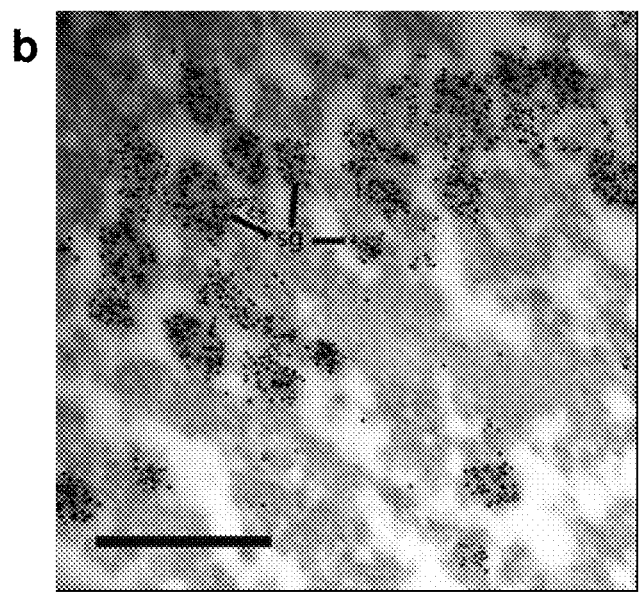

FIGURE 10
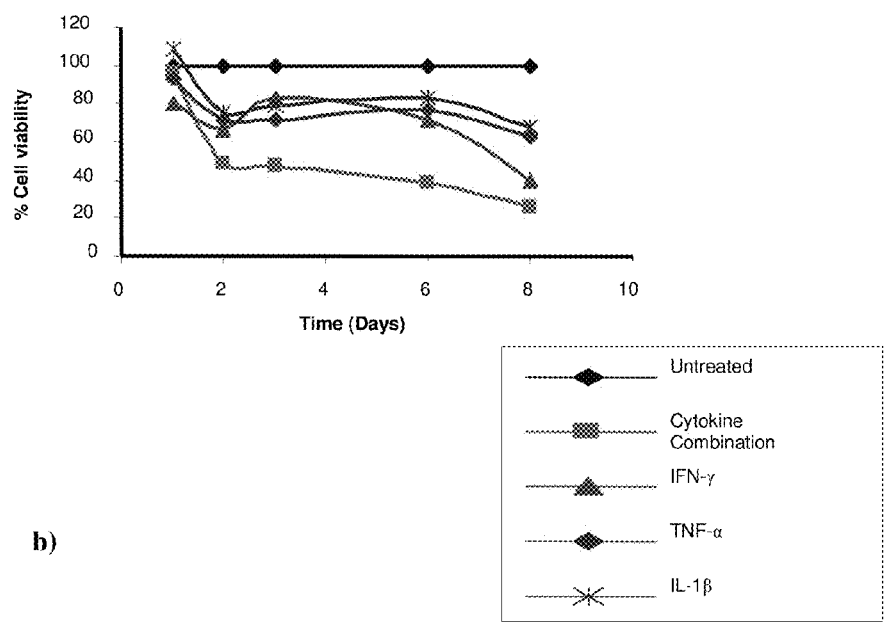
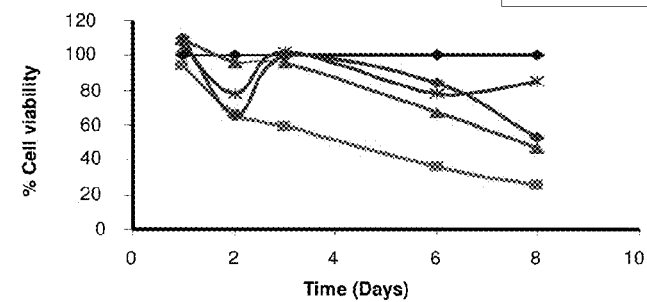

FIGURE 19
a)
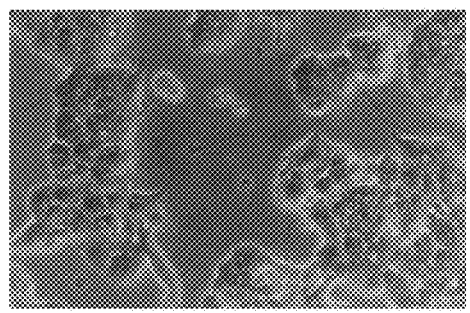
d)
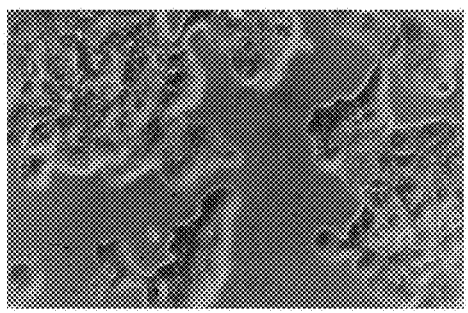
b)
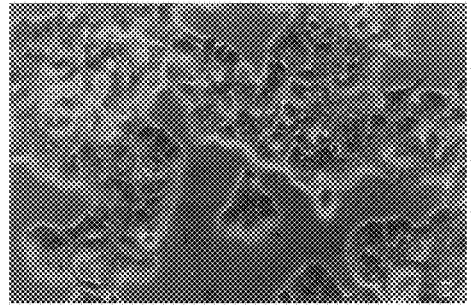
e)
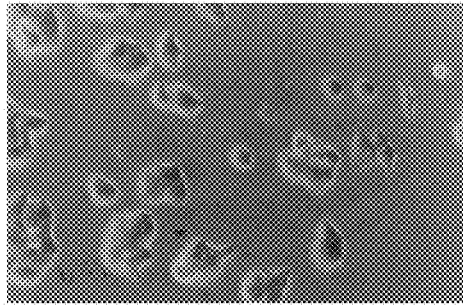
c)
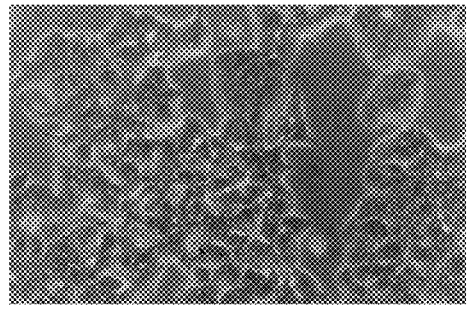
f)
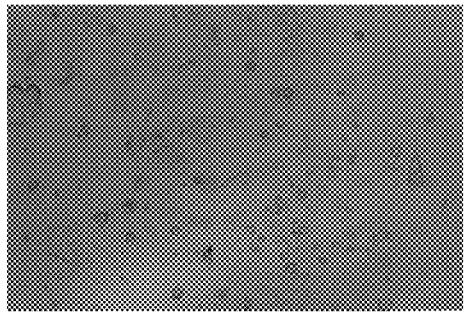

FIGURE 30
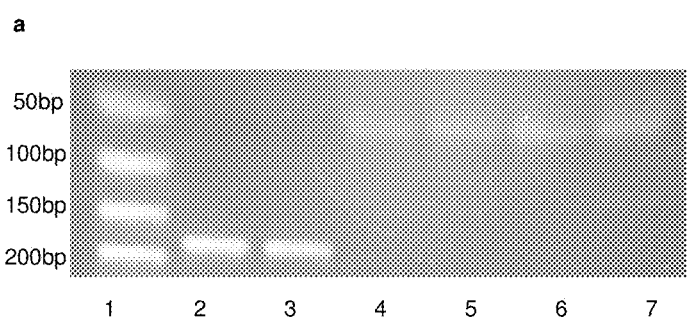
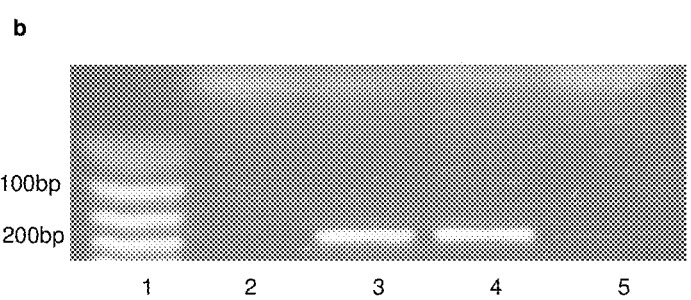

FIGURE 31
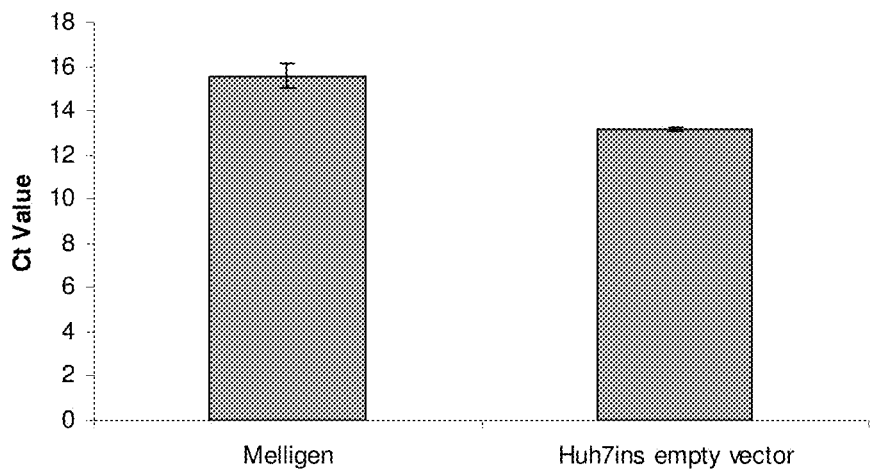
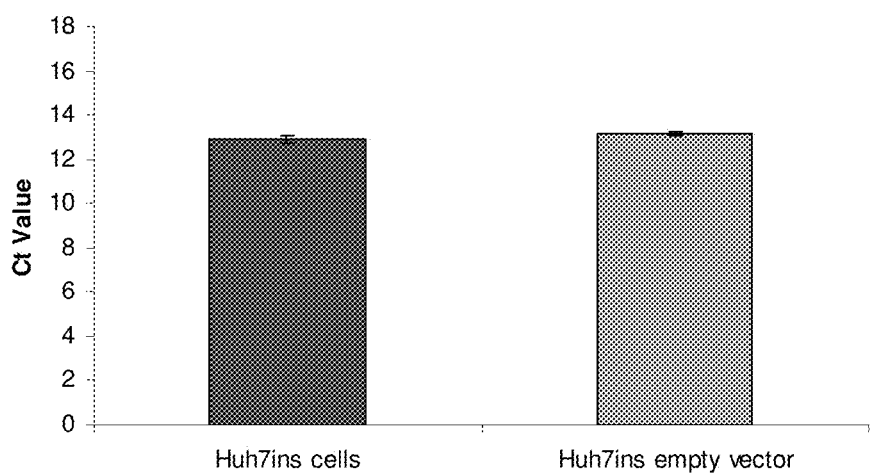

FIGURE 34
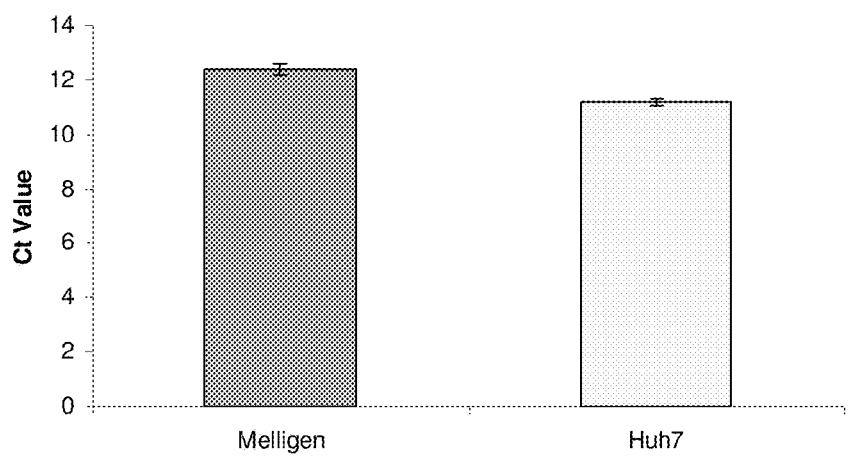
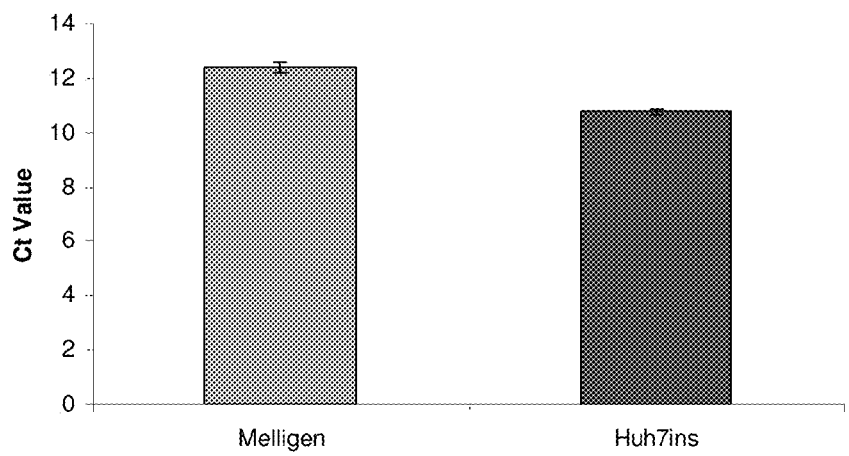

SEQUENCE LISTING

```
<160> NUMBER OF SEQ ID NOS: 33

<210> SEQ ID NO 1
<211> LENGTH: 5157
<212> TYPE: DNA
<213> ORGANISM: artificial sequence
<220> FEATURE:
<223> OTHER INFORMATION: mammalian pancreatic islet glucokinase

<400> SEQUENCE: 1
gacggatcgg gagatctccc gatccctat  ggtcgactct  cagtacaatc  tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gcttggtacc     900
gagctcggat cgatatctgc ggcctagcta gcgcttaagg cctgttaacc ggtcgtacgt     960
ctccggattc gaattcggat ccgcggccgc atagataact gatccagtgt gctggaatta    1020
```

```
attcgctgtc tgcgagggcc agctgttggg gtgagtactc cctctcaaaa gcgggcatga   1080
cttctgcgct aagattgtca gtttccaaaa acgaggagga tttgatattc acctggcccg   1140
cggtgatgcc tttgagggtg gccgcgtcca tctggtcaga aaagacaatc tttttgttgt   1200
caagcttgag gtgtggcagg cttgagatct ggccatacac ttgagtgaca atgcatcca    1260 ctttgccttt ctctccacag gtgtccactc ccaggtccaa ctgcaggtcg agcatgcatc   1320
tagggcggcc aattccgccc ctctccctcc cccccccta acgttactgg ccgaagccgc    1380
ttggaataag gccggtgtgc gtttgtctat atgtgatttt ccaccatatt gccgtctttt   1440
ggcaatgtga gggcccggaa acctggccct gtcttcttga cgagcattcc taggggtctt   1500
tcccctctcg ccaaaggaat gcaaggtctg ttgaatgtcg tgaaggaagc agttcctctg   1560
gaagcttctt gaagacaaac aacgtctgta gcgacccttt gcaggcagcg aaccccccca   1620
cctggcgaca ggtgcctctg cggccaaaag ccacgtgtat aagatacacc tgcaaaggcg   1680
gcacaacccc agtgccacgt tgtgagttgg atagttgtgg aaagagtcaa atggctctcc   1740
tcaagcgtat tcaacaaggg gctgaaggat gcccagaagg taccccattg tatgggatct   1800
gatctggggc ctcggtgcac atgctttaca tgtgtttagt cgaggttaaa aaaacgtcta   1860
ggccccccga accacgggga cgtggttttc ctttgaaaaa cacgatgata agcttgccac   1920
aacccacaag gagacgacct tccatgaccg agtacaagcc cacggtgcgc ctcgccaccc   1980
gcgacgacgt ccccgggcc gtacgcaccc tcgccgccgc gttcgccgac taccccgcca   2040
cgcgccacac cgtcgacccg gaccgccaca tcgagcgggt caccgagctg caagaactct   2100
tcctcacgcg cgtcgggctc gacatcggca aggtgtgggt cgcggacgac ggcgccgcgg   2160
tggcggtctg gaccacgccg gagagcgtcg aagcgggggc ggtgttcgcc gagatcggcc   2220
cgcgcatggc cgagttgagc ggttcccggc tggccgcgca gcaacagatg gaaggcctcc   2280
tggcgccgca ccggcccaag gagcccgcgt ggttcctggc caccgtcggc gtctcgcccg   2340
accaccaggg caagggtctg ggcagcgccg tcgtgctccc cggagtggag gcggccgagc   2400
gcgccggggt gcccgccttc ctggagacct ccgcgccccg caacctcccc ttctacgagc   2460
ggctcggctt caccgtcacc gccgacgtcg agtgccgaa ggaccgcgcg acctggtgca    2520
tgacccgcaa gcccggtgcc tgacgcccgc cccacgaccc gcagcgcccg accgaaagga   2580
gcgcacgacc ccatggctcc gaccgaagcc gacccgggcg gccccgccga ccccgcaccc   2640
gcccccgagg cccaccgact ctagataact gatcataatc agccatacca catttgtaga   2700
ggttttactt gctttaaaaa acctcccaca cctcccctg aacctgaaac ataaaatgaa    2760
tgcaattgtt gttgttaact tgtttattgc agcttataat ggttacaaat aaagcaatag   2820
catcacaaat ttcacaaata aagcattttt tcactgcat tctagttgtg gtttgtccaa    2880
actcatcaat gtatcttaac gcgtcgagtg cattctagtt gtggtttgtc caaactcatc   2940
aatgtatctt atcatgtctg tataccgtcg acctctagct agagcttggc gtaatcatgg   3000
tcatagctgt ttcctgtgtg aaattgttat ccgctcacaa ttccacacaa catacgagcc   3060
ggaagcataa agtgtaaagc ctggggtgcc taatgagtga gctaactcac attaattgcg   3120
ttgcgctcac tgcccgcttt ccagtcggga acctgtcgt gccagctgca ttaatgaatc     3180
ggccaacgcg cggggagagg cggtttgcgt attgggcgct cttccgcttc ctcgctcact   3240
gactcgctgc gctcggtcgt tcggctgcgg cgagcggtat cagctcactc aaaggcggta   3300
atacggttat ccacagaatc aggggataac gcaggaaaga acatgtgagc aaaaggccag   3360
caaaaggcca ggaaccgtaa aaaggccgcg ttgctggcgt ttttccatag gctccgcccc   3420
```

```
cctgacgagc atcacaaaaa tcgacgctca agtcagaggt ggcgaaaccc gacaggacta    3480
taaagatacc aggcgtttcc ccctggaagc tccctcgtgc gctctcctgt tccgaccctg    3540
ccgcttaccg gatacctgtc cgcctttctc ccttcgggaa gcgtggcgct ttctcaatgc    3600
tcacgctgta ggtatctcag ttcggtgtag gtcgttcgct ccaagctggg ctgtgtgcac    3660
gaaccccccg ttcagcccga ccgctgcgcc ttatccggta actatcgtct tgagtccaac    3720
ccggtaagac acgacttatc gccactggca gcagccactg gtaacaggat tagcagagcg    3780
aggtatgtag gcggtgctac agagttcttg aagtggtggc ctaactacgg ctacactaga    3840
aggacagtat ttggtatctg cgctctgctg aagccagtta ccttcggaaa aagagttggt    3900
agctcttgat ccggcaaaca aaccaccgct ggtagcggtg gttttttttgt ttgcaagcag    3960 cagattacgc gcagaaaaaa aggatctcaa gaagatcctt tgatcttttc tacgggtct     4020 gacgctcagt ggaacgaaaa ctcacgttaa gggattttgg tcatgagatt atcaaaaagg    4080
atcttcacct agatcctttt aaattaaaaa tgaagtttta atcaatcta aagtatatat     4140 gagtaaactt ggtctgacag ttaccaatgc ttaatcagtg aggcacctat ctcagcgatc    4200
tgtctatttc gttcatccat agttgcctga ctccccgtcg tgtagataac tacgatacgg    4260
gagggcttac catctggccc cagtgctgca atgataccgc gagacccacg ctcaccggct    4320
ccagatttat cagcaataaa ccagccagcc ggaagggccg agcgcagaag tggtcctgca    4380
actttatccg cctccatcca gtctattaat tgttgccggg aagctagagt aagtagttcg    4440
ccagttaata gtttgcgcaa cgttgttgcc attgctacag gcatcgtggt gtcacgctcg    4500
tcgtttggta tggcttcatt cagctccggt tcccaacgat caaggcgagt tacatgatcc    4560
cccatgttgt gcaaaaaagc ggttagctcc ttcggtcctc cgatcgttgt cagaagtaag    4620
ttggccgcag tgttatcact catggttatg gcagcactgc ataattctct tactgtcatg    4680
ccatccgtaa gatgcttttc tgtgactggt gagtactcaa ccaagtcatt ctgagaatag    4740
tgtatgcggc gaccgagttg ctcttgcccg gcgtcaatac gggataatac cgcgccacat    4800
agcagaactt taaaagtgct catcattgga aaacgttctt cggggcgaaa actctcaagg    4860
atcttaccgc tgttgagatc cagttcgatg taacccactc gtgcacccaa ctgatcttca    4920
gcatctttta ctttcaccag cgtttctggg tgagcaaaaa caggaaggca aaatgccgca    4980 aaaagggaa taagggcgac acggaaatgt tgaatactca tactcttcct ttttcaatat    5040
tattgaagca tttatcaggg ttattgtctc atgagcggat acatatttga atgtatttag    5100
aaaaataaac aaatagggt tccgcgcaca tttccccgaa aagtgccacc tgacgtc       5157
```

<210> SEQ ID NO 2
<211> LENGTH: 2732
<212> TYPE: DNA
<213> ORGANISM: artificial sequence
<220> FEATURE:
<223> OTHER INFORMATION: mammalian pancreatic islet glucokinase

<400> SEQUENCE: 2

```
ccgagcggcg cctgagcccc agggaagcag gctaggatgt gagagacaca gtcacctgca      60
gcctaattac tcaaaagctg tccccaggtc acagaaggga gaggacattt cccactgaat     120
ctgtctgaag gacactaagc cccacagctc aacacaacca ggagagaaag cgctgaggac     180
gccacccaag cgcccagcaa tggccctgcc tggagaacat ccaggctcag tgaggaaggg     240
tccagaaggg aatgcttgcc gactcgttgg agaacaatga aaaggaggaa actgtgactg     300
```

```
aacctcaaac cccaaaccag cccgaggaga accacattct cccagggacc cagggcgggc    360
cgtgacccct gcggcggaga agccttggat atttccactt cagaagccta ctggggaagg    420
ctgagggatc ccagctcccc acgctggctg ctgtgcagat gctggacgac agagccagga    480
tggaggccgc caagaaggag aaggtagagc agatcctggc agagttccag ctgcaggagg    540
aggacctgaa gaaggtgatg agacggatgc agaaggagat ggaccgcggc ctgaggctgg    600
agacccatga gaggccagt gtgaagatgc tgcccaccta cgtgcgctcc acccagaag     660 gctcagaagt cggggacttc ctctccctgg acctgggtgg cactaacttc agggtgatgc    720
tggtgaaggt gggagaaggt gaggaggggc agtggagcgt gaagaccaaa caccagatgt    780
actccatccc cgaggacgcc atgaccggca ctgctgagat gctcttcgac tacatctctg    840
agtgcatctc cgacttcctg gacaagcatc agatgaaaca caagaagctg cccctgggct    900
tcaccttctc ctttcctgtg aggcacgaag acatcgataa gggcatcctt ctcaactgga    960
ccaagggctt caaggcctca ggagcagaag ggaacaatgt cgtggggctt ctgcgagacg   1020
ctatcaaacg gagaggggac tttgaaatgg atgtggtggc aatggtgaat gacacggtgg   1080
ccacgatgat ctcctgctac tacgaagacc atcagtgcga ggtcggcatg atcgtgggca   1140
cgggctgcaa tgcctgctac atggaggaga tgcagaatgt ggagctggtg aggggggacg   1200
agggccgcat gtgcgtcaat accgagtggg gcgccttcgg ggactccggc agctggacg    1260 agttcctgct ggagtatgac cgcctggtgg acgagagctc tgcaaacccc ggtcagcagc   1320
tgtatgagaa gctcataggt ggcaagtaca tgggcgagct ggtgcggctt gtgctgctca   1380
ggctcgtgga cgaaaacctg ctcttccacg gggaggcctc cgagcagctg cgcacacgcg   1440
gagccttcga cgcgcttc gtgtcgcagg tggagagcga cacgggcgac cgcaagcaga   1500
tctacaacat cctgagcacg ctggggctgc gaccctcgac caccgactgc gacatcgtgc   1560
gccgcgcctg cgagagcgtg tctacgcgcg ctgcgcacat gtgctcggcg gggctggcgg   1620
gcgtcatcaa ccgcatgcgc gagagccgca gcgaggacgt aatgcgcatc actgtgggcg   1680
tggatggctc cgtgtacaag ctgcaccca gcttcaagga gcggttccat gccagcgtgc   1740
gcaggctgac gcccagctgc gagatcacct tcatcgagtc ggaggagggc agtggccggg   1800
gcgcggccct ggtctcggcg gtggcctgta agaaggcctg tatgctgggc cagtgagagc   1860
agtggccgca agcgcaggga ggatgccaca gccccacagc acccaggctc catggggaag   1920
tgctccccac acgtgctcgc agcctggcgg ggcaggaggc ctggccttgt caggacccag   1980
gccgcctgcc ataccgctgg ggaacagagc gggcctcttc cctcagtttt tcggtgggac   2040
agccccaggg ccctaacggg ggtgcggcag gagcaggaac agagactctg gaagcccccc   2100
acctttctcg ctggaatcaa tttcccagaa gggagttgct cactcaggac tttgatgcat   2160
ttccacactg tcagagctgt tggcctcgcc tgggcccagg ctctgggaag gggtgccctc   2220
tggatcctgc tgtggcctca cttccctggg aactcatcct gtgtggggag cagctccaa   2280 cagcttgacc agacctagac ctgggccaaa agggcaggcc aggggctgct catcacccag   2340
tcctggccat tttcttgcct gaggctcaag aggcccaggg agcaatggga gggggctcca   2400
tggaggaggt gtcccaagct tgaatacccc ccagagacc ttttctctcc cataccatca   2460
ctgagtggct tgtgattctg ggatggaccc tcgcagcagg tgcaagagac agagccccca   2520
agcctctgcc ccaaggggcc cacaaagggg agaagggcca gccctacatc ttcagctccc   2580
atagcgctgg ctcaggaaga aaccccaagc agcattcagc acaccccaag ggacaacccc   2640
atcatatgac atgccacccct ctccatgccc aacctaagat tgtgtgggtt ttttaattaa   2700
```

```
aaatgttaaa agttttaaac atgaaaaaaa ag                                    2732

<210> SEQ ID NO 3
<211> LENGTH: 7889
<212> TYPE: DNA
<213> ORGANISM: artificial sequence
<220> FEATURE:
<223> OTHER INFORMATION: mammalian pancreatic islet glucokinase

<400> SEQUENCE: 3
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat cgatatctgc ggcctagcta gcgcttaagg cctgttaacc ggtcgtacgt    960
ctccggattc gccgagcggc gcctgagccc cagggaagca ggctaggatg tgagagacac   1020
agtcacctgc agcctaatta ctcaaaagct gtccccaggt cacagaaggg agaggacatt   1080
tcccactgaa tctgtctgaa ggacactaag ccccacagct caacacaacc aggagagaaa   1140
gcgctgagga cgccacccaa cgcccagca atggccctgc ctggagaaca tccaggctca   1200
gtgaggaagg gtccagaagg aatgcttgc cgactcgttg gagaacaatg aaaaggagga   1260
aactgtgact gaacctcaaa ccccaaacca gcccgaggag aaccacattc tcccagggac   1320
ccagggcggg ccgtgacccc tgcggcggag aagccttgga tatttccact tcagaagcct   1380
actggggaag gctgaggggt cccagctccc cacgctggct gctgtgcaga tgctggacga   1440
cagagccagg atgaggccg ccaagaagga aaggtagag cagatcctgg cagagttcca   1500
gctgcaggag gaggacctga gaaggtgat gagacggatg cagaaggaga tggaccgcgg   1560
cctgaggctg gagacccatg aagaggccag tgtgaagatg ctgcccacct acgtgcgctc   1620
caccccagaa ggctcagaag tcggggactt cctctccctg gacctgggtg gcactaactt   1680
cagggtgatg ctggtgaagg tgggagaagg tgaggagggg cagtggagcg tgaagaccaa   1740
acaccagatg tactccatcc ccgaggacgc catgaccggc actgctgaga tgctcttcga   1800
ctacatctct gagtgcatct ccgacttcct ggacaagcat cagatgaaac acaagaagct   1860
gccccctggg cttcaccttc cctttcctgt gaggcacgaa gacatcgata gggcatcct   1920
tctcaactgg accaagggct tcaaggcctc aggagcagaa gggaacaatg tcgtgggct   1980
```

```
tctgcgagac gctatcaaac ggagagggga ctttgaaatg gatgtggtgg caatggtgaa    2040
tgacacggtg gccacgatga tctcctgcta ctacgaagac catcagtgcg aggtcggcat    2100
gatcgtgggc acgggctgca atgcctgcta catggaggag atgcagaatg tggagctggt    2160 ggaggggac gagggccgca tgtgcgtcaa taccgagtgg ggcgccttcg gggactccgg    2220
cgagctggac gagttcctgc tggagtatga ccgcctggtg gacgagagct ctgcaaaccc    2280
cggtcagcag ctgtatgaga agctcatagg tggcaagtac atgggcgagc tggtgcggct    2340
tgtgctgctc aggctcgtgg acgaaaacct gctcttccac ggggaggcct ccgagcagct    2400
gcgcacacgc ggagccttcg agacgcgctt cgtgtcgcag gtggagagcg acacgggcga    2460
ccgcaagcag atctacaaca tcctgagcac gctggggctg cgaccctcga ccaccgactg    2520
cgacatcgtg cgccgcgcct gcgagagcgt gtctacgcgc gctgcgcaca tgtgctcggc    2580
ggggctggcg ggcgtcatca accgcatgcg cgagagccgc agcgaggacg taatgcgcat    2640
cactgtgggc gtggatggct ccgtgtacaa gctgcacccc agcttcaagg agcggttcca    2700
tgccagcgtg cgcaggctga cgcccagctg cgagatcacc ttcatcgagt cggaggaggg    2760
cagtggccgg ggcgcggccc tggtctcggc ggtggcctgt aagaaggcct gtatgctggg    2820
ccagtgagag cagtggccgc aagcgcaggg aggatgccac agcccacag cacccaggct    2880 ccatggggaa gtgctcccca cacgtgctcg cagcctggcg gggcaggagg cctggccttg    2940
tcaggaccca ggccgcctgc cataccgctg ggaacagag cgggcctctt ccctcagttt    3000
ttcggtggga cagccccagg gccctaacgg gggtgcggca ggagcaggaa cagagactct    3060
ggaagccccc caccttttctc gctggaatca atttcccaga agggagttgc tcactcagga    3120
ctttgatgca tttccacact gtcagagctg ttggcctcgc ctgggcccag gctctgggaa    3180
ggggtgccct ctggatcctg ctgtggcctc acttccctgg gaactcatcc tgtgtgggga    3240
ggcagctcca acagcttgac cagacctaga cctgggccaa aagggcaggc caggggctgc    3300
tcatcaccca gtcctggcca ttttcttgcc tgaggctcaa gaggcccagg gagcaatggg    3360
aggggcctcc atggaggagg tgtcccaagc tttgaatacc ccccagagac cttttctctc    3420
ccataccatc actgagtggc ttgtgattct gggatggacc ctcgcagcag gtgcaagaga    3480
cagagccccc aagcctctgc cccaaggggc ccacaaaggg gagaagggcc agccctacat    3540
cttcagctcc catagcgctg gctcaggaag aaaccccaag cagcattcag cacaccccaa    3600
gggacaaccc catcatatga catgccaccc tctccatgcc caacctaaga ttgtgtgggt    3660
tttttaatta aaaatgttaa aagttttaaa catgaaaaaa aagaattcgg atccgcggcc    3720
gcatagataa ctgatccagt gtgctggaat taattcgctg tctgcgaggg ccagctgttg    3780
gggtgagtac tccctctcaa aagcgggcat gacttctgcg ctaagattgt cagtttccaa    3840
aaacgaggag gatttgatat tcacctggcc cgcggtgatg cctttgaggg tggccgcgtc    3900
catctggtca gaaagacaa tctttttgtt gtcaagcttg aggtgtggca ggcttgagat    3960
ctggccatac acttgagtga caatgacatc cactttgcct ttctctccac aggtgtccac    4020
tcccaggtcc aactgcaggt cgagcatgca tctagggcgg ccaattcgc ccctctccct    4080 cccccccccc taacgttact ggccgaagcc gcttggaata aggccggtgt gcgtttgtct    4140
atatgtgatt ttccaccata ttgccgtctt ttggcaatgt gagggcccgg aaacctggcc    4200
ctgtcttctt gacgagcatt cctaggggtc tttcccctct cgccaaagga atgcaaggtc    4260
tgttgaatgt cgtgaaggaa gcagttcctc tggaagcttc ttgaagacaa acaacgtctg    4320
tagcgaccct ttgcaggcag cggaaccccc cacctggcga caggtgcctc tgcggccaaa    4380
```

```
agccacgtgt ataagataca cctgcaaagg cggcacaacc ccagtgccac gttgtgagtt    4440
ggatagttgt ggaaagagtc aaatggctct cctcaagcgt attcaacaag gggctgaagg    4500
atgcccagaa ggtacccat  tgtatgggat ctgatctggg gcctcggtgc acatgcttta    4560
catgtgttta gtcgaggtta aaaaaacgtc taggccccc  gaaccacggg gacgtggttt    4620
tcctttgaaa aacacgatga taagcttgcc acaacccaca aggagacgac cttccatgac    4680
cgagtacaag cccacggtgc gcctcgccac ccgcgacgac gtcccccggg ccgtacgcac    4740
cctcgccgcc gcgttcgccg actaccccgc cacgcgccac accgtcgacc cggaccgcca    4800
catcgagcgg gtcaccgagc tgcaagaact cttcctcacg cgcgtcgggc tcgacatcgg    4860
caaggtgtgg gtcgcggacg acggcgccgc ggtggcggtc tggaccacgc cggagagcgt    4920
cgaagcgggg gcggtgttcg ccgagatcgg cccgcgcatg gccgagttga gcggttcccg    4980
gctggccgcg cagcaacaga tggaaggcct cctggcgccg caccggccca aggagcccgc    5040
gtggttcctg gccaccgtcg gcgtctcgcc cgaccaccag ggcaagggtc tgggcagcgc    5100
cgtcgtgctc cccggagtgg aggcggccga gcgcgccggg gtgcccgcct tcctggagac    5160
ctccgcgccc cgcaacctcc ccttctacga gcggctcggc ttcaccgtca ccgccgacgt    5220
cgagtgcccg aaggaccgcg cgacctggtg catgacccgc aagcccggtg cctgacgccc    5280
gccccacgac ccgcagcgcc cgaccgaaag gagcgcacga ccccatggct ccgaccgaag    5340
ccgacccggg cggccccgcc gaccccgcac ccgcccccga ggcccaccga ctctagataa    5400
ctgatcataa tcagccatac cacatttgta gaggttttac ttgctttaaa aaacctccca    5460
cacctccccc tgaacctgaa acataaaatg aatgcaattg ttgttgttaa cttgtttatt    5520
gcagcttata atggttacaa ataaagcaat agcatcacaa atttcacaaa taaagcattt    5580
ttttcactgc attctagttg tggtttgtcc aaactcatca atgtatctta acgcgtcgag    5640
tgcattctag ttgtggtttg tccaaactca tcaatgtatc ttatcatgtc tgtataccgt    5700
cgacctctag ctagagcttg gcgtaatcat ggtcatagct gtttcctgtg tgaaattgtt    5760
atccgctcac aattccacac aacatacgag ccggaagcat aaagtgtaaa gcctggggtg    5820
cctaatgagt gagctaactc acattaattg cgttgcgctc actgcccgct ttccagtcgg    5880
gaaacctgtc gtgccagctg cattaatgaa tcggccaacg cgcggggaga ggcggtttgc    5940
gtattgggcg ctcttccgct tcctcgctca ctgactcgct gcgctcggtc gttcggctgc    6000
ggcgagcggt atcagctcac tcaaaggcgg taatacggtt atccacagaa tcaggggata    6060
acgcaggaaa gaacatgtga gcaaaaggcc agcaaaaggc caggaaccgt aaaaaggccg    6120
cgttgctggc gtttttccat aggctccgcc ccctgacga  gcatcacaaa atcgacgct    6180 caagtcagag gtggcgaaac ccgacaggac tataaagata ccaggcgttt ccccctggaa    6240
gctccctcgt gcgctctcct gttccgaccc tgccgcttac cggatacctg tccgcctttc    6300
tcccttcggg aagcgtggcg ctttctcaat gctcacgctg taggtatctc agttcggtgt    6360
aggtcgttcg ctccaagctg ggctgtgtgc acgaaccccc cgttcagccc gaccgctgcg    6420
ccttatccgg taactatcgt cttgagtcca acccggtaag acacgactta tcgccactgg    6480
cagcagccac tggtaacagg attagcagag cgaggtatgt aggcggtgct acagagttct    6540
tgaagtggtg gcctaactac ggctacacta aaggacagt  atttggtatc tgcgctctgc    6600
tgaagccagt taccttcgga aaagagttg  gtagctcttg atccggcaaa caaaccaccg    6660
ctggtagcgg tggttttttt gtttgcaagc agcagattac gcgcagaaaa aaaggatctc    6720
```

```
aagaagatcc tttgatctttt tctacggggt ctgacgctca gtggaacgaa aactcacgtt    6780
aagggatttt ggtcatgaga ttatcaaaaa ggatcttcac ctagatcctt ttaaattaaa    6840
aatgaagttt taaatcaatc taaagtatat atgagtaaac ttggtctgac agttaccaat    6900
gcttaatcag tgaggcacct atctcagcga tctgtctatt tcgttcatcc atagttgcct    6960
gactccccgt cgtgtagata actacgatac gggagggctt accatctggc cccagtgctg    7020
caatgatacc gcgagaccca cgctcaccgg ctccagattt atcagcaata aaccagccag    7080
ccggaagggc cgagcgcaga agtggtcctg caactttatc cgcctccatc cagtctatta    7140
attgttgccg ggaagctaga gtaagtagtt cgccagttaa tagtttgcgc aacgttgttg    7200
ccattgctac aggcatcgtg gtgtcacgct cgtcgtttgg tatggcttca ttcagctccg    7260
gttcccaacg atcaaggcga gttacatgat cccccatgtt gtgcaaaaaa gcggttagct    7320
ccttcggtcc tccgatcgtt gtcagaagta agttggccgc agtgttatca ctcatggtta    7380
tggcagcact gcataattct cttactgtca tgccatccgt aagatgcttt tctgtgactg    7440
gtgagtactc aaccaagtca ttctgagaat agtgtatgcg cgaccgagt tgctcttgcc     7500 cggcgtcaat acgggataat accgcgccac atagcagaac tttaaaagtg ctcatcattg    7560
gaaaacgttc ttcggggcga aaactctcaa ggatcttacc gctgttgaga tccagttcga    7620
tgtaacccac tcgtgcaccc aactgatctt cagcatcttt tactttcacc agcgtttctg    7680
ggtgagcaaa aacaggaagg caaaatgccg caaaaaaggg aataagggcg acacggaaat    7740
gttgaatact catactcttc ctttttcaat attattgaag catttatcag ggttattgtc    7800
tcatgagcgg atacatattt gaatgtattt agaaaaataa acaaataggg gttccgcgca    7860
catttccccg aaaagtgcca cctgacgtc                                     7889

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
ctgagtggct tgtgattctg                                                 20

<210> SEQ ID NO 5
<211> LENGTH: 19
<212> TYPE: DNA
<213> ORGANISM: artificial sequence
<220> FEATURE:
<223> OTHER INFORMATION: primer

<400> SEQUENCE: 5
aatcttaggt tgggcatgg                                                  19

<210> SEQ ID NO 6
<211> LENGTH: 19
<212> TYPE: DNA
<213> ORGANISM: artificial sequence
<220> FEATURE:
<223> OTHER INFORMATION: primer

<400> SEQUENCE: 6
cccatggatg aagtctacc                                                  19

<210> SEQ ID NO 7
<211> LENGTH: 19
```

```
<212> TYPE: DNA
<213> ORGANISM: artificial sequence
<220> FEATURE:
<223> OTHER INFORMATION: primer

<400> SEQUENCE: 7
gtcctcctcc tttttccac                                               19

<210> SEQ ID NO 8
<211> LENGTH: 19
<212> TYPE: DNA
<213> ORGANISM: artificial sequence
<220> FEATURE:
<223> OTHER INFORMATION: primer

<400> SEQUENCE: 8
agacgacgcg aagctcacc                                               19

<210> SEQ ID NO 9
<211> LENGTH: 19
<212> TYPE: DNA
<213> ORGANISM: artificial sequence
<220> FEATURE:
<223> OTHER INFORMATION: primer

<400> SEQUENCE: 9
aagccagact gcctgggct                                               19

<210> SEQ ID NO 10
<211> LENGTH: 21
<212> TYPE: DNA
<213> ORGANISM: artificial sequence
<220> FEATURE:
<223> OTHER INFORMATION: primer

<400> SEQUENCE: 10
tcactgctca ggacctacta a                                            21

<210> SEQ ID NO 11
<211> LENGTH: 19
<212> TYPE: DNA
<213> ORGANISM: artificial sequence
<220> FEATURE:
<223> OTHER INFORMATION: primer

<400> SEQUENCE: 11
ctcctcgtcc tgagaactg                                               19

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12
tgcagcacat gcagtacaac g                                            21

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
```
tcccaaggtt cagaaggaga gg                                          22

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
tcttctggcc cggggtgatg                                             20

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
agccgcgtgc ttcttcctcc                                             20

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
caaaagtcca agtgctggac aa                                          22

<210> SEQ ID NO 17
<211> LENGTH: 20
<212> TYPE: DNA
<213> ORGANISM: artificial sequence
<220> FEATURE:
<223> OTHER INFORMATION: primer

<400> SEQUENCE: 17
cccatctgtt gcttttcgct                                             20

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
ctcctaaaag acttgcggaa tcac                                        24

<210> SEQ ID NO 19
<211> LENGTH: 25
<212> TYPE: DNA
<213> ORGANISM: artificial sequence
<220> FEATURE:
<223> OTHER INFORMATION: primer

<400> SEQUENCE: 19
tccacacagg cactaagaaa gactg                                       25

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
gcgggattac cagtccaagt tg                                              22

<210> SEQ ID NO 21
<211> LENGTH: 21
<212> TYPE: DNA
<213> ORGANISM: artificial sequence
<220> FEATURE:
<223> OTHER INFORMATION: primer

<400> SEQUENCE: 21
tgtgctttca gagatgtggc g                                               21

<210> SEQ ID NO 22
<211> LENGTH: 20
<212> TYPE: DNA
<213> ORGANISM: artificial sequence
<220> FEATURE:
<223> OTHER INFORMATION: primer

<400> SEQUENCE: 22
ttggtgtgat caatgcacct                                                 20

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
gccacagtct cttcctcagc                                                 20

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
ctgcctccca aagcatctac                                                 20

<210> SEQ ID NO 25
<211> LENGTH: 20
<212> TYPE: DNA
<213> ORGANISM: artificial sequence
<220> FEATURE:
<223> OTHER INFORMATION: primer

<400> SEQUENCE: 25
gatcttggtc tgggcatgtt                                                 20

<210> SEQ ID NO 26
<211> LENGTH: 20
<212> TYPE: DNA
<213> ORGANISM: artificial sequence
<220> FEATURE:
<223> OTHER INFORMATION: primer

<400> SEQUENCE: 26
tcagaagcct actggggaag                                                 20

```
<210> SEQ ID NO 27
<211> LENGTH: 20
<212> TYPE: DNA
<213> ORGANISM: artificial sequence
<220> FEATURE:
<223> OTHER INFORMATION: primer

<400> SEQUENCE: 27
cttctgcatc cgtctcatca                                               20

<210> SEQ ID NO 28
<211> LENGTH: 22
<212> TYPE: DNA
<213> ORGANISM: artificial sequence
<220> FEATURE:
<223> OTHER INFORMATION: primer

<400> SEQUENCE: 28
cccaagattt tgtgcagtgg tt                                            22

<210> SEQ ID NO 29
<211> LENGTH: 21
<212> TYPE: DNA
<213> ORGANISM: artificial sequence
<220> FEATURE:
<223> OTHER INFORMATION: primer

<400> SEQUENCE: 29
gcggccaagt tcttcaacaa t                                             21

<210> SEQ ID NO 30
<211> LENGTH: 21
<212> TYPE: DNA
<213> ORGANISM: artificial sequence
<220> FEATURE:
<223> OTHER INFORMATION: primer

<400> SEQUENCE: 30
atgctgtcct gccgcctcca g                                             21

<210> SEQ ID NO 31
<211> LENGTH: 21
<212> TYPE: DNA
<213> ORGANISM: artificial sequence
<220> FEATURE:
<223> OTHER INFORMATION: primer

<400> SEQUENCE: 31
acaggatgtg aaagtcttcc a                                             21

<210> SEQ ID NO 32
<211> LENGTH: 22
<212> TYPE: DNA
<213> ORGANISM: artificial sequence
<220> FEATURE:
<223> OTHER INFORMATION: primer

<400> SEQUENCE: 32
caatgccaca ccagagcaga tg                                            22

<210> SEQ ID NO 33
<211> LENGTH: 18
<212> TYPE: DNA
<213> ORGANISM: artificial sequence
<220> FEATURE:
<223> OTHER INFORMATION: primer
```

```
<400> SEQUENCE: 33
tgggagcagg gagcaagc                                                    18
```

CELLS GENETICALLY MODIFIED TO COMPRISE PANCREATIC ISLET GLUCOKINASE AND USES THEREOF

CROSS-REFERENCE TO RELATED APPLICATIONS

This application is a continuation of U.S. application Ser. No. 14/185,716, filed Feb. 20, 2014, which is a continuation of U.S. application Ser. No. 12/672,832, filed on Jun. 3, 2011, which claims the benefit of priority to and is a U.S. National Phase Application of PCT International Application Number PCT/AU2008/001160, filed on Aug. 8, 2008, designating the United States of America and published in the English language, which is an International Application of and claims the benefit of priority to Australian Patent Application No. 2007904310, filed on Aug. 10, 2007. The disclosures of the above-referenced applications are hereby expressly incorporated by reference in their entireties.

REFERENCE TO SEQUENCE LISTING

The present application is being filed along with a sequence listing in electronic format. The sequence listing is provided as a file entitled SequenceListing-WMRK7-001C2, created Feb. 25, 2016 which is 25 KB in size. The information in the electronic format of the sequence listing is incorporated herein by reference in its entirety.

FIELD OF THE INVENTION

The present invention relates generally to a population of cells genetically modified to produce insulin in a glucose responsive manner and uses thereof. More particularly, the present invention relates to a population of cells genetically modified to produce insulin in response to physiologically relevant levels of glucose and uses thereof. The cells of the present invention are useful in a wide variety of applications, in particular in the context of therapeutic and prophylactic regimes directed to the treatment of diabetes and/or the amelioration of symptoms associated with diabetes, based on the transplantation of the cells of the present invention into mammals requiring treatment. Also facilitated is the design of in vitro based screening systems for testing the therapeutic effectiveness and/or toxicity of potential adjunctive treatment regimes.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Diabetes mellitus is characterised by an abnormality of carbohydrate metabolism resulting in elevated glucose levels in both the blood and the urine. The failure of the human body to properly metabolise the glucose is caused by defects in insulin secretion or use of insulin. Insulin is produced by β-cells in the islets of the pancreas and permits the body to utilise glucose as a source of energy. When this process cannot occur, the body compensates by utilising alternative sources of energy such as stored fats. However, this leads to rapidly rising levels of glucose and the accumulation of ketones in the bloodstream due to the occurrence of extensive fat metabolism.

Diabetes is broadly classified into two groups termed Type 1 diabetes and Type 2 diabetes. Type 1 diabetes (often referred to as juvenile onset diabetes due to its appearance in childhood or early adolescence) is a debilitating autoimmune condition caused by the selective destruction of insulin producing β-cells in the islets of the pancreas. Its onset is abrupt and occurs typically prior to the age of 20 years. Presently, however, Type 1 diabetes is increasingly presenting in adults. This disease is characterised by lack of β-cell function and no insulin production, and therefore insulin therapy is required. Type 2 diabetes, however, is characterised by insulin resistance, a condition in which the body fails to properly use insulin, which is often accompanied by obesity and other metabolic disorders. There are frequently no overt symptoms observed. Insulin secretory defects are evident very early in disease in both Type 1 and Type 2 diabetes, despite their differing aetiology.

In the absence of treatment, diabetes can be fatal while poorly controlled diabetes leads to the appearance of complications such as diabetic glomerulosclerosis, wherein the kidneys are irreversibly damaged leading to renal failure. Treatment of type 1 diabetes and also severe symptoms of type 2 diabetes is generally by daily insulin injection to replace the insulin which the damaged β cells are no longer able to produce. However, even in the face of an optimised treatment regime of this type, complications and side effects are common. For example, diabetic vascular complications, affecting both micro- and macro-blood vessels, represent major causes of disability and death in the patients with type 1 and type 2 diabetes. In fact, diabetes is now recognized as a potent and independent risk factor for the development of coronary, cerebrovascular and peripheral atherosclerotic disease (Beckman et al., 2002, *JAMA* 287:2570-2581).

Treatment of diabetes can also be effected via the transplantation of insulin-secreting tissue. However, since this latter strategy relies on the use of scarce human tissue as a source, it seems unlikely that there will ever be sufficient numbers of organs available to assist more than a selected number of insulin-dependent diabetics. Furthermore, these patients would have to undergo a long term regimen of immunosuppressive drugs.

Accordingly, there is an ongoing need to develop alternative and more effective methods of regulating glucose levels in diabetic patients. In work leading up to the present invention, a population of cells have been generated which synthesise, store and secrete insulin in response to glucose stimulation. However, whereas existing cell lines of this type have secreted insulin in a highly sensitive manner, and therefore in response to even very low glucose levels, the genetic modification introduced into the cells of the present invention has refined their glucose responsiveness such that insulin is produced only in response to physiologically relevant levels of glucose, that is, levels equal to or greater than the minimum levels of glucose which would result in pancreatic β cell insulin production in normal individuals.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each nucleotide sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention is directed to a genetically modified mammalian cell, which cell is capable of secreting insulin, said genetic modification comprising the transfection of said cell with a nucleic acid molecule encoding pancreatic islet glucokinase.

In another aspect there is provided a genetically modified mammalian hepatocyte, which hepatocyte is capable of secreting insulin, said genetic modification comprising the transfection of said hepatocyte with a nucleic acid molecule encoding pancreatic islet glucokinase.

Yet another aspect of the present invention is directed to a genetically modified mammalian hepatocyte, which hepatocyte is capable of secreting insulin, said genetic modification comprising the transfection of said hepatocyte with a nucleic acid molecule encoding pancreatic islet glucokinase and wherein said cell is responsive to glucose in a physiologically relevant manner.

Still another aspect of the present invention provides a genetically modified human hepatocyte, which hepatocyte is capable of secreting insulin, said genetic modification comprising the transfection of said hepatocyte with a nucleic acid molecule encoding pancreatic islet glucokinase.

Yet still another aspect of the present invention provides a genetically modified human hepatocyte, which hepatocyte is capable of secreting insulin, said genetic modification comprising the transfection of said cell with a vector, which vector comprises a nucleic acid molecule encoding pancreatic islet glucokinase.

Still yet another aspect of the present invention provides a genetically modified Huh7ins cell, said genetic modification comprising the transfection of said Huh7ins cell with a vector, which vector comprises a nucleic acid molecule encoding pancreatic islet glucokinase.

A further aspect of the present invention is directed to a method of therapeutically and/or prophylactically treating a condition in a mammal, which condition is characterised by the aberrant production of functional insulin, said method comprising introducing into said mammal an effective number of the genetically modified cells hereinbefore defined.

Another further aspect of the present invention provides a method of therapeutically and/or prophylactically treating diabetes in a mammal, said method comprising introducing into said mammal an effective number of the genetically modified cells hereinbefore defined.

Still another aspect of the present invention contemplates a method of modulating insulin levels in a mammal said method comprising introducing into said subject an effective number of the genetically modified cells hereinbefore defined.

Yet another aspect of the present invention contemplates a method of modulating glucose levels in a mammal said method comprising introducing into said subject an effective number of the genetically modified cells hereinbefore defined.

Still another aspect of the present invention is directed to the use of genetically modified cells hereinbefore defined in the manufacture of a medicament for the treatment of a condition in a mammal, which condition is characterised by the aberrant production of functional insulin.

According to yet another aspect of the present invention, there is provided a method of assessing the effect of a treatment or culture regime on the phenotypic state of the genetically modified cells as hereinbefore defined, said method comprising subjecting said cells to said treatment regime and screening for an altered phenotypic state.

BRIEF DESCRIPTION OF THE DRAWINGS

FIG. 2 is a schematic representation of the pIERSpuro3 vector sequence of the pIERSpuro3 vector (5157 base pairs sequence SEQ ID NO:1) with insert human islet glucokinase cDNA (2733 base pairs SEQ ID NO:2) highlighted in enlarged text. The nucleotides in bold text represent the remnant nucleotides of the pBluescriptSK cloning vector. SEQ ID NO:3 represents the vector sequence incorporating the islet glucokinase cDNA sequence.

FIG. 8 is a transmission electron micrograph of Melligen cells showing secretory vesicles with dense granules (sg) surrounded by a pale halo (bar=1 µM). (b) Immuno-electron micrographs showing localization of insulin in Melligen cells (bar=460 nm).

FIG. 10 is a graphical representation of the treatment of MIN-6 cells with cytokine concentrations titrated over 8 days a) at twice (IFN-γ (768 ng/mL), TNF-α (20 ng/mL) and IL-1β (4000 pg/mL)) and b) at half (IFN-γ (192 ng/mL), TNF-α (5 ng/mL) and IL-1β (1000 pg/mL)) the initial concentrations used. Results expressed as mean±SE (n=4; SEs fell within data points).

FIG. 19 is an image of the cell morphology of untreated MIN-6 cells following a) 1 day, b) 6 days, and c) 12 days of incubation without cytokines. The cell morphology of MIN-6 cells following cytokine treatment with IFN-γ, TNF-α and IL-1β can be seen in d) 1 day, e) 6 days and f) 12 days. (100× magnification).

FIG. 30 is an image of real-time PCR analysis of (a) Human islet glucokinase in lane 2 human islet cells, lane 3 Melligen cells, lane 4 Huh7ins with vector only, lane 5 Huh7ins, lane 6 Huh7 cells, lane 7 dH$_2$O and (b) human liver glucokinase in lane 2: human islet cells, lane 3: Melligen cells, lane 4: Huh7ins with vector only, lane 5: dH$_2$O. Lane 1: DNA marker in both cases.

FIG. 31 is a graphical representation of real-time PCR expression of liver GK in a) Melligen cells and Huh7ins with empty vector, and b) Huh7ins cells and Huh7ins cells with empty vector. The level of gene expression was expressed as the corrected mean Ct value ±SE of individual cell lines (n=8).

FIG. 34 is a graphical representation of Real-time PCR expression of the glucose transporter GLUT2: in a) Melligen cells and Huh7 cells, and b) Melligen cells and Huh7ins cells. The level of gene expression was expressed as the corrected mean Ct value ±SE of individual cell lines (n=8).

DETAILED DESCRIPTION OF THE INVENTION

Figure 1:
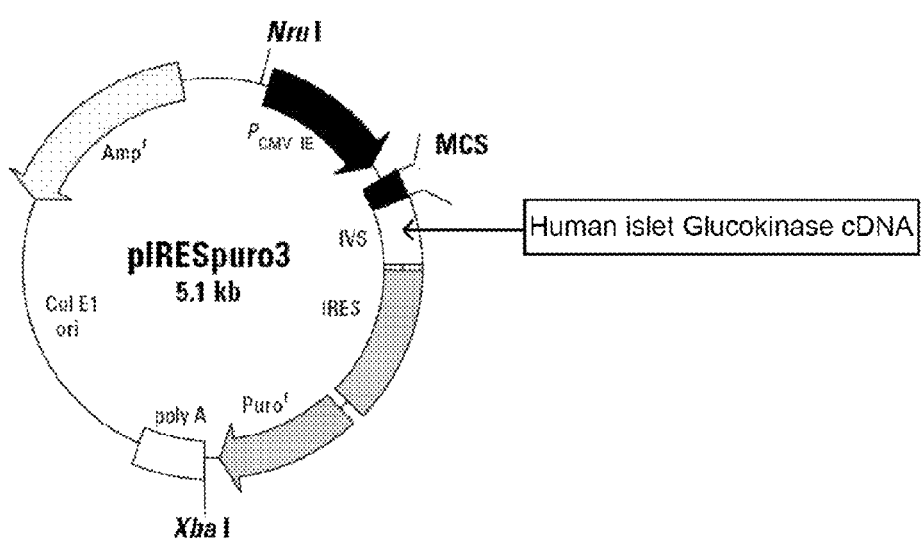
FIG. 1 is a schematic representation of pIRESpuro3. The human islet glucokinase cDNA was cut out of the vector pBluescriptSK at the $Eco_R$ I site and subsequently cloned into the EcoRI site of the multi-cloning site of the pIRESpuro3 vectors.

The present invention is predicated, in part, on the determination that glucose responsive insulin secretion by genetically engineered cells which are not pancreatic cells can be more appropriately designed to mimic normal physiological events by engineering the cell to express pancreatic islet glucokinase, as opposed to other forms of glucokinase. It has been determined that in the absence of the production of this enzyme, hypersensitive responsiveness to extracellular glucose levels can occur, leading to the induction of a hypoglycaemic state in individuals treated with such cells, due to the fact that insulin production is upregulated even where systemic levels of glucose are below the lower physiological threshold required to stimulate insulin production by normal pancreatic β cells. This determination, and the generation of cells based thereon, has now facilitated the improvement of therapeutic and prophylactic treatment regimes directed to treating diabetes and/or the symptoms associated with diabetes.

Accordingly, one aspect of the present invention is directed to a genetically modified mammalian cell, which cell is capable of secreting insulin, said genetic modification comprising the transfection of said cell with a nucleic acid molecule encoding pancreatic islet glucokinase.

Reference to a "cell capable of secreting insulin" should be understood as a reference to a cell which either does or has the capacity to produce insulin. Reference to "produce" is a reference to the expression (being transcription and translation) of an insulin encoding nucleic acid molecule and secretion of the insulin expressed thereby. It should be understood, however, that although the cell may be any type of eukaryotic cell, the cell is not a functionally normal pancreatic β cell. The cell may be one which, even in the absence of the genetic modification of the present invention can nevertheless produce insulin either constitutively or in response to a stimulus or it is one which although not producing insulin prior to incorporation of the genetic modification of the present invention, will be able to do so thereafter.

Without limiting the present invention to any one theory or mode of action, the capacity of a normal pancreatic β cell to produce insulin in a physiologically relevant glucose responsive manner is due both to its capacity to express the insulin gene and to the functionality of a "glucose sensing system" which regulates insulin release in response to small external nutrient changes. The glucose sensing system essentially comprises a high capacity glucose transporter, such as GLUT 2, and a glucose phosphorylation enzyme, such as glucokinase. The latter molecule, which is the subject of the genetic modification of the present invention, provides the crucial cellular functional attribute that ensures that insulin gene expression occurs only in response to extracellular glucose levels which fall within a specific mM range. Without limiting the present invention to any one theory or mode of action, insulin is released into the extracellular environment either via secretion of soluble insulin by the cell or via anchoring of the insulin molecules to cell-surface molecules. It should be understood that following expression of the nucleic acid molecule encoding insulin, the insulin which is produced may be stored intracellularly for a period of time prior to its release. For example, the cell may store insulin intracellularly where, upon glucose stimulation, the stored insulin is released and/or the expression of insulin is up regulated. This cell may therefore constitutively express insulin but effects its secretion only upon receipt of an appropriate stimulus. To this end, the cell which is the subject of the genetic modification of the present invention includes, but is not limited to:

(i) cells which naturally express insulin and a functional glucose sensing system but which require introduction of the pancreatic islet glucokinase gene in order to effect insulin production at physiologically relevant extracellular glucose concentrations (these cells may or may not express an endogenous glucokinase gene which, although functional, does not meet the physiological requirements herein discussed);

(ii) cells which require some form of genetic or cellular manipulation in order to enable insulin production and/or expression of a high capacity glucose transporter. for example, the cell may require manipulation in order to produce and secrete insulin (wherein in its natural state that cell would not produce and/or secrete insulin) or it may require manipulation in order to enable the cell to produce increased levels of insulin (wherein in its natural state that cell would produce and/or secrete lower levels of insulin). Accordingly, this manipulation may be at the level of the insulin gene and/or some other gene required to effect insulin production and secretion, such as a high capacity glucose transporter. Further, the subject manipulation may be at the level of the insulin or glucose transporter protein encoding genes or it may be at the level of a regulatory sequence such as a promoter or enhancer sequence. The subject cell may therefore inherently exhibit functionality at the level of one or more aspects of its insulin production and secretion machinery and may therefore require manipulation only in relation to some but not all aspects of this machinery. For example, the cell may be transfected with a nucleic acid molecule encoding insulin and/or GLUT 2. Even more preferably, the cell is permanently transfected with cDNA or genomic DNA encoding insulin and/or GLUT 2. However, transplantation of cells which transiently express a nucleic acid molecule encoding these molecules may be useful in certain circumstances, for example, where the individual will only temporarily exhibit symptoms of diabetes due to the temporary down regulation of the activity of their β cells. This may be of use, for example, in the treatment of transient conditions such as gestational diabetes. As mentioned earlier, the present invention should also be understood to extend to the use of cells in which, rather than transfecting a nucleic acid molecule encoding insulin into the cell, an endogenous but unexpressed genomic insulin or glucose transporter gene is switched on, that is, expression of the gene is induced or even up-regulated where the gene is not expressed in sufficiently high levels.

In terms of rendering the cell capable of producing and secreting insulin as detailed above, it would be appreciated that this may have occurred at a time point prior to the generation of the cells of the present invention or it may occur simultaneously with the genetic modification of the present invention, being transfection of the cells with a nucleic acid molecule encoding pancreatic islet glucokinase.

The subject cells may have been freshly isolated from an individual (such as an individual who may be the subject of treatment) or they may have been sourced from a non-fresh source, such as from a culture (for example, where cell numbers were expanded) or a frozen stock of cells (for example, an established stem cell line such as the Huh7ins cell line), which had been isolated at some earlier time point either from an individual or from another source. It should also be understood that the subject cells, prior to undergoing the genetic manipulation of the present invention, may have undergone some other form of treatment or manipulation, such as but not limited to enrichment or purification, modification of cell cycle status or the formation of a cell line. Accordingly, the subject cell may be a primary cell or a secondary cell. A primary cell is one which has been isolated from an individual. A secondary cell is one which, following its isolation, has undergone some form of in vitro manipulation prior to the genetic manipulation of the present invention.

In a preferred embodiment, the subject cell is a hepatocyte. Without limiting the present invention to any one theory or mode of action, hepatocytes are known to play a crucial role in intermediary metabolism, synthesis and storage of proteins in the liver. Still further, liver cells inherently express the high capacity glucose transporter GLUT 2, this being one of the key elements of the glucose sensing system which regulates insulin release from pancreatic β cells in response to small external nutrient changes. Accordingly, where hepatocytes are used, other than introducing the genetic modification of the present invention (being the incorporation of a gene expressing pancreatic islet glucokinase) they need generally only otherwise be manipulated to introduce the capacity to express the insulin gene.

The present invention therefore more preferably provides a genetically modified mammalian hepatocyte, which hepatocyte is capable of secreting insulin, said genetic modification comprising the transfection of said hepatocyte with a nucleic acid molecule encoding pancreatic islet glucokinase.

As detailed hereinbefore, it has been determined that expression of a glucokinase, per se, although enabling cellular glucose responsiveness, may not necessarily result in glucose responsiveness which mimics the physiological events associated with normal pancreatic functioning. For example, the glucokinase enzyme which is endogenously expressed by hepatocytes, although arguably acceptable in the context of normal hepatic functioning, is not ideal in the context of pancreatic functioning since it is effectively "hyperresponsive" in that such cells, if transfected with an insulin encoding gene, will be stimulated to express and secrete insulin at extracellular glucose concentrations which are below those at which normal pancreatic islet β cells would produce insulin. In the context of the human, for example, normal pancreatic islet β cells will produce insulin in response to extracellular concentrations of glucose of the order of 4-5 mM while some hepatocytes, if genetically engineered to produce insulin, are responsive to glucose levels well below 4 mM, thereby exhibiting the potential to induce hypoglycaemia if not appropriately managed.

To this end, reference to a genetically modified cell which is responsive to glucose in a "physiologically relevant manner" should be understood as a reference to a cell which produces insulin in response to substantially the same glucose concentration range to which the pancreatic islet β cells of the mammal in issue would normally respond. That is, the subject glucose responsiveness is not such that a physiologically unacceptable state of hypoglycaemia would be induced to occur. It would be appreciated, therefore, that this concentration range may vary from one mammal to another. In the context of the human, the relevant glucose concentration range is about 4-5 mM of glucose. In terms of overcoming this problem, it has been further determined that where a glucose responsive insulin secreting cell is to be generated, the problem associated with glucose hyperresponsiveness can be overcome by designing the cell to express pancreatic islet glucokinase. Cells which have been transfected with the gene encoding this particular form of glucokinase have been found to achieve a physiological responsiveness to extracellular glucose levels which mimics that observed by normal pancreatic islet β cells.

According to this preferred embodiment, the present invention is directed to a genetically modified mammalian hepatocyte, which hepatocyte is capable of secreting insulin, said genetic modification comprising the transfection of said hepatocyte with a nucleic acid molecule encoding pancreatic islet glucokinase and wherein said cell is responsive to glucose in a physiologically relevant manner.

Reference to "pancreatic islet glucokinase" should be understood as a reference to a form of glucokinase which is expressed by pancreatic islet cells. To this end, reference to the proteins which are expressed by the cells of the present invention, such as "insulin", "glucose transporter", "GLUT 2", "glucokinase" and "pancreatic islet glucokinase" should be understood as a reference to all forms of these proteins and to functional derivatives and homologues thereof. This includes, for example, any isoforms which arise from alternative splicing of the mRNA encoding these molecules or functional mutants or polymorphic variants of these proteins. For example, reference to "insulin" should be understood as a reference to all forms of insulin including, but not limited to, precursor forms (for example, proinsulin), split products or partially cleaved proinsulin (for example des 32,33 insulin and des 64,65 insulin), mature insulin (for example, the product obtained following cleavage of proinsulin) the α or β chain of insulin in isolation or various isoforms of insulin due to the translation of mRNA splice variants. For example, the Huh7ins cell line produces pro-insulin as the bioactive product since liver cells do not naturally express the enzymes PC2 or PC3 which cleave proinsulin to insulin. In another example, the pancreatic islet glucokinase is the human form of this molecule and, even more preferably, the form encoded by SEQ ID NO:2.

Reference to "mammal" should be understood to include reference to a mammal such as but not limited to human, primate, livestock (animal (eg. sheep, cow, horse, donkey, pig), companion animal (eg. dog, cat), laboratory test animal (eg. mouse, rabbit, rat, guinea pig, hamster), captive wild animal (eg. fox, deer). Preferably the mammal is a human or primate. Most preferably the mammal is a human.

Accordingly, the present invention more preferably provides a genetically modified human hepatocyte, which hepatocyte is capable of secreting insulin, said genetic modification comprising the transfection of said hepatocyte with a nucleic acid molecule encoding pancreatic islet glucokinase.

Preferably, said pancreatic islet glucokinase is human pancreatic islet glucokinase and, even more preferably, the form encoded by SEQ ID NO:2.

"Derivatives" of the molecules herein described (for example insulin, GLUT 2, glucose transporters in general, glucokinase and the like) include functional fragments, parts, portions or variants. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the functionality of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular regions of the entire protein fused to peptides, polypeptides or other proteinaceous or non-proteinaceous molecules. For example, insulin or derivative thereof may be fused to another molecule in order to agonise its activity. In another example, it may be desirable to facilitate co-expression of both pro-insulin and a cleavage enzyme. Derivatives of nucleic acid sequences which may be utilised in accordance with the method of the present invention may similarly be derived from single or multiple nucleotide substitutions, deletions and/or additions including fusion with other nucleic acid molecules. Derivatives of nucleic acid sequences also include degenerate variants.

A "variant" should be understood to mean a molecule which exhibits at least some of the functional activity of the form of molecule of which it is a variant. A variation may take any form and may be naturally or non-naturally occurring. By "homologue" is meant that the molecule is derived from a species other than that which is being treated in accordance with the method of treatment aspects of the present invention. This may occur, for example, where it is determined that a species other than that which is being treated produces a form of the subject molecule which exhibits suitable functionality. In the context of insulin, for example, one might utilise the insulin gene of a non-human mammal, even where the cells of the invention are proposed to be utilised in a human context.

As detailed hereinbefore, the cells of the present invention are genetically modified. This genetic modification may occur in one or both of two contexts. First, the cell may have been genetically modified in order to render it "capable of secreting insulin". Secondly, the subject cell is also transfected with a nucleic acid molecule encoding pancreatic islet glucokinase. Accordingly, by "genetically modified" is meant that the subject cell has undergone some form of molecular manipulation relative to that which is observed in the context of the majority of a corresponding unmodified population. Such modifications include but are not limited to:

(i) The introduction of homologous or heterologous nucleic acid material to the cell. For example, the cell is rendered transgenic via the introduction of all or part of one or more genes. This clearly occurs in the context of the transfection of a nucleic acid molecule encoding pancreatic islet glucokinase but may also occur to the extent that the cell must be rendered "capable of secreting insulin". The genes which are introduced may encode a protein product, such as insulin, glucokinase or a glucose transporter. Alternatively, the subject gene may correspond to a regulatory molecule such as a promoter, for example where one is merely seeking to modulate the transcription of an existing gene.

Preferably, the cell is transfected with a nucleic acid molecule encoding insulin or a derivative or homologue thereof. Even more preferably, the cell is permanently transfected with cDNA or genomic DNA encoding insulin and/or pancreatic islet glucokinase or a derivative or homologue thereof. However, cells may be generated which transiently express a nucleic acid molecule encoding these molecules. This may be useful in certain circumstances where, for example, an individual will only temporarily exhibit symptoms of diabetes due to the temporary downregulation of the activity of their β cells. This may be of use, for example, in the treatment of transient conditions such as gestational diabetes. In another example, rather than transfecting a nucleic acid molecule encoding these molecules into the cell, an endogenous but unexpressed genomic gene is switched on, that is, expression of the gene is induced or even upregulated where the gene is either not expressed or not expressed in sufficiently high levels.

In addition to the modification of the cells of the present invention to produce proteins which are directly relevant to insulin production, other genes relevant to optimising generation of the subject cells, and which may also be introduced, include genes encoding marker proteins such as EGFP. Selection markers, such as antibiotic resistance genes (for example G418 resistance gene which enables the selection of mammalian cells using the neomycin analogue G418 or puromycin resistance gene), provide a convenient means of selecting for successful transformants while the incorporation of a suicide gene, such as the pMC1-thymidine kinase gene, facilitates the in vivo elimination of the introduced genetically modified cells subsequently to conclusion of the treatment regime. Although this is not likely to be required in the context of treating Type I diabetes, it may be relevant where a transient treatment regime is required such as in the context of gestational diabetes or some milder forms of Type II diabetes.

(ii) The modulation of expression of a gene, for example by inducing upregulation of expression of a gene which would otherwise not be expressed, or the mutation of endogenous DNA, for example to downregulate or render non-functional an unwanted gene, such as the endogenous hepatic glucokinase gene.

Reference to a "nucleic acid" should be understood as a reference to both deoxyribonucleic acid and ribonucleic acid thereof. The subject nucleic acid molecule may be any suitable form of nucleic acid molecule including, for example, a genomic, cDNA or ribonucleic acid molecule. To this end, the term "expression" refers to the transcription and translation of DNA or the translation of RNA resulting in the synthesis of a peptide, polypeptide or protein. A DNA construct, for example, corresponds to the construct which one may seek to transfect into a cell for subsequent expression while an example of an RNA construct is the RNA molecule transcribed from a DNA construct, which RNA construct merely requires translation to generate the protein of interest. Reference to "expression product" is a reference to the product produced from the transcription and translation of a nucleic acid molecule.

The term "protein" should be understood to encompass peptides, polypeptides and proteins. It should also be understood that these terms are used interchangeably herein. The protein may be glycosylated or unglycosylated and/or may contain a range of other molecules fused, linked, bound or otherwise associated to the protein such as lipids, carbohydrates or other peptides, polypeptides or proteins (such as would occur where the protein of interest is produced as a fusion protein with another molecule, for example GST or EGFP). Reference hereinafter to a "protein" includes a protein comprising a sequence of amino acids as well as a protein associated with other molecules such as amino acids, lipids, carbohydrates or other peptides, polypeptides or proteins.

It would be appreciated by the person of skill in the art that the mechanism by which these genetic modifications are introduced may take any suitable form which would be well known and understood by those of skill in the art. For example, genetic material is generally conveniently introduced to cells via the use of an expression construct. Alternatively, one may seek to use, as the starting cellular population, a cell type which either naturally or as a result of earlier random or directed genetic manipulation is characterised by one or more of the genetic modifications of interest (for example, one may seek to introduce the pancreatic islet glucokinase modification into a cell which has previously been modified in terms of rendering it "capable of secreting insulin". The modification of a cell line such as Huh7ins, as discussed in more detail hereinafter, which is a hepatic cell line transfected with insulin encoding DNA is one such example).

Most preferably, said genetic modification is the transfection of a cell capable of secreting insulin with an expression construct comprising one or more DNA regions comprising a promoter operably linked to a sequence encoding a pancreatic islet glucokinase and, optionally, a second DNA region encoding a selectable marker and, optionally, a third DNA region encoding a suicide protein. In another preferred embodiment, the construct may also comprise DNA encoding insulin and/or a glucose transporter where the subject cell has not previously been rendered "capable of secreting insulin".

The subject promoter may be constitutive or inducible. Where the subject construct expresses more than one protein of interest, these may be under the control of separate promoters or they may be under the control of a single promoter, such as occurs in the context of a bicistronic vector which makes use of an IRES sequence to facilitate the translation of more than one protein product, in an unfused form, from a single RNA transcript. The subject construct may additionally be designed to facilitate use of the Cre recombinase mediated splicing inducible gene expression system.

Reference to a nucleic acid "expression construct" should be understood as a reference to a nucleic acid molecule which is transmissible to a cell and designed to undergo transcription. The RNA molecule is then transcribed therefrom. In general, expression constructs are also referred to by a number of alternative terms, which terms are widely utilised interchangeably, including "expression cassette" and "vector".

The expression construct of the present invention may be generated by any suitable method including recombinant or synthetic techniques. To this end, the subject construct may be constructed from first principles, as would occur where an entirely synthetic approach is utilised, or it may be constructed by appropriately modifying an existing vector. Where one adopts the latter approach, the range of vectors which could be utilised as a starting point are extensive and include, but are not limited to:

(i) Plasmids

Plasmids are small independently replicating pieces of cytoplasmic DNA, generally found in prokaryotic cells, which are capable of autonomous replication. Plasmids are commonly used in the context of molecular cloning due to their capacity to be transferred from one organism to another. Without limiting the present invention to any one theory or mode of action, plasmids can remain episomal or they can become incorporated into the genome of a host. Examples of plasmids which one might utilise include the bacterial derived pBR322 and pUC.

(ii) Bacteriophage

Bacteriophages are viruses which infect and replicate in bacteria. They generally consist of a core of nucleic acid enclosed within a protein coat (termed the capsid). Depending on the type of phage, the nucleic acid may be either DNA (single or double stranded) or RNA (single stranded) and they may be either linear or circular. Phages may be filamentous, polyhedral or polyhedral and tailed, the tubular tails to which one or more tubular tail fibres are attached. Phages can generally accommodate larger fragments of foreign DNA than, for example, plasmids. Examples of phages include, but are not limited to the *E. coli* lambda phages, P1 bacteriophage and the T-even phages (e.g. T4).

(iii) Baculovirus

These are any of a group of DNA viruses which multiply only in invertebrates and are generally classified in the family Baculoviridae. Their genome consists of double-stranded circular DNA.

(iv) Artificial Chromosomes

Artificial chromosomes such as yeast artificial chromosomes or bacterial artificial chromosomes.

(v) Hybrid vectors such as cosmids, phagemids and phasmids

Cosmids are generally derived from plasmids but also comprise cos sites for lambda phage while phagemids represent a chimaeric phage-plasmid vector. Phasmids generally also represent a plasmid-phage chimaera but are defined by virtue of the fact that they contain functional origins of replication of both. Phasmids can therefore be propagated either as a plasmid or a phage in an appropriate host strain.

(vi) Commercially available vectors which are themselves entirely synthetically generated or are modified versions of naturally occurring vectors, such as the pIRE-Spuro3 bicistronic vector.

It would be understood by the person of skill in the art that the selection of an appropriate vector for modification, to the extent that one chooses to do this rather than synthetically generate a construct, will depend on a number of factors including the ultimate use to which the genetically modified cell will be put. For example, where the cell is to be administered in vivo into a human, it may be less desirable to utilise certain types of vectors, such as viral vectors. Further, it is necessary to consider the amount of DNA which is sought to be introduced to the construct. It is generally understood that certain vectors are more readily transfected into certain cell types. For example, the range of cell types which can act as a host for a given plasmid may vary from one plasmid type to another. In still yet another example, the larger the DNA insert which is required to be inserted, the more limited the choice of vector from which the expression construct of the present invention is generated. To this end, the size of the inserted DNA can vary depending on factors such as the size of the DNA sequence encoding the protein of interest, the number of proteins which are sought to be expressed, the number of selection markers which are utilised and the incorporation of features such as linearisation polylinker regions and the like.

The expression construct which is used in the present invention may be of any form including circular or linear. In this context, a "circular" nucleotide sequence should be understood as a reference to the circular nucleotide sequence portion of any nucleotide molecule. For example, the nucleotide sequence may be completely circular, such as a plasmid, or it may be partly circular, such as the circular portion of a nucleotide molecule generated during rolling circle replication (this may be relevant, for example, where a construct is being initially replicated, prior to its introduction to a cell population, by this type of method rather than via a cellular based cloning system). In this context, the "circular" nucleotide sequence corresponds to the circular portion of this molecule. A "linear" nucleotide sequence should be understood as a reference to any nucleotide sequence which is in essentially linear form. The linear sequence may be a linear nucleotide molecule or it may be a linear portion of a nucleotide molecule which also comprises a non-linear portion such as a circular portion. An example of a linear nucleotide sequence includes, but is not limited to, a plasmid derived construct which has been linearised in order to facilitate its integration into the chromosomes of a host cell or a construct which has been synthetically generated in linear form. To this end, it should also be understood that the configuration of the construct of the present invention may or may not remain constant. For example, a circular plasmid-derived construct may be transfected into a cell where it remains a stable circular episome which undergoes replication and transcription in this form. However, in another example, the subject construct may be one which is transfected into a cell in circular form but undergoes intracellular linearisation prior to chromosomal integration. This is not necessarily an ideal situation since such linearisation may occur in a random fashion and potentially cleave the construct in a crucial region thereby rendering it ineffective.

The nucleic acid molecules which are utilised in the method of the present invention are derivable from any human or non-human source. Non-human sources contemplated by the present invention include primates, livestock animals (eg. sheep, pigs, cows, goats, horses, donkeys), laboratory test animal (eg. mice, hamsters, rabbits, rats, guinea pigs), domestic companion animal (eg. dogs, cats), birds (eg. chicken, geese, ducks and other poultry birds, game birds, emus, ostriches) captive wild or tamed animals (eg. foxes, kangaroos, dingoes), reptiles, fish, insects, prokaryotic organisms or synthetic nucleic acids.

It should be understood that the constructs of the present invention may comprise nucleic acid material from more than one source. For example, whereas the construct may originate from a bacterial plasmid, in modifying that plasmid to introduce the features defined herein nucleic acid material from non-bacterial sources may be introduced. These sources may include, for example, viral DNA (e.g. IRES DNA), mammalian DNA (e.g. the DNA encoding the pancreatic islet glucokinase) or synthetic DNA (e.g. to introduce specific restriction endonuclease sites). Still further, the cell type in which it is proposed to express the subject construct may be different again in that it does not correspond to the same organism as all or part of the nucleic acid material of the construct. For example, a construct consisting of essentially bacterial and viral derived DNA may nevertheless be expressed in the mammalian stem cells contemplated herein.

Without limiting the present invention to any one theory or mode of action, the present invention is exemplified in the context of a pancreatic islet glucokinase expressing bicistronic vector which is transfected into cells which are already "capable of secreting insulin" in the context of the earlier definition. Specifically, cDNA encoding pancreatic islet glucokinase is transfected into the multicloning site of pIRESpuro3. Still without limiting the invention in any way, the pIRESpuro3 bicistronic vector exemplified herein contains the internal ribosome entry site of the encephalomyocarditis virus, which permits the translation of two open reading frames from one messenger RNA (Jackson et al., 1990, *Trends Biochem. Sci.* 15:477-483; Jang et al., 1988, *J. Virol.* 62:2636-2643; Rees et al., 1996, *BioTechniques* 20:102-104). After selection with puromycin, most surviving colonies are likely to stably express the pancreatic islet glucokinase, thus decreasing the need to screen large numbers of colonies to find functional clones (this being a particular advantage of bicistronic vectors). To select for cells that express high levels of pancreatic islet glucokinase, the selective pressure for antibiotic resistance is increased due to the positioning of the puromycin resistance gene downstream to a less optimal position for translation as directed by the IRES sequence (Rees et al., 1996, supra). By decreasing the level of expression of the antibiotic resistance marker, the selective pressure on the entire expression cassette is increased, resulting in selection for cells that express the entire transcript, including the pancreatic islet glucokinase, at high levels. The expression cassette of pIRESpuro3 contains the human cytomegalovirus major immediate early promoter/enhancer followed by a multiple cloning site that precedes stop codons in all three reading frames, a synthetic intron known to enhance the stability of the mRNA (Huang and Gorman, 1990, *Nucleic Acids Res.* 18:937-947), the ECMV IRES followed by the gene encoding puromycin resistance (puromycin-N-acetyl-transferase; de la Luna, et al., 1988, *Gene* 62:121-128), and the polyadenylation signal from SV40. Ribosomes can enter the bicistronic mRNA at the 5' end to translate the gene of interest and at the ECMV IRES to translate the antibiotic resistance marker. It should be understood that the expression vector exemplified herein is provided solely by way of example and is in no way intended to limit the range and design of vectors which could be used to achieve the object of the present invention.

The present invention therefore more preferably provides a genetically modified human hepatocyte, which hepatocyte is capable of secreting insulin, said genetic modification comprising the transfection of said cell with a vector, which vector comprises a nucleic acid molecule encoding pancreatic islet glucokinase.

Preferably, said vector is a bicistronic vector and said pancreatic islet glucokinase is the form encoded by SEQ ID NO:2.

Even more preferably, said bicistronic vector is pIRE-Spuro3 and most preferably defined by SEQ ID NO:3.

Still more preferably, said genetically modified cell is responsive to glucose in a physiologically relevant manner and, most preferably, to extracellular glucose levels in the range of 3-8 mM, preferably 3.5-7 mM, more preferably 4-6 mM and most preferably 4-5 mM.

As would be appreciated by the person of skill in the art, the generation of the cells of the present invention may require the application of a screening and selection step to identify and isolate cells which have successfully incorporated the genetic modification of interest. Identification methods would be well known to the person of skill in the art and include, but are not limited to:

(i) Detection of specific cellular proteins.
Detection of specific proteins, such as cell surface proteins or intracellular proteins (eg. insulin, GLUT 2, glucokinase etc.), may be conveniently effected via fluorescence affinity labelling and fluorescence microscopy, for example. Briefly, fluorescently labelled antibodies are incubated on fixed cells to detect specific cardiac markers. Alternatively, techniques such as Western immunoblotting or hybridization micro arrays ("protein chips") may be employed. In this regard, this method can be utilised to identify cell types via either a positive or negative selection step based on the expression of any one or more molecules.

(ii) Detection of specific cellular RNA or DNA.
This method is preferably effected using RT-PCR or real-time (qRT-PCR). Alternatively, other methods, which can be used include hybridization microarray ("RNA chip") or Northern blotting or Southern blotting. RT-PCR can be used to detect specific RNAs encoding essentially any protein, such as the proteins detailed in point (ii) above, or proteins which are secreted or otherwise not conveniently detectable via the methodology detailed in point (ii).

(iii) Detection of specific cellular functional activity.
Although the analysis of a cell population in terms of its functioning is generally regarded as a less convenient method than the screening methods of points (i)-(ii), in some instances this may not be the case. For example, to the extent that one is seeking to establish the existence of a functional glucose sensing system, the insulin output of a cell of the invention in the presence of varying extracellular glucose levels may be assessed.

(iv) Other means of screening for the stable integration and maintenance of the modification (for example in the context of cell line generation and therefore long term cellular culturing) may be performed include screening for the expression of a selection marker, such as EGFP, which provides a most convenient means for establishing the integration of a genetic modification, in particular where marker expression is inextricably linked to the modification of interest, such as via the use of a bicistronic vector.

It should be understood that in terms of characterising the population of cells generated in the context of the present invention, any one or more of the techniques detailed above may be utilised.

As detailed hereinbefore, the modified cell of the present invention is preferably a hepatocyte, this being a cell type which arguably requires less modification to render it capable of secreting insulin than other cell types due to the fact that it inherently expresses the high capacity glucose transporter, GLUT 2. However, although hepatocytes also inherently express glucokinase, in the context of insulin responsiveness, this molecule arguably functions in a hypersensitive manner in that it results in the expression of a transfected insulin gene at extracellular glucose levels of as low as 2.5 mM, this being below the physiological range that pancreatic islet cells generally produce insulin in the human. Accordingly, the developments of the present invention are a significant step forward in that they overcome this problem.

In accordance with this preferred embodiment, the subject hepatocyte may be freshly harvested or it may be derived from a cell line. Still further, it may be one which is required to be made capable of secreting insulin via transfection of the DNA encoding insulin (this occurring either separately to or concomitantly with the pancreatic islet glucokinase genetic modification herein described) or it may already have been rendered so. Preferably, said hepatocyte is a Huh7ins cell, this being a cell line which has been modified to express a nucleic acid molecule encoding insulin. Without limiting the present invention to any one theory or mode of action, Huh7ins is a genetically engineered liver cell line which stores and secretes insulin in response to glucose. However, these cells are hyperresponsive in the physiological sense in that they can commence secreting insulin at sub-physiological levels of glucose (eg. 2.5 mM), as compared to between 4-5 mM of glucose for normal human pancreatic β cell functioning, thereby potentially leading to the onset of hypoglycaemia. It is thought that these cells exhibit an imbalance in the glucokinase:hexokinase ratio in favour of hexokinases which results in enhanced glycolytic flux at low glucose levels and consequently increased sensitivity of the glucose-stimulated insulin secretion response. To this end, it has been unexpectedly determined that although there exists a functional endogenous glucokinase gene in hepatocytes such as Huh7ins the introduction of the pancreatic glucokinase gene nevertheless acts to overcome the problem associated with the endogenous hepatocyte glucokinase gene activity.

The present invention therefore most preferably provides a genetically modified Huh7ins cell, said genetic modification comprising the transfection of said Huh7ins cell with a vector, which vector comprises a nucleic acid molecule encoding pancreatic islet glucokinase.

Preferably, said vector is a bicistronic vector and said pancreatic islet glucokinase is the form encoded by SEQ ID NO:2.

Even more preferably, said bicistronic vector is pIRE-Spuro3 and most preferably is SEQ ID NO:3.

Still more preferably, said genetically modified Huh7ins cell is a Melligen cell.

The development of the method of the present invention has now facilitated the development of means for therapeutically or prophylactically treating disease conditions characterised by aberrant, preferably insufficient or inadequate, production of functional insulin. This problem may be due to any one of a number of causes including, but not limited to, pancreatic β cell destruction, the aberrant functioning of the β cell glucose sensing system, defects in insulin gene expression or defects in the functionality of the insulin expression product itself. Accordingly, reference to a disease condition "characterised by aberrant production of functional insulin" should be understood as a reference to any condition, a symptom or cause of which is insufficient or inadequate levels of functionally effective insulin. Accordingly, and as detailed above, this may be due to defects in the β cell itself, the glucose sensing system or the expression levels or functionality of the insulin expression product.

Accordingly, another aspect of the present invention is directed to a method of therapeutically and/or prophylactically treating a condition in a mammal, which condition is characterised by the aberrant production of functional insulin, said method comprising introducing into said mammal an effective number of the genetically modified cells hereinbefore defined.

Preferably, said condition is diabetes.

The present invention therefore more particularly provides a method of therapeutically and/or prophylactically treating diabetes in a mammal, said method comprising introducing into said mammal an effective number of the genetically modified cells hereinbefore defined.

Reference to "diabetes" should be understood as a reference to a condition in which insufficient levels of insulin are produced to maintain biologically normal glucose levels. This may be due to congenital defects in the pancreatic islet cells, the onset of an autoimmune response directed to the pancreatic β cells (for example type 1 diabetes/IDDM, gestational diabetes or slowly progressive IDDM which is also referred to as latent autoimmune diabetes in adults), defects in the functioning of the pancreatic islet cells caused by environmental factors such as diet or stress (for example type 2 diabetes/adult onset diabetes), damage to the pancreatic islet cells such as, but not limited to, as caused by physical injury, the degeneration of pancreatic islet cells due to non autoimmune conditions or as a side effect due to the onset or treatment of an unrelated disease condition.

In a related aspect of the present invention, the subject undergoing treatment or prophylaxis may be any human or animal in need of therapeutic or prophylactic treatment. In this regard, reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

The present invention should therefore be understood to encompass preventing, reducing or otherwise ameliorating diabetes in a mammal. This should be understood as a reference to the prevention, reduction or amelioration of any one or more symptoms of diabetes via the production of insulin. Symptoms of diabetes include, but are not limited, to abnormal glucose levels or glucose level regulation, abnormal insulin levels, thirst, frequent urination, weight loss, blurred vision, headache and abdominal pain. It should be understood that the method of the present invention may either reduce the severity of any one or more symptoms or eliminate the existence of any one or more symptoms. For example, the method of the present invention may either fully or partially normalise glucose levels in a diabetic individual. Although complete normalisation is most desirable, partial normalisation is nevertheless useful, for example, to reduce the risk of a type I diabetic individual succumbing to a diabetic coma. The method of the present invention extends to preventing the onset of any one or more symptoms of diabetes. For example, in individuals who are predisposed to the development of diabetes, whose pancreatic islet cells are gradually degenerating or who have suffered acute and irreparable injury to pancreatic islet cells, the method of the present invention may be employed to restore insulin production prior to the occurrence of any one or more symptoms of diabetes.

In accordance with this aspect of the invention, the subject cells are preferably autologous cells which are isolated and genetically modified ex vivo and transplanted back into the individual from which they were originally harvested. However, it should be understood that the present invention nevertheless extends to the use of cells derived from any other suitable source where the subject cells exhibit the same major histocompatability profile as the individual who is the subject of treatment. Accordingly, such cells are effectively autologous in that they would not result in the histocompatability problems which are normally associated with the transplanting of cells exhibiting a foreign MHC profile. Such cells should be understood as falling within the definition of "autologous". For example, under certain circumstances it may be desirable, necessary or of practical significance that the subject cells are isolated from a genetically identical twin, or from an embryo generated using gametes derived from the subject individual or cloned from the subject individual (in this case the cells are likely to correspond to stem cells which have undergone directed differentiation to an appropriate somatic cell type). The cells may also have been engineered to exhibit the desired major histocompatability profile. The use of such cells overcomes the difficulties which are inherently encountered in the context of tissue and organ transplants.

However, where it is not possible or feasible to isolate or generate autologous cells, it may be necessary to utilise allogeneic cells. "Allogeneic" cells are those which are isolated from the same species as the subject being treated but which exhibit a different MHC profile. Although the use of such cells in the context of therapeutics would likely necessitate the use of immunosuppression treatment, this problem can nevertheless be minimised by use of cells which exhibit an MHC profile exhibiting similarity to that of the subject being treated, such as a cell population which has been isolated/generated from a relative such as a sibling, parent or child. Also contemplated herein is the use of established cell lines such as Huh7ins or the Melligen cells which have been derived therefrom. The present invention should also be understood to extend to xenogeneic transplantation. That is, the cells which are genetically modified in accordance with the method of the invention and introduced into a patient are isolated from a species other than the species of the subject being treated.

Reference to an "effective number" means that number of cells necessary to at least partly attain the desired effect, or to delay the onset of, inhibit the progression of, or halt altogether the onset or progression of the particular condition being treated. Such amounts will depend, of course, on the particular condition being treated, the severity of the condition and individual patient parameters including age, physical conditions, size, weight, physiological status, concurrent treatment, medical history and parameters related to the disorder in issue. One skilled in the art would be able to determine the number of cells of the present invention that would constitute an effective dose, and the optimal mode of administration thereof without undue experimentation, this latter issue being further discussed hereinafter. These factors are well known to those of ordinary skill in the art and can be addressed with no more than routine experimentation. It is preferred generally that a maximal cell number be used, that is, the highest safe number according to sound medical judgement. It will be understood by those of ordinary skill in the art, however, that a lower cell number may be administered for medical reasons, psychological reasons or for any other reasons.

As hereinbefore discussed, it should also be understood that although the method of the present invention is predicated on the introduction of genetically modified cells to an individual suffering a condition as herein defined, it may not necessarily be the case that every cell of the population introduced to the individual will have acquired or will maintain the subject modification. For example, where a transfected and expanded cell population is administered in total (i.e. the successfully modified cells are not enriched for), there may exist a proportion of cells which have not acquired or retained the genetic modification. The present invention is therefore achieved provided the relevant portion of the cells thereby introduced constitute the "effective number" as defined above. However, in a particularly preferred embodiment the population of cells which have undergone differentiation will be subjected to the identification of successfully modified cells, their isolation (for example by EGFP based FACS sorting or GST selection) and testing for a functional genetic modification and introduction to the subject individual. This provides a means for selecting a specific subpopulation of cells for administration, such as cells expressing appropriate levels of the insulin and glucose sensing molecules in issue.

In the context of this aspect of the present invention, the subject cells require introduction into the subject individual. To this end, the cells may be introduced by any suitable method. For example, cell suspensions may be introduced by direct injection or inside a blood clot whereby the cells are immobilised in the clot thereby facilitating transplantation. The cells may also be encapsulated prior to transplantation. Encapsulation is a technique which is useful for preventing the dissemination of cells which may continue to proliferate (i.e. exhibit characteristics of immortality), although this is not expected to be a significant problem where a pure population of terminally differentiated cells are administered (but may be an issue if the cell population is derived from an immortalised cell line) or for minimising tissue incompatibility rejection issues.

The cells may also be introduced by surgical implantation. This may be necessary, for example, where the cells exist in the form of a tissue graft or where the cells are encapsulated prior to transplanting. The site of transplant may be any suitable site, for example, subcutaneously or, where the donor cells are liver cells, under the renal capsule. Without limiting the present invention to any one theory or mode of action, where cells are administered as an encapsulated cell suspension, the cells will coalesce into a mass. It should also be understood that the cells may continue to divide following transplantation.

The cells which are administered to the patient can be administered as single or multiple doses by any suitable route. Preferably, and where possible, a single administration is utilised. Administration via injection can be directed to various regions of a tissue or organ, depending on the type of treatment required.

In accordance with the method of the present invention, other proteinaceous or non-proteinaceous molecules may be coadministered either with the introduction of the insulin-producing cells or during insulin production by the transplanted cells. By "coadministered" is meant simultaneous administration in the same formulation or in different formulations via the same or different routes or sequential administration via the same or different routes. By "sequential" administration is meant a time difference of from seconds, minutes, hours or days between the transplantation of these cells and the administration of the proteinaceous or non-proteinaceous molecules or the onset of insulin production and the administration of the proteinaceous or non-proteinaceous molecule. For example, it may be necessary to co-administer the enzyme PC2 or PC3 to facilitate cleavage of proinsulin to insulin. Other examples of circumstances in which such co-administration may be required include, but are not limited to:

(i) When administering non-syngeneic cells or tissues to a subject, there usually occurs immune rejection of such cells or tissues by the subject. In this situation it would be necessary to also treat the patient with an immunosuppressive regimen, preferably commencing prior to such administration, so as to minimise such rejection. Immunosuppressive protocols for inhibiting allogeneic graft rejection, for example via administration of cyclosporin A, immunosuppressive antibodies, and the like are widespread and standard practice.

(ii) Depending on the nature of the condition being treated, it may be necessary to maintain the patient on a course of medication to alleviate the symptoms of the condition until such time as the transplanted cells become integrated and fully functional (for example, the administration of insulin). Alternatively, at the time that the condition is treated, it may be necessary to commence the long term use of medication to prevent re-occurrence of the damage. For example, where the subject damage was caused by an autoimmune condition, the ongoing use of immunosuppressive drugs may be required even when syngeneic cells have been used. This will depend, however, on the nature of the cells which have been genetically modified and whether or not they would correspond to an autoimmune target.

It should also be understood that the method of the present invention can either be performed in isolation to treat the condition in issue or it can be performed together with one or more additional techniques designed to facilitate or augment the subject treatment. These additional techniques may take the form of the co-administration of other proteinaceous or non-proteinaceous molecules, as detailed hereinbefore.

Although the method of the present invention is particularly suited to the treatment or prophylaxis of diabetes, it is not to be understood as being limited to the treatment of this condition. Rather, the method of the present invention can be utilised to treat any condition characterised by aberrant, unwanted or otherwise inappropriate functional activity or levels of a molecule which is directly or indirectly modulatable by insulin, such as but not limited to, the levels of glucose and/or insulin or derivative or equivalent thereof. Reference to "aberrant, unwanted or otherwise inappropriate" functional activity or levels of such a molecule (for example, glucose and/or insulin) should be understood as a reference to either permanently or transiently abnormal levels or activities of these molecules or to physiologically normal levels or activities of one or both of these molecules, which levels or activities are nevertheless unwanted or otherwise inappropriate.

It should be understood that a molecule which is "directly" modulatable by insulin is one which the subject insulin associates or otherwise interacts with to up-regulate, down-regulate or otherwise modulate its functional activity or levels or to in any way alter its structural or other phenotypic, molecular or other physical features. Increasing insulin levels, per se, should be understood to fall within the context of this definition. A molecule which is "indirectly" modulatable by insulin is one which is modulated (in the context described above) by a proteinaceous or non-proteinaceous molecule other than insulin, which other proteinaceous or non-proteinaceous molecule is directly or indirectly modulated by said insulin. Accordingly, the present invention extends to the modulation of the functional activity or levels of a given molecule via an insulin induced cascade of regulatory steps.

Another aspect of the present invention contemplates a method of modulating insulin levels in a mammal said method comprising introducing into said subject an effective number of the genetically modified cells hereinbefore defined.

Yet another aspect of the present invention contemplates a method of modulating glucose levels in a mammal said method comprising introducing into said subject an effective number of the genetically modified cells hereinbefore defined.

Still another aspect of the present invention is directed to the use of genetically modified cells hereinbefore defined in the manufacture of a medicament for the treatment of a condition in a mammal, which condition is characterised by the aberrant production of functional insulin.

Preferably, said condition is diabetes.

The development of the cells of the present invention has now facilitated the development of in vitro based screening systems for testing the effectiveness and toxicity of existing or potential treatment or culture regimes.

Thus, according to yet another aspect of the present invention, there is provided a method of assessing the effect of a treatment or culture regime on the phenotypic state of the genetically modified cells as hereinbefore defined, said method comprising subjecting said cells to said treatment regime and screening for an altered phenotypic state.

By "altered" is meant that one or more of the phenotypic or functional parameters which are the subject of analysis are changed relative to untreated cells. This may be a desirable outcome where the treatment regime in issue is designed to improve or assist cellular functioning. However, where the treatment regime is associated with a detrimental outcome, this may be indicative of toxicity and therefore the unsuitability for use of the treatment regime. It is now well known that the differences which are observed in terms of the responsiveness of an individual to a particular drug are often linked to the unique genetic makeup of that individual. Accordingly, the method of the present invention provides a valuable means of testing either an existing or a new treatment regime which may be used concurrently with the administration of the cells of the invention. This provides a unique means for evaluating the likely effectiveness of a drug, such as a drug which is proposed to be co-administered with the cells of the invention, prior to administering the drug and the cells in vivo. Where a patient is extremely unwell, the physiological stress which can be caused by a treatment regime which causes an unwanted outcome can be avoided or at least minimised.

Accordingly, this aspect of the present invention provides a means of optimising a treatment regime.

Hence the method of the present invention can be used to screen and/or test drugs, other treatment regimes or culture conditions. In the context of assessing phenotypic or functional changes, this aspect of the present invention can be utilized to monitor for changes to the gene expression profiles of the subject cells and tissues. Thus, the method according to this aspect of the present invention can be used to determine, for example, gene expression pattern changes in response to a proposed concomitant treatment regime, such as a treatment regime which is required to be maintained in order to treat an unrelated condition from which the patient also suffers.

Preferably, the treatment to which the cells or tissues of the present invention are subjected is the exposure to a compound. Preferably, the compound is a drug or a physiological ion. Alternatively the compound can be a growth factor or differentiation factor. To this end, it is highly desirable to have available a method which is capable of predicting such side effects on the cells of the invention prior to their exposure to the drug.

The present invention is further defined by the following non-limiting Examples.

Example 1

Generation and Testing of Melligen Cells

Materials and Methods
Plasmid Construct

Human islet glucokinase cDNA contained in the pBluescript commercial vector, was a gift from Dr M. Alan Permutt, the University of Washington (St Louis, USA). The human islet glucokinase cDNA was cut out of the pBrescript SK+ by restriction enzyme $E_{COR}$ I. The 2733 base pair fragment containing the human islet glucokinase cDNA was inserted into the pIERSpuro3 expression vector (Clontech, USA) at the $E_{COR}$ I site in the multi cloning site (971-972 bp) (FIG. 1).

Cell Culture

Huh7ins cells were cultured as monolayers in Dulbecco's Modification of Eagles's Medium containing 10% fetal calf serum (FCS) in 5% $CO_2$ in air plus 0.55 mg/ml G418 as described (Tuch et al., 2003, *Gene Therapy* 10:490-503).

Transfection of Plasmid with Human Islet Glucokinase cDNA

Huh7ins cells were transfected with the pIRESpuro3-glucokinase construct or the pIRESpuro3 vector alone using Effectenen transfection reagent (Qiagen Germany). Twenty four hours after transfection the eukaryocidal antibiotic puromycin (1.1 μg/ml) was added to the cultures. Medium plus drugs were changed every 2-3 days. After 14 days of selection, colonies were picked up and expanded into mass cultures. The cells containing the pIRESpuro3-glucokinase construct will hereafter be referred to as Melligen cells.

Human Islet Glucokinase cDNAs Identification

Total RNA was isolated from clonal cell lines using the Triazol™ method according to the manufacturer's instructions (Gibco-BRL). The RNA sample was treated with DNase in 20 m Tris-HCl (pH 8.4), 2 mM $MgCl_2$, and 50 mM KCl to remove any traces of contaminating genomic DNA. cDNA was synthesised using a transcription kit (Qiagen, Germany). The RT-PCR was undertaken in a volume of 30

μl of buffer containing 50 mM KCl, 10 mM Tris-HCl, 3.5 mM $MgCl_2$, 200 μM each dNTPs, 0.4 μM of the primers and 0.5 ug cDNA.

The primers designed for human islet glucokinase cDNA were as follows:

5'-CTGAGTGGCTTGTGATTCTG-3' (SEQ ID NO:4);
5'-AATCTTAGGTTGGGCATGG-3' (SEQ ID NO:5), which yields a 220 bp product (2461-2681 base pairs).

Figure 3:
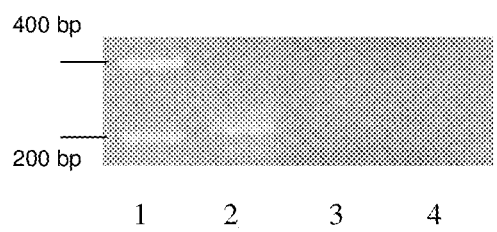
FIG. 3 is an image of the RT/PCR expression of human islet glucokinase, 220 bp product. DNA marker (lane 1), Melligen cells clone 6 (lane 2), Huh7ins cells with pIRISpuro3 vector only (lane 3), Huh7ins cells (lane 4).

Amplification was undertaken for 35 cycles at denaturing temperature 95° C. for 45 seconds, annealing temperature 56° C. for 30 seconds and extension temperature 72° C. for 35 seconds. The PCR product was separated on 2% agarose gel with TBE buffer (FIG. 3).

Western Blot Analysis

Melligen cells, Huh7ins with empty vector and Huh7ins cells were trypsinised and removed from tissue flasks. The suspended cells were centrifuged at 1000 rpm for 5 minutes and supernatant was aspirated. The cell pellets were suspended with buffer I (Tris 10 mM, $NaH_2PO_4$ 20 mM, EDTA 1.0 mM, PMSF 0.1 mM, pepstatin 10 μg/ml, leupeptin 10 μl/ml at pH=7.8) and applied the freeze (−70° C., 10 minutes)-thaw (37° C., 10 minutes) cycle three times, then incubated for 20 minutes at 4° C. Supernatants were prepared by centrifugation at 11,000 rpm in a refrigerate microfuge for 30 minutes and the protein concentration in supernatant was subsequently determined using the Micro BCA protein Assay Reagent Kit (PIERCE).

Protein samples from the three different cell types (15 μg/30 μl) were run on 10% polyacrylamide gels for Western blot analysis at 100 v and then transferred to a nitrocellulose membrane (Millipore Corporation, USA). The nitrocellulose membrane was blocked in phosphate buffered saline (PBS) with 5% skim milk overnight at 4° C. to avoid any non-specific binding. After washing three times (10 min) with PBS containing 0.05% $Tween_{20}$. The nitrocellulose membrane was incubated with primary antibody—rabbit anti-human glucokinase antibody (1/1000 dilution) (Santa Cruz Biot USA) for 2 hours at room temperature, then washed again three times with PBS (0.05% $Tween_{20}$), the nitrocellulose membrane was incubated with second antibody—a polyclonal (donkey) anti-rabbit horseradish peroxidase IgG conjugate (1/800 dilution) (Sigma) for 1 hour at room temperature. After washing three times with PBS (0.05% $Tween_{20}$), glucokinase protein expression in the nitrocellulose membrane was detected using 3,3'-Diaminobenzidine (peroxidase substrate) (Sigma). The primary human glucokinase was raised in rabbits against a recombinant protein corresponding to amino acids 318-405 mapping near the carboxy terminus of glucokinase of human origin, conjugated to a monoclonal anti-rabbit IgG antibody and detects a protein of 52 kD (FIG. 4).

Glucokinase and Hexokinase Enzyme Activity

Glucose phosphorylation was measured in cell homogenates by following the conversion of [U-$^{14}$C] glucose to [U-$^{14}$C] glucose-6-phosphate as described (Kuwajima et al., 1996, *J Biol. Chem.* 261: 8849-53). Glucokinase and hexokinase activities were discriminated by performing the assay in the presence or absence of 10 mmol/L glucose-6-phosphate, an inhibitor of low $K_m$ hexokinase activity (Wilson, 1984, Regulation of carbohydrate metabolism, p. 45-85).

Figure 4:
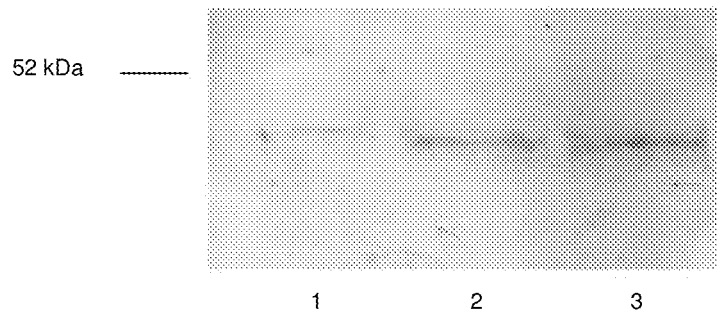
FIG. 4 is an image of a Western blot analysis for human glucokinase in Huh7ins (lane 1), Huh7ins cells with pIRISpuro3 vector only (lane 2), Melligen cells (lane 3).
Figure 5:
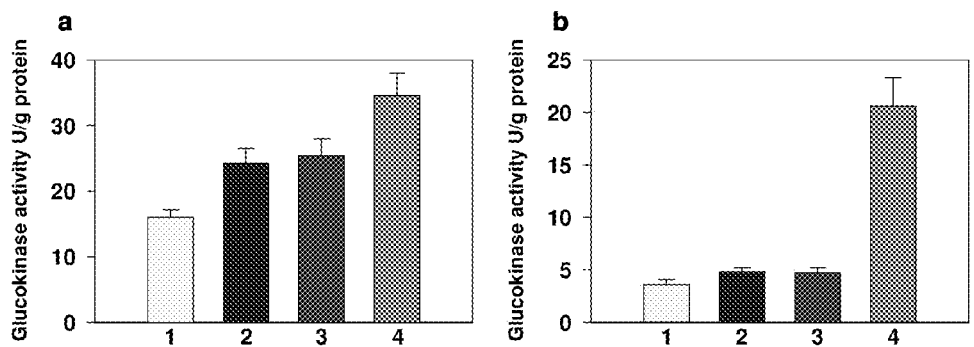
FIG. 5 is a graphical representation of Glucokinase activity of (1) Huh7, (2) Huh7ins, (3) Huh7ins (empty vector) and (4) Melligen cells in the presence of (a) 20 mM glucose, and (b) 20 mM glucose plus 10 mM glucose-6-phosphate. Means±SEM, n=6.

Qualitative western analysis showed the presence of human glucokinase in all cell lines tested, but their appeared to be an upregulation of the protein in the Melligen cells (FIG. 4). Huh7, Huh7ins and Huh7ins empty vector cells contain 16±1.2, 24.2±2.3, 25.4±2.6 U/g protein of glucose phosphorylating activity, respectively when assayed at 20 mM glucose in the absence of glucose-6-phosphate, but this activity is reduced to 3.0±0.5, 4.8±0.4 and 4.7±0.5 U/g protein respectively when the assay is conducted in the presence of 10 mmol/l glucose-6-phosphate (FIG. 5). This indicates that most of the glucose-6-phosphate activity is contributed by low $K_m$ glucose-6-phosphate sensitive hexokinases in the Huh7 cell lines. By comparison Melligen cells have a significantly higher (P<0.01) level of glucose-phosphorylating capacity compared to the other cell lines when measured in the absence of glucose-6-phosphate of 34.6±3.4 U/g protein, which correlates with the increased protein concentration in the western blot. However, in the presence of glucose-6-phosphate Melligen cells exhibit a 3-fold enhancement in activity: 20.6±2.7 U/g, over the Huh7ins cells, therefore in Melligen cells hexokinase activity represents '42% of the total glucose phosphorylating capacity, with the remainder contributed by glucose-6-phosphate-insensitive glucokinases.

Acute Stimulation of Insulin Secretion

Figure 6:
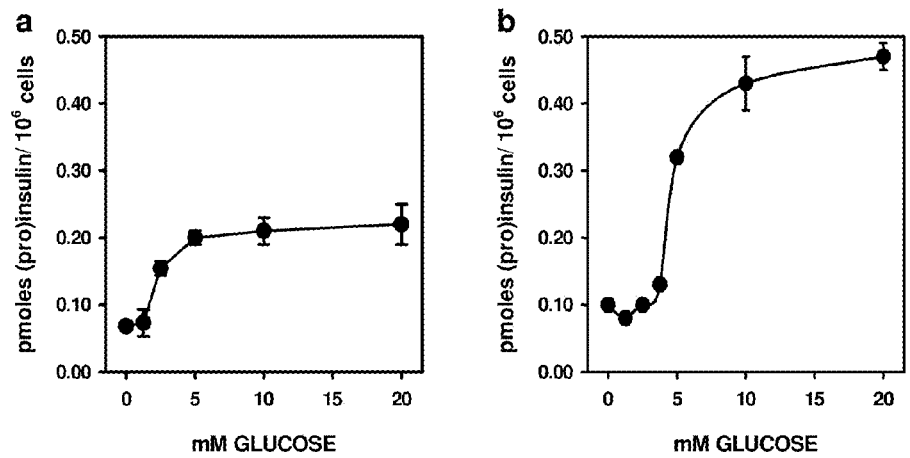
FIG. 6 is a graphical representation of insulin secretion from (a) Huh7ins and (b) Melligen cells in response to increasing concentrations of glucose: 1.5-20 mM. Values are expressed as means±S. E. (n=3).
Figure 7:
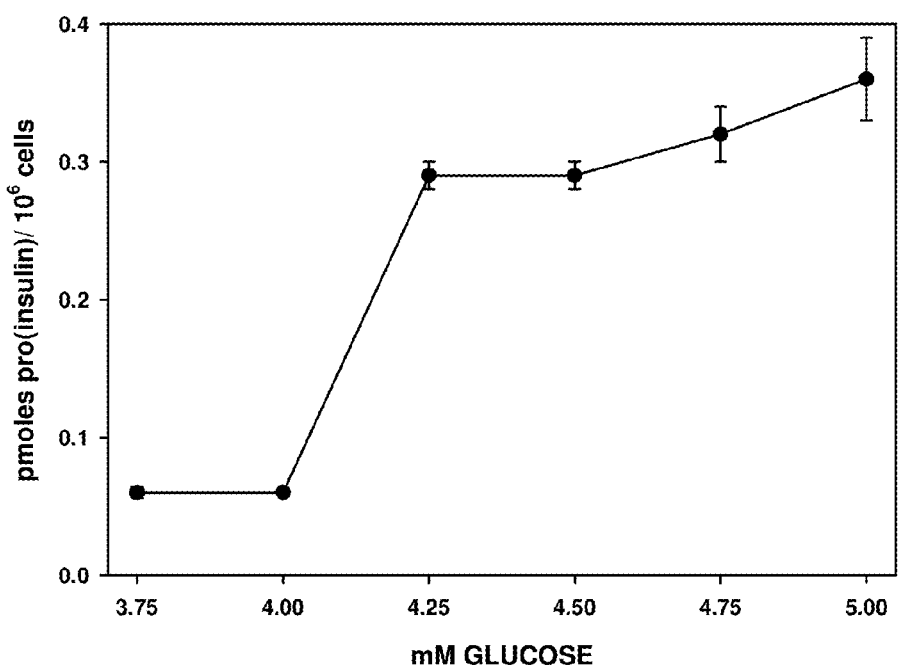
FIG. 7 is a graphical representation of insulin secretion from Melligen cells in response to increasing concentrations of glucose: 3.75-5.0 mM. Values are expressed as means±S. E. (n=6).

Before stimulation, 5×10$^6$ cells (Huh7, Huh7ins with the vector only and Melligen cells) were plated into each well of a six well plate overnight, then tissue culture plates were thoroughly washed with basal medium (PBS containing 1 mM $CaCl_2$ and supplemented with 20 mM HEPES and 2 mg/ml BSA, 1.25 mM glucose) to remove culture medium and FCS. Monolayers were incubated in the basal medium at pH 7.4 for two consecutive periods of 1 hour to stabilize the basal secretion of insulin. Monolayers were then exposed to stimuli for 1 hour. Glucose, 1.25-20 mM was dissolved in basal medium. Basal medium alone was used as a control. In response to increasing concentrations of glucose from 1-20 mM, a dose-response curve for insulin secretion was generated for a number of Melligen cell clones and compared with that for the parent Huh7ins cells. It can be seen in FIG. 6 that while glucose responsiveness commenced at 2.5 mM in Huh7ins cells, it commenced in the physiological range between 4-5 mM in the Melligen cells. The actual level of insulin secreted to glucose in the physiological range was also double that of the parent Huh7ins cells in clone 6 cells, which were used in all subsequent experiments, Assay of Huh7ins cells with vector alone were not significantly different from the Huh7ins cells (results not shown). Further experiments determined the exact concentration of glucose at which Huh7ins-GK cells commenced glucose-responsive insulin secretion to be 4.25 mM (FIG. 7).

Insulin Secretion and Storage

Huh7ins with the vector only and Melligen cells were washed with PBS, trypsinised and removed from tissue culture flasks. The suspended cells were centrifuged at 1000 rpm for 5 minutes and supernatant was aspirated. The cells were resuspended in the desired volume of fresh medium, a cell count was performed and the cells were distributed into 1.5 ml tubes at a density of 5×10$^6$ cells per tube. The tubes were centrifuged at 1800 rpm for 5 minutes and the supernatant was discarded. The cells were resuspended in 300 μl of 0.18N HCL in 70% ethanol for 48 hours at 4° C., to allow sufficient time for lysis of cells and release of stored insulin. For measurement of insulin content, samples were diluted in 1:10 before being placed in the radioimmunoassay (RIA).

Insulin Secretion Test (RIA Assay)

Levels of human insulin were measured by a RIA specific for this peptide and its split products as described previously (Tuch et al., 2003, *Gene Therapy* 10:490-503). Specificity was established by showing <0.05% cross-reactivity with insulin. The insulin RIA was carried out using guinea pig insulin antibody (Wellcome, England) and $^{125}$I-labelled insulin prepared by the chloramine-T method. Cross-reactivity with human proinsulin was 73%. Human insulin standards were used to assay the product from liver cells.

Transmission and Immuno Electron Microscopy

For morphological analysis by electron microscopy, Melligen cells were fixed (2% glutaraldehyde/1% paraformaldehyde) and processed according to conventional techniques using uranyl acetate block staining and Reynold's lead citrate counter-staining of ultrathin sections (80 nm). Stained sections were examined at 80 kV on a Phillips CM 10 transmission electron microscope. Granule size was measured directly from the images after calibrating with replicas (FIG. 8a).

For immunoelectron microscopy, a post-embedding immunogold procedure was used to confirm the localization of intracellular insulin. Single cell suspensions of Melligen and MIN-6 cells (mouse insulinoma cell line, used as a positive control) were analyzed. Briefly, the sections were incubated in 50% sodium metaperiodate at 50° C. for 3.5 minutes followed by 0.01M sodium citrate buffer pH 6.0 at 95° C. for 10 minutes and a 15 minute cooling period. Non specific binding was blocked using 1% goat serum for 30 minutes at room temperature. A goat anti guinea pig 10 nm (1:50) gold probe (Aurion, Wageningen, The Netherlands) incubated for 2 hours at room temperature was directed against a polyclonal guinea pig anti human insulin (1:20) primary antibody (Zymed, San Francisco, USA) incubated overnight at 4° C. Primary antibody was replaced by PBS to assess the level of non specific binding of the gold probe. Sections were counter-stained with Reynold's lead citrate prior to examination (FIG. 8b).

Statistical Analysis

Data were expressed as means±S.E. Paired sample means were compared with Student's t-test.

Results

FIG. 2 shows the sequence of the pIERSpuro3 vector (5157 base pairs sequence) with insert human islet glucokinase cDNA (2733 base pairs), which was cloned into the vector at the 972 bp site. Both junctions of the vector and insert have been sequenced (results not shown).

Example 2

Melligen Cells can Correct Diabetes by Retaining Insulin Secretory Responsiveness to Glucose Stimulation In Vivo In vivo glucose responsiveness in the millimolar concentration range is the hallmark of an artificial β cell for insulin replacement therapy in Type 1 diabetes. Where this can be achieved, such artificial β cells offer a potential strategy to overcome the limited availability of human pancreatic donor tissue. The survival of unencapsulated Huh7ins cells in a diabetic immunodeficient mouse model has been demonstrated.

To test the feasibility of Melligen cells to correct the diabetic state without inducing hypoglycaemia, Melligen cells ($10^7$ cells) are transplanted subscapularly into non-autoimmune non-obese diabetic severe combined immunodeficiency (NOD.scid) mice. Groups of eight animals are required for these experiments. Diabetes (blood glucose levels exceeding 14 mM on two separate occasions and serum insulin concentration below 0.15 ng/mL) is induced by a single high dose of STZ (250 mg/kg body weight). After transplantation, body weight and blood glucose is monitored three times each week and then daily if blood glucose concentrations decrease below 4 mM. Transplantation is considered successful if the non-fasting blood glucose concentration returns to normal (less than 8.4 mM) within 5 days after surgery. Animals are maintained on exogenous insulin immediately after transplantation if necessary. Transplants are considered unsuccessful if the blood glucose concentration increases to more than 20 mM on more than two occasions. After transplantation and when blood glucose levels are between 5 and 10 mM, glucose tolerance tests are performed and blood glucose and serum insulin levels assayed. If blood glucose levels fall to less than 2 mM for more than 24 h the animal is sacrificed and the transplant removed. If the normoglycaemic state is retained, then explants will be harvested at 2, 6 and 12 weeks after transplantation from a cohort to verify that hyperglycaemia subsequently returns. At 2, 6, and 12 weeks pancreas is prepared for insulin immunohistochemistry. After resection, the graft is weighed and the proliferative characteristics of Melligen cells quantified by MTT assay over a period of 72 h. The insulin content of the graft is measured. Explants are also examined for gene expression (of glucokinase, GLUT2 glucose transporter, and insulin by PCR), histologically (for cellular integrity, insulin secretory granules, and vascularisation) and immunohistochemically (for insulin).

Example 3

Microencapsulation Melligen Cells to Provide a Means of Ectopic Insulin Production and Secretion Both (A) In Vitro and (B) In Vivo with the Avoidance of Autoimmune Destruction (a) In Vitro Experiments Using Encapsulated Melligen Cells Melligen cells are microencapsulated and then cultured in vitro for up to 6 weeks. Viability and glucose responsiveness of encapsulated Melligen cells are determined after 1, 2, 4 and 6 weeks in culture prior to commencing any in vivo studies using microencapsulated cells. A dose response curve for insulin secretion in response to glucose from basal to high glucose levels of the encapsulated cells is established. Chronic and acute insulin release by the encapsulated cells is determined. To measure acute insulin release, static incubations are carried out with traditional stimuli (glucose, theophylline, and 8-Br-cAMP [which increases intracellular cAMP]). Insulin storage is also examined after sonication and extraction overnight in acid ethanol. Insulin storage and secretion is measured by insulin RIA as previously described (Tuch, et al., 2003, *Gene Therapy* 10:490-503; Permutt et al., 1989, *Proc Natl Acad Sci USA*, 86:8688-8692). The percentage of live and dead cells is identified by observing calcein and propidium iodide fluorescence, respectively, using a confocal microscope. Among the cytotoxic factors which are responsible for limited survival of encapsulated grafts the most important are thought to be cytokines. To determine cytokine-induced Melligen cell destruction, unencapsulated and microencapsulated cells are co-cultured with pro-inflammatory cytokines. Encapsulated Melligen cells are with activated human macrophage cell lines and viability and insulin secretion subsequently determined.

(b) In Vivo Experiments Using Encapsulated Melligen Cells (i) Evaluation of Biocompatibility of Microcapsules For this therapy to become clinically viable, the microcapsules must not provoke excessive cellular overgrowth, which would limit the diffusion capacity and the life span of the transplant. Therefore, empty microcapsules are transplanted subscapsularly into 6-week-old non-obese diabetic (NOD) mice that have not yet developed spontaneous diabetes. At 2, 6, and 12 weeks after transplantation, the microcapsules is removed and the degree of capsular overgrowth determined.

(ii) Transplantation of Encapsulated Melligen Cells

Encapsulated Melligen cells are analysed to determine if they can reverse autoimmune diabetes without the subsequent development of hypoglycaemia. Spontaneously diabetic NOD mice are used for these experiments. Correction of diabetes is ascertained by the same scenario as for unencapsulated Melligen cells and glucose tolerance tests are performed. Capsules are removed 2, 6, and 12 weeks after transplantation and examined for capsular overgrowth and explanted capsules are also evaluated for insulin secretion in response to glucose, insulin content, and viability (MTT assay) and immunohistological examination.

(iii) Immunoreactivity of Encapsulated Melligen Cells

Results indicate that that unlike pancreatic β cells, insulin-expressing liver cells may not be susceptible to autoimmune destruction. However, inflammatory reactions may be generated if antigenic products from encapsulated dying cells diffuse through the microcapsule. Therefore, an analysis is performed to determine if microcapsules prevent communication between Melligen cells and immune cells that might cause lymphocyte activation. This is achieved using a conventional splenocyte co-culture system. IgG deposition is also assessed on the microcapsules and the Melligen cells contained in the microcapsules (after incubation of microcapsules with FITC-labelled anti-mouse IgG antibody) at 6 and 12 weeks after transplantation, to determine if antibodies are induced by either antigens shed from the cell surface, proteins secreted by live cells, or liberated after cell death that may diffuse through the capsule.

Example 4

Resistance of Insulin Secreting Liver Cell Line to Pro-Inflammatory Cytokines Involved in Beta Cell Death Results Preliminary experiments were conducted to determine appropriate dilutions of the cytokines, IFN-γ, TNF-α and IL-1β, that would reduce viability in the control β-cell line, MIN-6. Cytokines were also tested for efficacy both individually and in combination according to the experimental design of Tabiin et al. (2001). The MTT assay for cell viability was employed to determine the cytotoxic effect of cytokines on Huh7ins cells, Melligen cells, and the parent cell line, Huh7. Annexin V/PI staining allowed detection of necrotic and apoptotic populations in cytokine treated and untreated cells.

Characterisation of Cell Growth

Figure 9:
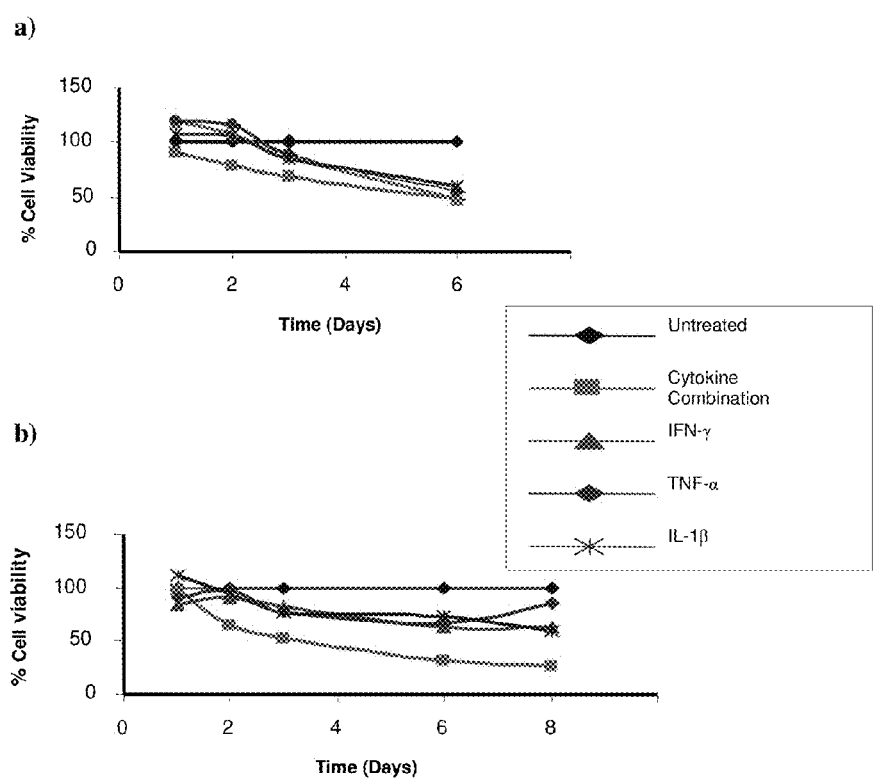
FIG. 9 is a graphical representation of MIN-6 cells incubated with the pro-inflammatory cytokines IFN-γ (384 ng/mL), TNF-α (10 ng/mL) and IL-1β (2000 pg/mL) in combination and individually a) over 6 days replacing the cytokines and media once every 2 days and b) over 8 days with the cytokines and media changed daily. Control cells were incubated in media alone. Results expressed as mean±SE (n=4; SEs fell within data points).

To establish the growth kinetics of each of the cell lines (MIN-6, Huh7, Huh7ins and Melligen) used in this study, cell numbers were quantified over varying periods of time. An initial seeding density of $1 \times 10^4$ cells/mL in 6 well plates was used, based on previous experiments, and growth curves were generated. Each of the cell lines reached stationary phase at different rates (FIG. 9). Huh7, Huh7ins and Melligen cells approached exponential growth by day 8 when the cell concentration was approximately $1 \times 10^6$ cells/well. In contrast, MIN-6 cells only reached a cell concentration of $5 \times 10^5$ cells/mL at the same time-point (FIG. 9). It was also found that the highest recorded cell number for the MIN-6 cells ($1 \times 10^6$ cells/mL) was only reached at day 10. As MIN-6 and Huh7 cells are of murine pancreatic and human liver origin, respectively, each cell line exhibited distinct growth kinetics. These cell growth characteristics were used to determine the time course for experiments in which cytokines were co-incubated with cell lines. Since MIN-6 cells reached the log growth phase at a later time point, this cell line was plated at higher seeding densities when run in parallel experiments with Huh7 and Huh7ins to ensure that the cells were in log phase when used in the cytokine toxicity experiments.

As the MTT assay was to be used to determine cell viability in both the presence and absence of cytokines, preliminary experiments were performed to determine cell viability of untreated Huh7ins cells. Huh7ins cells were seeded at an initial density of $1 \times 10^3$ cells/well into a 96-well plate and cultured for 8 days. In the MTT assay, MTT is metabolised by mitochondrial dehydrogenase within the viable mitochondria of a cell to produce a purple coloured crystal, formazan. When dissolved in DMSO the absorbance of the formazan solution can be read at 570 nm. The MTT assay is a rapid and reproducible method for determining cellular response to cytotoxic agents.

Figure 11:
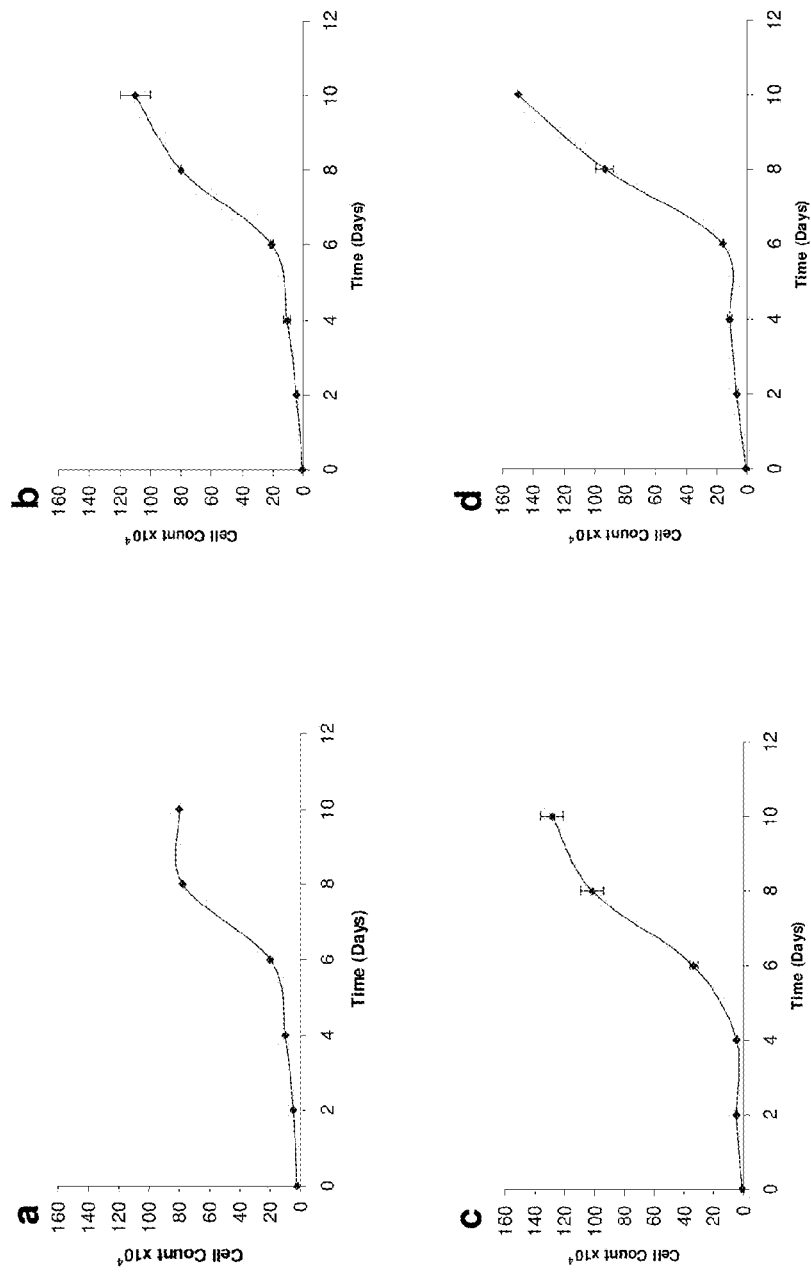
FIG. 11 is a graphical representation of the growth kinetics of MIN 6 cells and the three liver cell lines used. Cells were initially seeded at a density of $1 \times 10^4$ cells/mL, for liver cell lines, and $2 \times 10^4$ cells/mL, for MIN-6 cells, into six well plates. Cell counts were obtained using a haemocytometer every second day throughout the period studied a) MIN-6 b) Huh7 c) Huh7ins and d) Melligen cells. Results expressed as mean±SE, (n=3) (At some time points the SEs fall within the data point).
Figure 12:
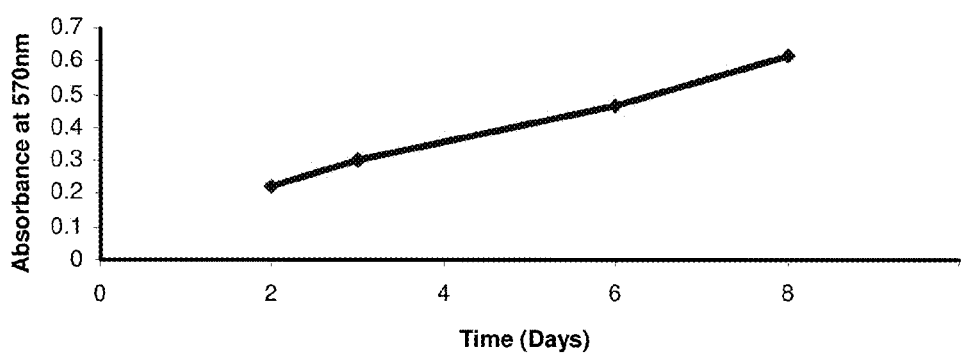
FIG. 12 is a graphical representation of an MTT viability assay on Huh7ins cells performed to ensure that exponential growth was detected by the assay over 8 days. Results are expressed as mean±SE (n=6; SEs fell within data points).

The results obtained from this preliminary experiment showed that the seeding density chosen approached an absorbance value of 1.0 nm over the 8-day period. The initial seeding density used was optimal since subsequent experiments to assess the cytotoxic effect of cytokines were to be conducted for between six and twelve days. These results also showed that the exponential growth of the cells was reflected by the mitochondrial activity of the cells. From the growth kinetic results (FIG. 11) it was also determined that MIN-6 cells would be plated at twice the seeding density as the liver cell lines.

Optimisation of Cytokine Treatment on MIN-6 Cells by the MTT Assay

Initial experiments used serial dilutions of single cytokine concentrations of IFN-γ, TNF-α and IL-1β. The $ED_{50}$ (effective dose required to destroy half the cell population) indicated on the respective data sheet for each cytokine constituted the most dilute concentration used (Table 1). These initial titration experiments were necessary as each $ED_{50}$ value provided on the data sheets applies to a specific application and a specific cell line. Additionally, different preparations of cytokines exhibit differing potencies.

TABLE 1

OPTIMISATION OF SINGLE CYTOKINE CONCENTRATIONS FOR MIN-6 CELLS

| IFN-γ ng/mL | TNF-α ng/mL | IL-1β ng/mL |
|---|---|---|
| 19.2 | 5.00 | 0.50 |
| 9.60 | 2.50 | 0.25 |
| 4.80 | 1.25 | 0.125 |
| 2.40 | 0.63 | 0.063 |
| 1.20 | 0.31 | 0.031 |
| 0.60 | 0.16 | 0.016 |
| 0.30 | 0.08 | 0.008 |
| 0.15 | 0.04 | 0.004 |

Results from the MTT assay revealed that co-incubation of MIN-6 cells with the concentrations of single cytokines at the concentrations listed in Table 1 did not reduce the viability of MIN-6 cells as compared to untreated cells even after 14 days of co-incubation (data not shown). Consequently, the cytokines were used in combination and at higher cytokine concentrations. The concentrations employed were similar to those used by Tabiin et al. (2001) in studies investigating the cytokine treatment of both the rodent insulinoma cell line, NIT-1, and the insulin secreting human hepatocyte cell line, HEPG2 ins/g.

Media and cytokines IFN-γ (384 ng/mL), TNF-α (10 ng/mL) and IL-1β (2000 pg/mL) singly and in combination were changed once every two days and cells were assayed for viability over a six-day period. However, at the initial seeding density used ($2\times10^3$ cells/well), approximately 43±2% of MIN-6 cells were still viable at the final day of the experiment (FIG. 9a). The observation period was therefore increased to 8 days and the media and cytokines were changed daily. Under these conditions, by day 8, only 22±1% of MIN-6 cells were viable as compared to 100±1% for untreated cells (P=0.0045) (FIG. 9b).

As it was preferable to obtain the lowest percentage of viable cells by the final day of the experiment and to precisely determine the kinetics of cytokine induced death, the triple cytokine combination concentration were further titrated by adding the cytokines at twice IFN-γ (768 ng/mL), TNF-α (20 ng/mL) and IL-1β (4000 pg/mL) and half the triple cytokine concentrations IFN-γ (192 ng/mL), TNF-α (5 ng/mL) and IL-1β (1000 pg/mL) previously used.

After changing cytokines daily at the concentrations used in FIGS. 10a and b, approximately 20±2% of the cells still remained viable compared to 100±2% viability of the control cells (P=0.0065). Application of single cytokines did not produce the same toxic effect as the triple cytokine combination. Hence, the period of experimentation was extended to 10 days and cytokines were used at two times and five times higher than the concentrations used in FIG. 9.

Figure 13:
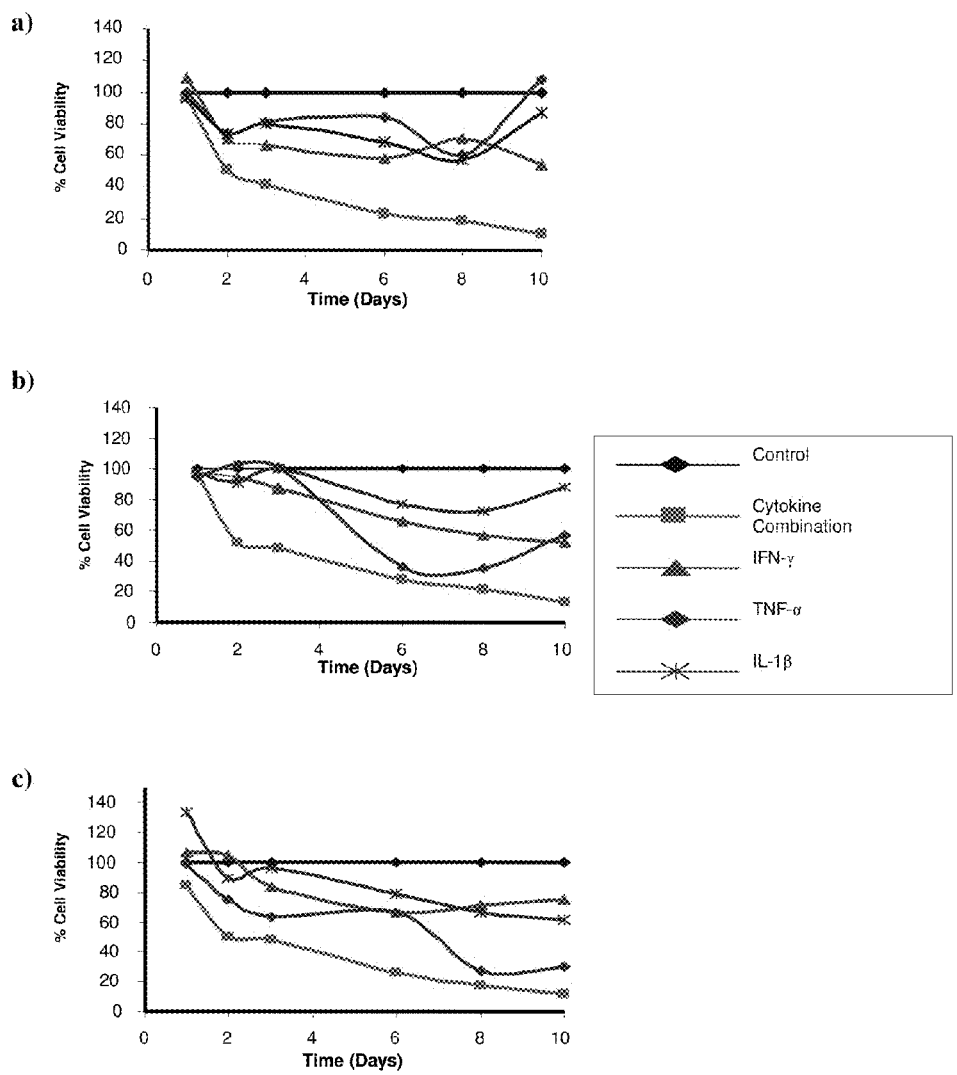
FIG. 13 is a graphical representation of an MTT viability assay on MIN-6 cells incubated with the cytokines IFN-γ (384 ng/mL), TNF-α (10 ng/mL) and IL-1β (2000 pg/mL). Media was changed daily. Cell viability was determined at various time points throughout the 10-day period. Cytokine concentrations used were a) 1 times b) 2 times more than and c) 5 times more than the initial concentrations. Results expressed as mean±SE (n=4; SEs fell within data points).

By day 10 only 15±2% of cytokine treated MIN-6 cells remained viable compared to 100±1% for untreated cells (P=0.0011) even after the concentrations were increased by up to 5 times the initial concentrations (FIGS. 13a and b). These experiments indicated that increasing cytokine concentrations beyond did not further reduce cell viability.

In summary, after titrating the cytokine concentrations on the MIN-6 cell line it was determined that the following concentrations would be suitable for future experiments over 10 days because they were most toxic to the pancreatic β-cell line when replenished daily IFN-γ (384 ng/mL), TNF-α (10 ng/mL) and IL-1β (2000 pg/mL).

MTT Assay

After establishing the optimised cytokine treatment to reduce the viability of MIN-6 cells, these experimental parameters were applied to Huh7 and Huh7ins cells. This was done to determine if the cytokines would have the same effect on the hepatoma cell lines with and without the insulin gene.

A significant difference in the susceptibility of MIN-6 cells and Huh7ins cells to cytokine-induced toxicity was observed from day 3 (P=0.018) (FIGS. 14a and c). By day 3, MIN-6 and Huh7ins cells that were treated with cytokines had viabilities of 72±5%. Untreated MIN-6 cells remained exponentially viable (100±1%) over the 10 days of the experiment. Treatment of MIN6 cells with the triple cytokines for 10 days caused a significant decrease in cell viability when compared to untreated cells (P=0.0039) (FIG. 14a).

When exposed to the cytokine combination for 10 days, Huh7, Huh7ins and Melligen cells showed no significant decrease in cell viability compared to the untreated control cells of each cell line (FIG. 14b-d).

Apoptosis and Cell Cycle Arrest are not Induced by Cytokine Cocktail in Insulin-Secreting Human Hepatoma Cells Translocation of the phosphotidylserine from the inner side of the plasma membrane to its outer layer is an early event of apoptosis. Annexin V is a calcium dependent phospholipid-binding protein with high affinity for phosphatidylserine. Propidium iodide (PI) is a standard cytometric viability probe that is excluded by cells with intact membrane. PI staining is performed simultaneously with the annexin V staining to differentiate apoptotic cells (single annexin V-positive) from necrotic cells (double annexin V-PI-positive), as necrotic cells also expose phosphatidylserine to annexin V because of the loss of membrane integrity (Vermes et al., 1995). Student's t-test was used and P values less than 0.05 were considered to be statistically significant.

Analysis of annexin V binding was performed at 24 and 48 h with and without cytokine treatment. Staining Melligen cells at 24 h time-point showed close to 0% annexin V-single positive cells (apoptotic) and 0% annexin V PI-double positive cells (late apoptotic) and 20% staining PI-only (necrotic). At 48 h, the percentage of necrotic cells in the cytokine-treated group did not differ significantly from that recorded in the untreated samples (19%).

Figure 14:
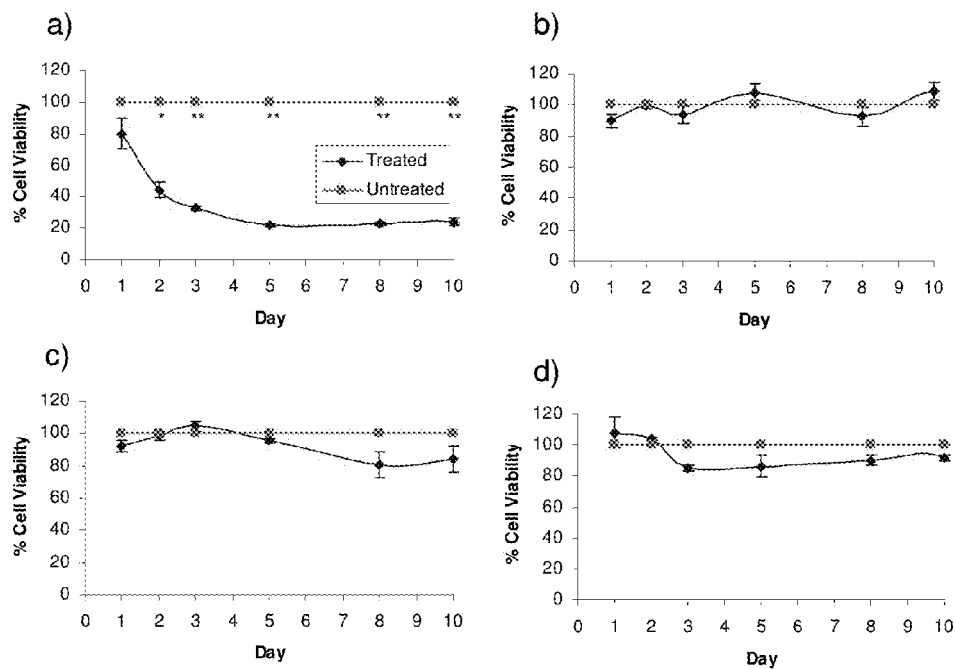
FIG. 14 is a graphical representation of an MTT viability assay on a) MIN-6 b) Huh7 c) Huh7ins d) Melligen cells incubated with the cytokines IFN-γ (384 ng/mL), TNF-α (10 ng/mL) and IL-1β (2000 pg/mL). Cytokines were changed daily over a 10-day period. Results expressed as mean±SE (n=5) (At some time points the SEs fall within the data point *P<0.01, **P<0.001).
Figure 15:
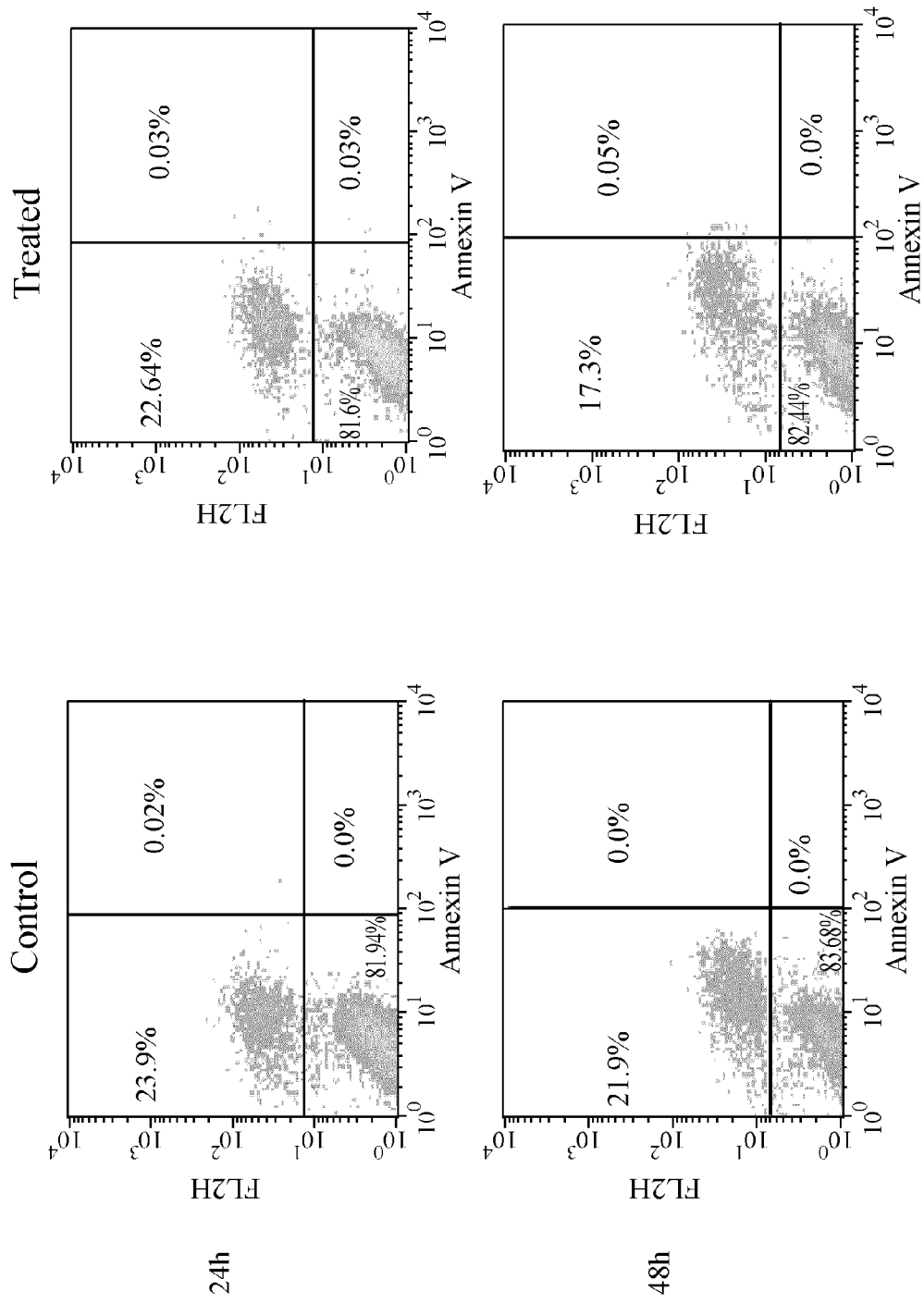
FIG. 15 is an image of Annexin/PI staining of Huh7ins at both 24 h and 48 h which shows no early or late apoptotic cell death. Only a necrotic population was detected and the difference between control and treated cells was not significant p>0.05. These figures are representative of four independent experiments.
Figure 16:
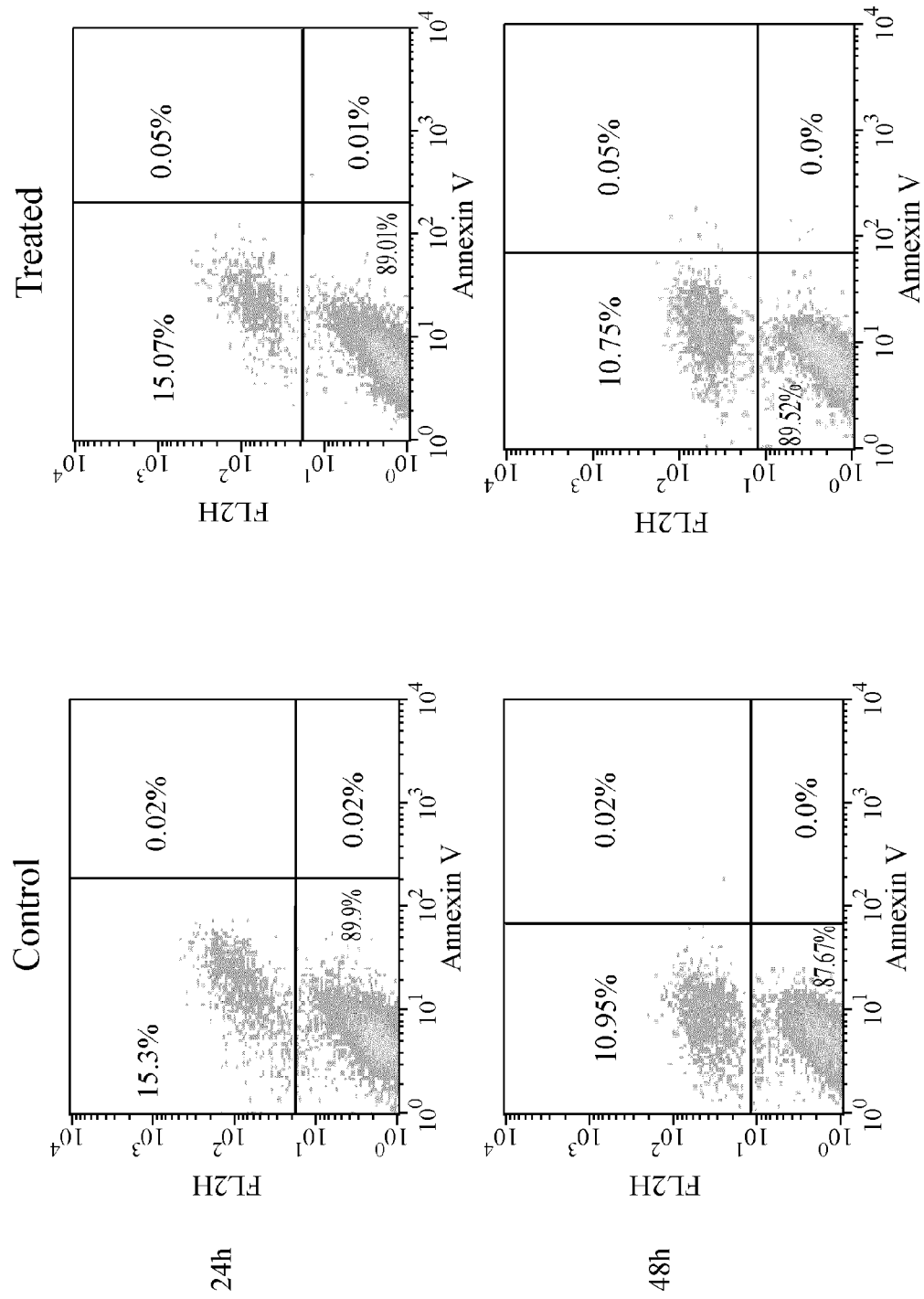
FIG. 16 is an image showing that at both 24 h and 48 h Melligen cells showed no early or late apoptotic cell death. Only a necrotic population was detected and the difference between control and treated cells was not significant p>0.05. These figures are representative of four independent experiments.
Figure 17:
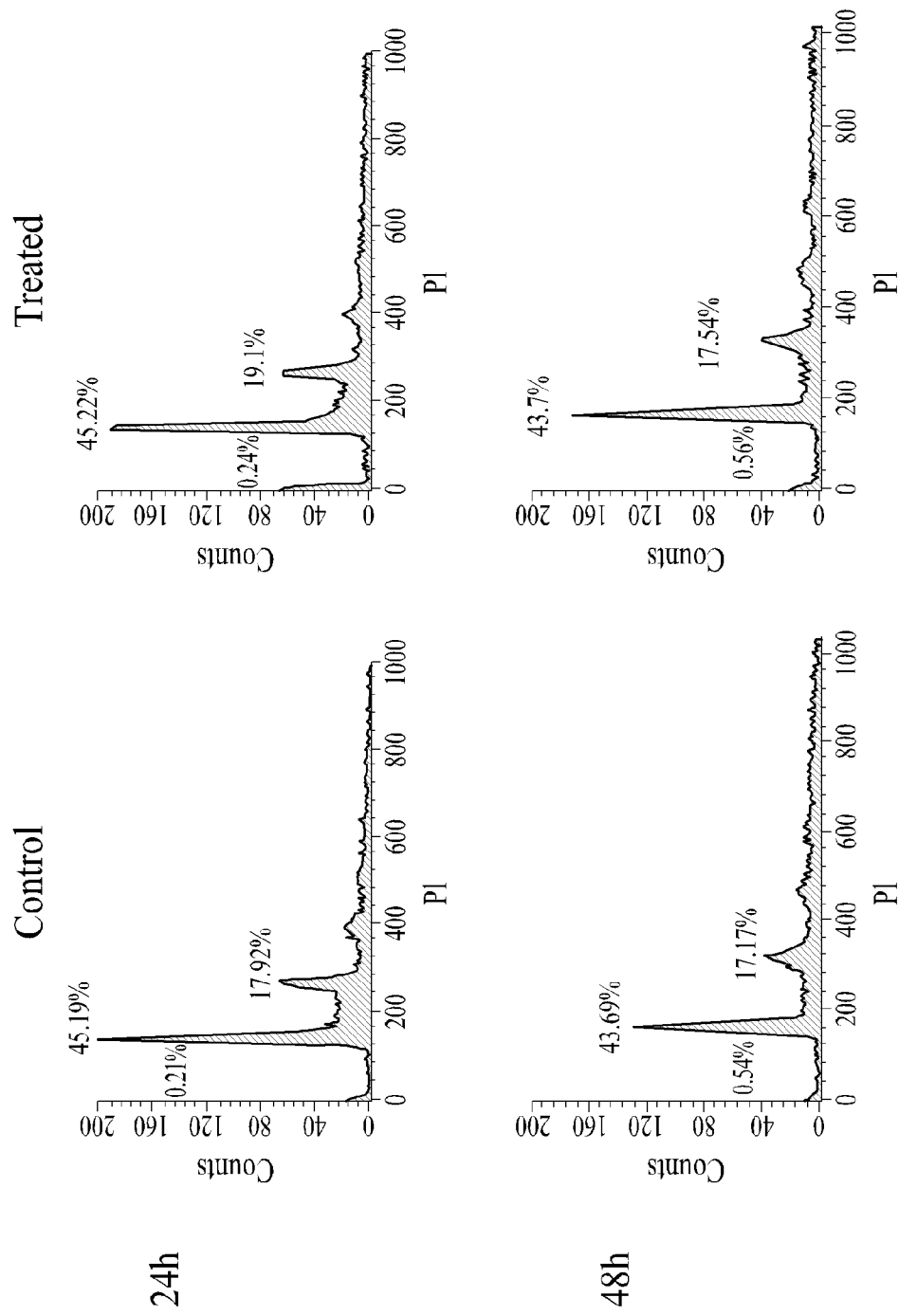
FIG. 17 is an image of Huh7ins PI only staining showing that there was no sub-G1 peak evident in treated and control cells at 24 h and 48 h. These figures are representative of four independent experiments.
Figure 18:
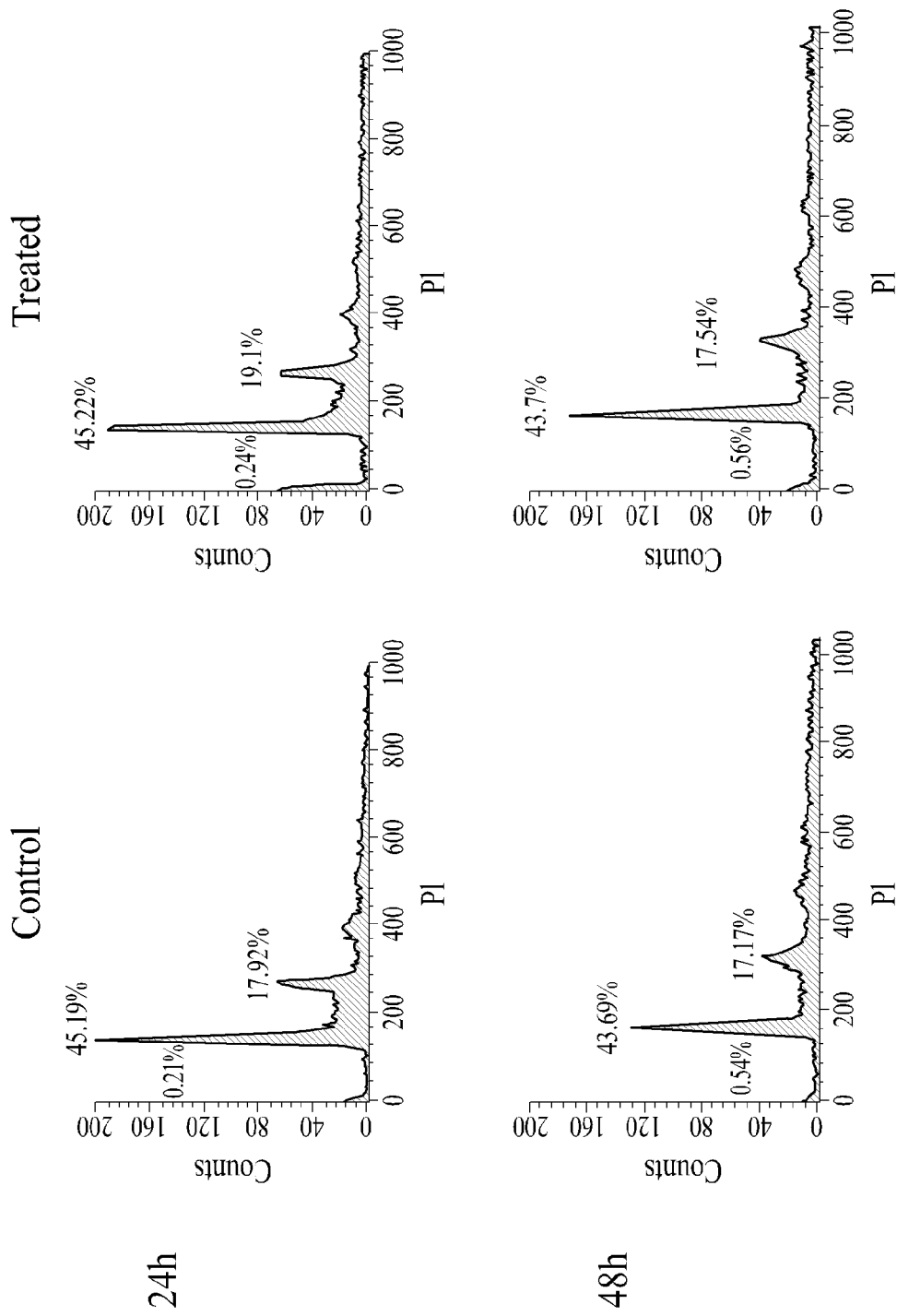
FIG. 18 is an image of Melligen cells PI only staining showing that there was no sub-G1 peak evident in treated and control cells at 24 h and 48 h. These figures are representative of four independent experiments.

To elucidate the effect of cytokines on the viability of Huh7ins, Melligen and MIN-6 cells using PI-only staining, the cells were incubated with the cytokine cocktail for 48 h. The viable cell number was not decreased in the insulin-secreting hepatoma cells by the cytokine cocktail treatment at 24 h and 48 h according to the MTT assay (FIG. 14). To examine whether the cytokine cocktail treatment induced apoptosis or cell-cycle arrest in Huh7ins and Melligen cells, the DNA content in these cells were analysed using flow cytometry after propidium iodide staining. In both insulin-secreting hepatoma cells, the cytokine treatment did not affect the number of cells in the subG1 phase of cell-cycle, representing apoptotic cells (FIGS. 17 and 18). In addition, there was no increase in the number of cells in the S-phase or G0/G1 phase, suggesting that cytokines do not reduce the viable number of cells through inducing apoptosis and cell cycle arrest at G0/G1 phase in insulin-secreting hepatoma cells. MIN-6 cell results not shown.

Cell Morphology

In FIGS. 19a, 19b and 19c, the untreated MIN-6 cells appeared to have intact cell membranes and remained attached to the plate in colonies growing as monolayers. By day 12 MIN-6 cells were confluent. In contrast, cytokine-treated MIN-6 cells started to degenerate with ruptured membranes causing cells to detach after 6 days (FIG. 19e). Complete degeneration with cell debris scattered between remaining cells was seen on day 12 (FIG. 19f).

Figure 20:
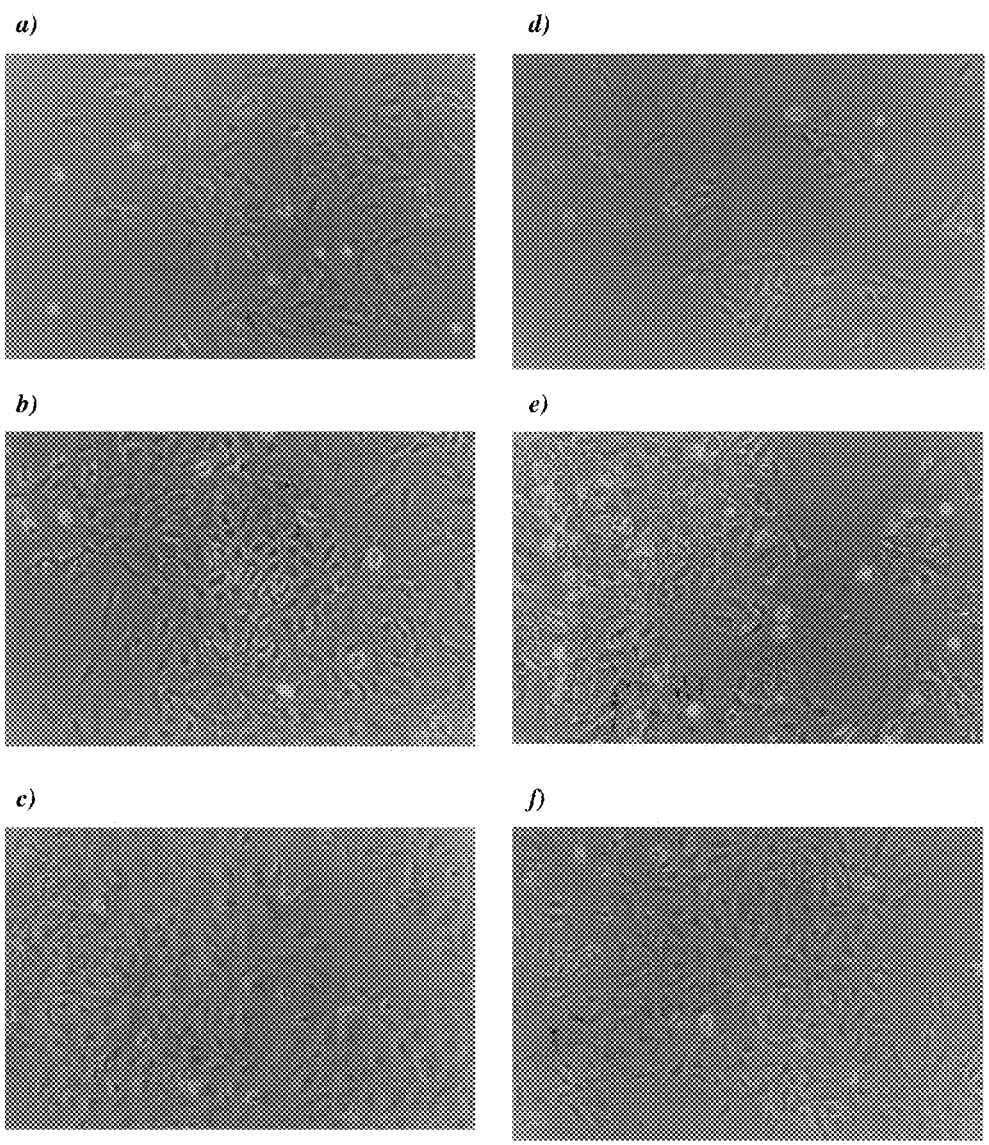
FIG. 20 is an image of the cell morphology of untreated Huh7ins cells following a) 1 day, b) 6 days, and c) 12 days. The cell morphology of Huh7ins cells incubated with the cytokines IFN-γ, TNF-α and IL-1β following the same time points d) 1 day, e) 6 days, and f) 12 days. (100× magnification). Morphology of the Melligen cells was the same as the Huh7ins cells.

Co-incubation of Huh7ins and Melligen cells with the cocktail of pro-inflammatory cytokines did not induce morphological changes consistent with cell death after day 1 (FIG. 20d) or day 6 (FIG. 20e). At both these time-points Huh7ins and Melligen cells were attached and of uniform size. However, by day 10 the cytokine-treated Huh7ins cells (FIG. 20f) appeared less dense when compared to the untreated cells (FIG. 20c). The remaining treated cells appeared intact, attached and there was an absence of cell debris as observed for the cytokine-treated MIN-6 cells. The morphology of both the MIN-6 and liver cell lines corroborates the results obtained from the MTT cell viability assay, which indicated that liver cell lines were more resistant to the toxic effects of the pro-inflammatory cytokines.

Figure 21:
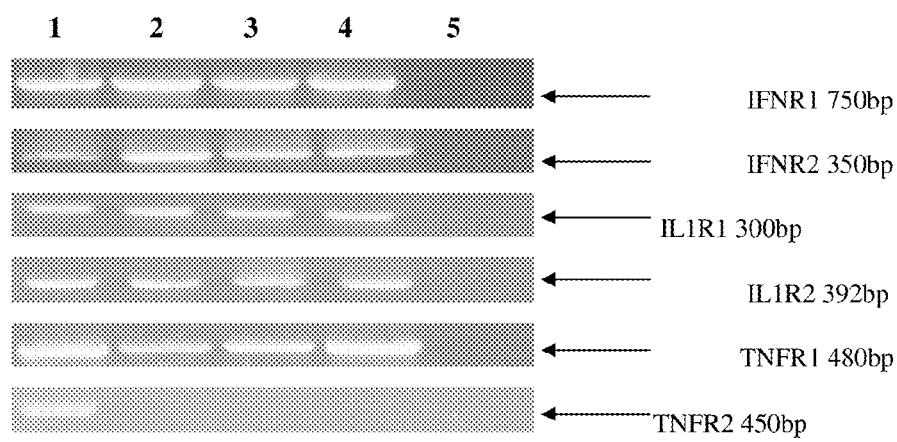
FIG. 21 is an image showing RT-PCR performed using primers for IFNR1, IFNR2, IL1R1, IL1R2, TNFR1 and TNFR2 cytokine receptors. Lanes contain cDNA for: 1—Pancreatic Islet Cells (positive control) 2—Huh7 Cells 3—Huh7ins Cells 4—TAO Cells 5—Negative control. Results show bands for IFNR1, IFNR2, IL1R1, IL1R2 and TNFR1 but not TNFR2 cytokine receptor. The TNFR2 Cytokine Receptor was not detected at the Molecular Level in the liver cell lines.

Cytokine Receptors and Cell Signalling Cascades:

To establish if observed resistance of the liver cell line to the pro-inflammatory cytokine cocktail is due to the absence of the cytokine receptors, RT-PCR was performed using cDNA generated from RNA isolated from human primary islet (positive control), Huh7 (parent cell line), Huh7ins (Huh7 transfected with the insulin gene) and Melligen (further modified Huh7ins) cells with primers for IFNR1, IFNR2, IL1R1, IL1R2, TNFR1 and TNFR2. Molecular expression of cytokine receptors IFNR1, IFNR2, IL1R1, IL1R2 and TNFR1 was confirmed in all cells (FIG. 21). Therefore, the reduced susceptibility to cytokine-induced killing displayed by Melligen cells cannot be attributable to the absence of receptors for the cytokines.

RT-PCR was performed using primers for IFNR1, IFNR2, IL1R1, IL1R2, TNFR1 and TNFR2 cytokine receptors. Lanes contain cDNA for: 1-Pancreatic Islet Cells (positive control) 2-Huh7 Cells 3-Huh7ins Cells 4-Melligen Cells 5-Negative control. Results show bands for IFNR1, IFNR2, IL1R1, IL1R2 and TNFR1 but not TNFR2 cytokine receptor.

Figure 23:
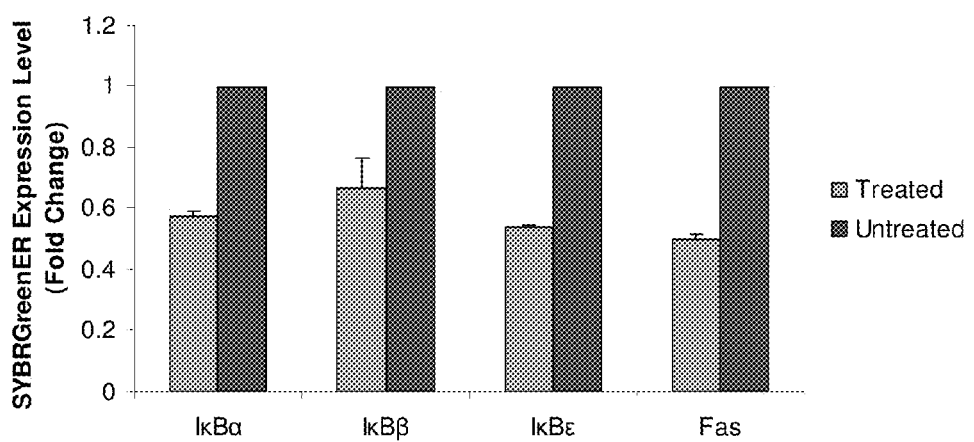
FIG. 23 is a graphical representation of real time PCR results showing that inhibitors of NFκB are down-regulated in the Melligen cells. Down-stream effector molecule, Fas, is also down-regulated. These trends in gene expression were also seen in Huh7 and Huh7ins cells.

Downstream of TNF receptor (TNFR) 1 associated death domain protein (TRADD), receptor-interaction protein and TNF receptor associated factor (TRAF) 2 activate the NF-κB pathway. NF-κB has been reported to initiate the expression of various genes associated with anti-apoptosis, cell growth, and immune response in liver cells. No significant difference in the cytokine-induced activation of NF-κB was observed between the treated Huh7, Huh7ins and Melligen cells (FIG. 23). These results indicate that the cytokine cocktail induces NF-κB activation irrespective of the presence of the insulin gene, and the anti-apoptotic mechanism in these liver cell lines seems to be independent of NF-κB activation.

Iκb Gene Expression in Cytokine-Induced Insulin-Secreting Human Hepatoma Cell

Figure 22:
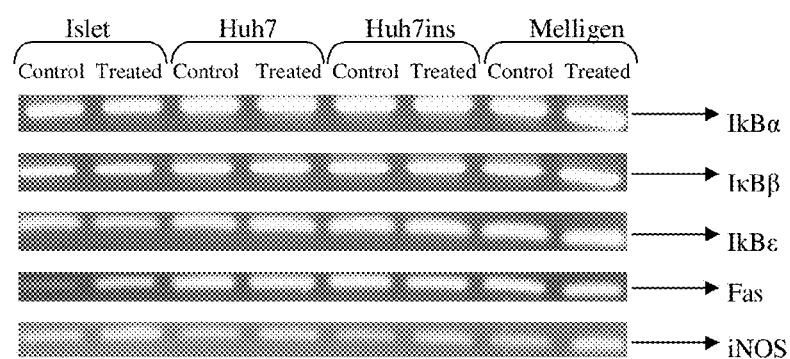
FIG. 22 is an image of RT-PCR performed using primers for IκBα, IκBβ and IκBε. Lanes contain cDNA for: control and treated pancreatic islet cells (positive control), control and treated Huh7 Cells, control and treated Huh7ins Cells, and control and treated Melligen Cells. Results show bands for IκBα, IκBβ, IκBε and iNOS but not MCP-1.

To investigate the downstream effects of inhibiting NFkB signalling, cytokine-induced gene expression in Huh7, Huh7ins and Melligen cells was evaluated. Gene expression of Fas and iNOS was switched off after the addition of cytokines to the liver cell lines (FIG. 22). After cytokine exposure, the relative abundance of iNOS and Fas mRNAs (optical density corrected per GAPDH abundance) was, respectively about 2-fold lower in control cells not treated with the cytokine cocktail expression of the housekeeping gene GAPDH was not affected by exposure to cytokines.

Nitric Oxide Determination

The iNOS enzymatic activity was estimated by measurements of medium nitrite (a stable product of nitric oxide (NO) oxidation) accumulation by the modified Griess reaction during a 48 h exposure to cytokines, IFN-γ (384 ng/mL), TNF-α (10 ng/mL) and IL-1β (2000 pg/mL). In the modified Greiss reaction, nitric oxide production by MIN-6, Huh7, Huh7ins and Melligen cells was measured as nitrite accumulation in conditioned medium and determined by the modified Griess reaction. In brief, 50 µL of cell free medium were mixed with an equal volume of 1% sulphanilamide (Sigma, USA) in 5% phosphoric acid. The plate was incubated for 5 to 10 minutes at room temperature, protected from light. NED solution (0.1% N-1-naphthylethylenediamine dihydrochloride in water) (Sigma, USA), 50 µL per well, was then added to all wells and the plate was again incubated for 5-10 minutes at room temperature, protected from light. The nitrite concentration was determined in triplicate within a concentration range that corresponded to the linear part of the standard curve. Absorbance was measured at 540 nm in a microplate reader (BioTek, USA).

Figure 24:
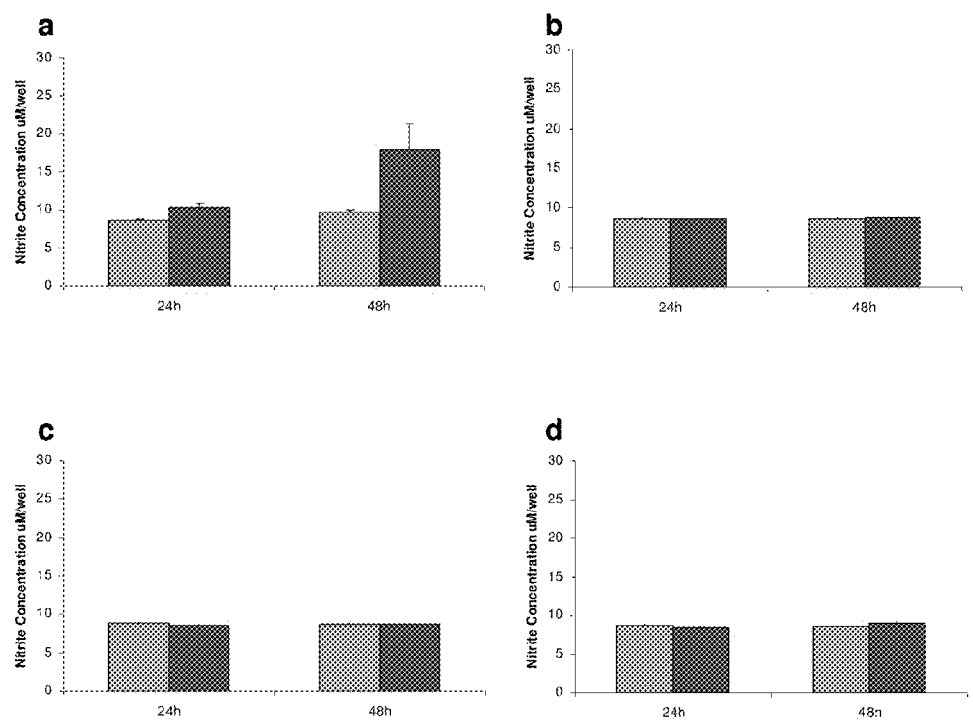
FIG. 24 is a graphical representation showing NO concentrations in a) Min 6, b) Huh7, c) Huh7ins and d) Melligen cells. Increased NO concentrations were not detected in liver cell lines after 48 h cytokine treatment, using the modified Greiss reaction. Results are expressed as mean±SE (n=6).

Using the modified Griess reaction amounts of nitrite released into the culture media of cytokine treated and untreated MIN-6 cells were determined at 24 h and 48 h. Significantly higher concentrations of NO were detected in cytokine treated MIN-6 cells at both 24 h and 48 h (P<0.01). Treated Huh7, Huh7ins and Melligen cells on the other hand did not exhibit an increase in NO production compared to untreated cells at either 24 h or 48 h time-points (P>0.05). (FIG. 24)

Effect of Cytokines on Insulin Secretion, Storage and Glucose Responsiveness

For Melligen cells to be suitable candidates as artificial β-cells they must continue to be glucose-responsive and store and secrete insulin in the pro-inflammatory cytokine milieu. Therefore, the effects of IFN-γ, TNF-α and IL-1β on insulin secretion, storage and glucose-responsiveness of Huh7ins and Melligen cells were determined.

The glucose-responsive insulin secreting pancreatic β-cell line, MIN-6, (Miyazaki et al., 1990), was used as a positive control. To determine if the triple cytokine treatment had an effect on chronic insulin secretion, storage and glucose responsiveness, the cells were exposed to cytokines [IFN-γ (384 ng/mL), TNF-α (10 ng/mL) and IL-1β (2000 pg/mL)]. Media and cytokines were changed daily over the 10-day period studied. An insulin RIA was used to determine insulin concentration in the samples collected.

Chronic Insulin Secretion and Storage

Figure 25:
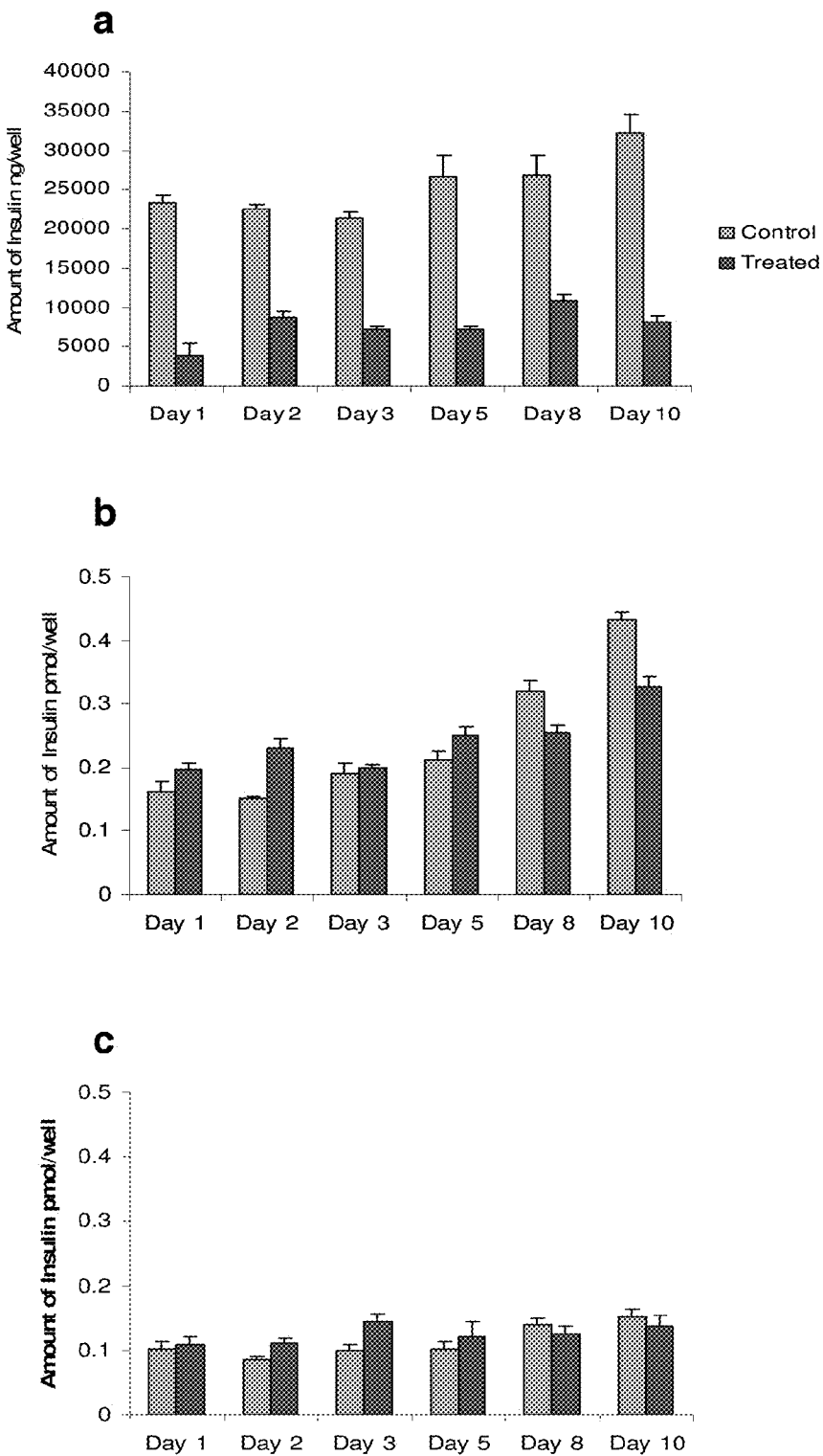
FIG. 25 is a graphical representation showing total chronic insulin secretion after incubation with and without the cytokine mixture IFN-γ, TNF-α and IL-1β for 1, 2, 3, 5, 8 and 10 days a) MIN-6 cells b) Huh7ins cells and c) Melligen cells. Results are expressed as mean±SE (n=6).

Cytokine-treated MIN-6 cells secreted significantly less insulin (14005±1317 ng/well) than untreated MIN-6 cells (21408±814 ng/well) at day 1 (P=0.012) and throughout the entire period studied (FIG. 25a). Insulin levels for cytokine-treated MIN-6 cells at day 10 represented the total amount of insulin secreted over the entire 10 days. In contrast, Huh7ins cells co-incubated with cytokines secreted amounts of insulin that were not significantly different to those secreted by the untreated Huh7ins and Melligen cells over the 10-day period (FIG. 25b).

Effect of Cytokines on Insulin Storage

MIN-6, Huh7ins and Melligen cells were treated over 10 days with cytokine cocktail IFN-γ, TNF-α and IL-1β. Stored insulin was extracted using acid ethanol method and amounts of insulin determined by RIA on days 1, 2, 3, 5, 8, and 10. MIN-6 cells were significantly affected by the cytokine treatment at day 2 (P<0.05) in contrast to this Huh7ins and Melligen cells retained their ability to store insulin over the entire 10 days without significant difference between the treated and untreated cells (P>0.05).

Figure 26:
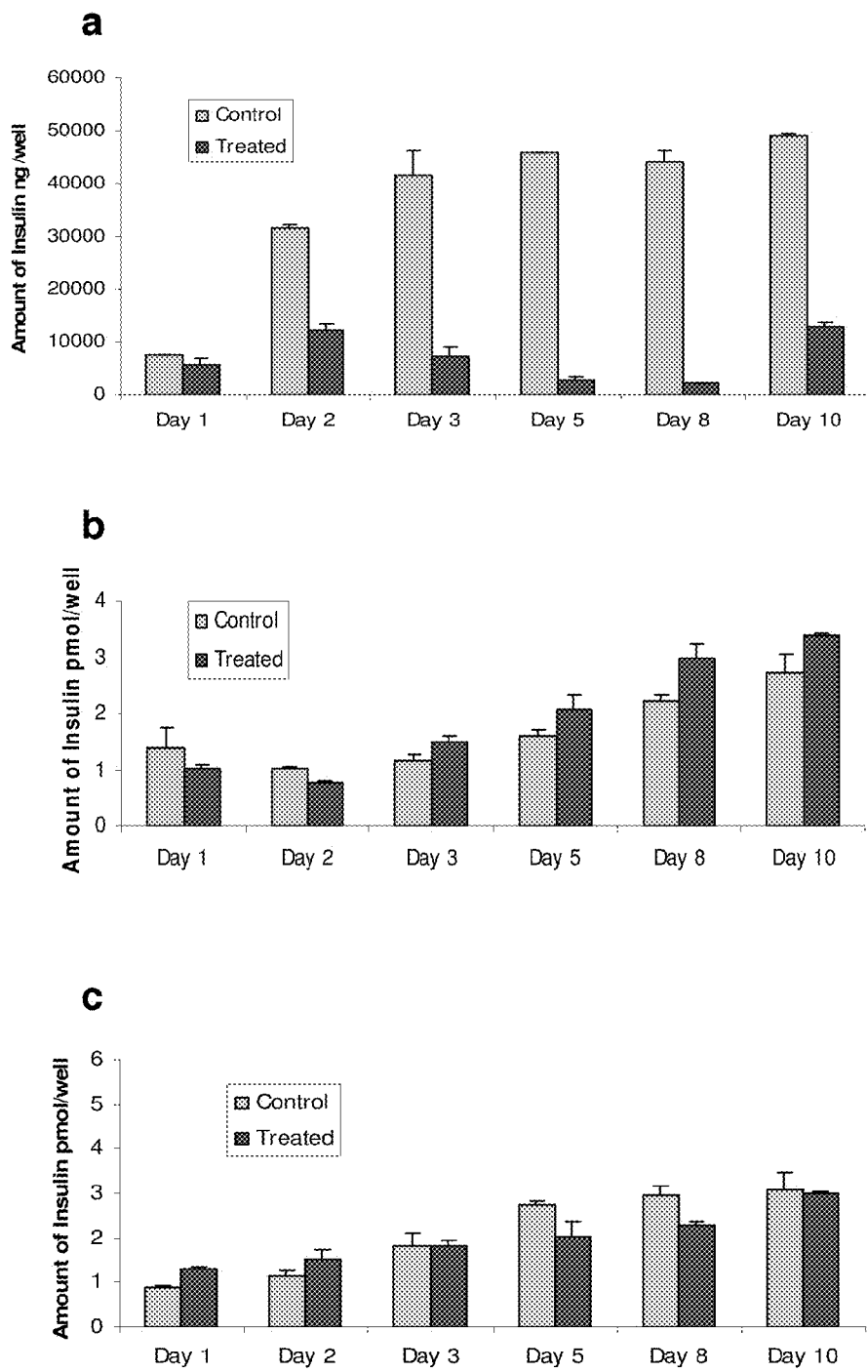
FIG. 26 is a graphical representation showing insulin storage in a) MIN-6 cells b) Huh7ins cells and c) Melligen cells after incubation with and without the cytokine mixture IFN-γ, TNF-α and IL-1β for 1, 2, 3, 5, 8 and 10 days. Results are expressed as mean±SE (n=5).

From FIG. 26a it can be seen that insulin storage per well steadily increased in untreated MIN-6 cells over the 10 days of the experiment as the cells proliferated. After exposure of MIN-6 cells to the cytokine mixture over 10 days, insulin content was significantly diminished after day 1 compared to the control MIN-6 cells (P=0.017). The difference between the treated and untreated MIN-6 cells continued to be significant throughout the remaining days of the experiment. In contrast, Huh7ins and Melligen cells treated with the cytokine combination did not show a significant difference in insulin storage compared to the untreated Huh7ins and Melligen cells respectively.

Glucose Responsiveness

Figure 27:
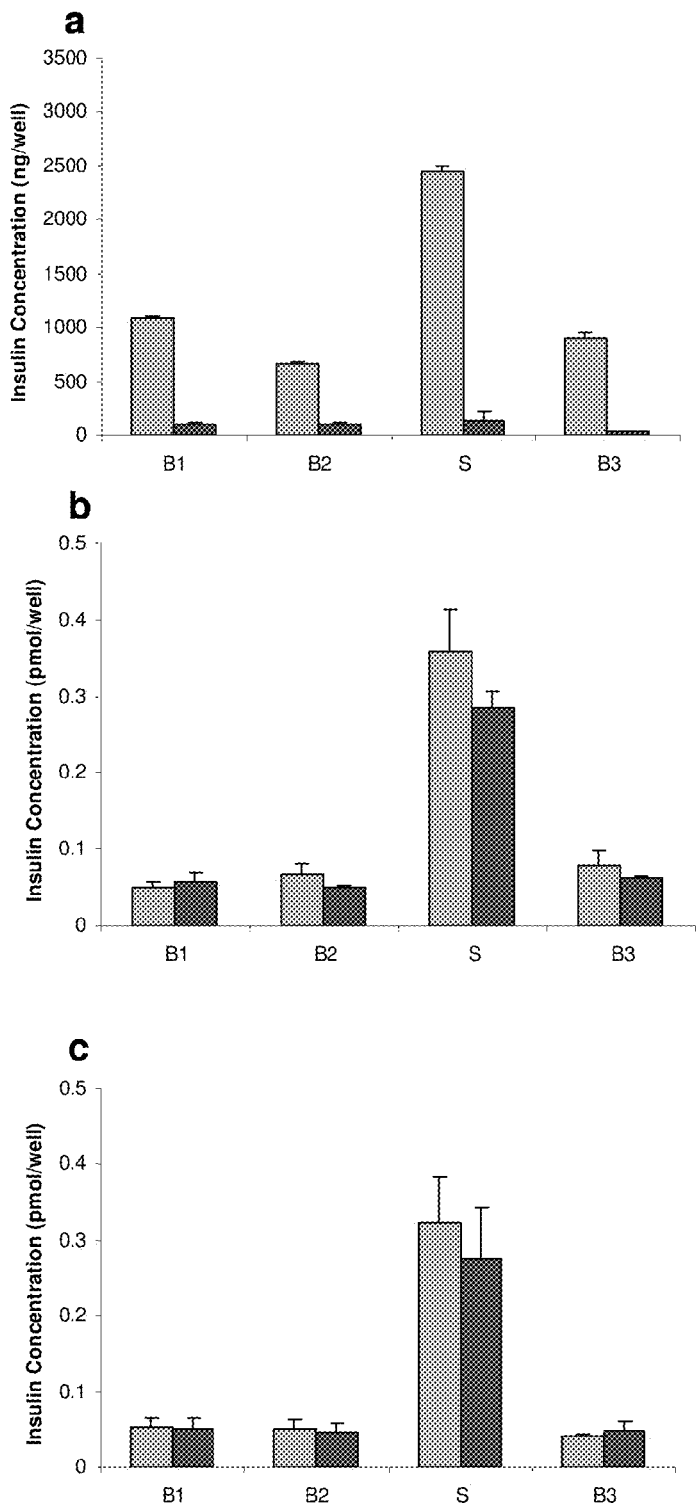
FIG. 27 is a graphical representation showing glucose responsiveness using a 20 mM glucose stimulus a) MIN-6 cells with and without treatment b) Huh7ins cells and c) Melligen cells after 10 days incubation with the cytokines IFN-γ (384 ng/mL), TNF-α (10 ng/mL) and IL-1β (2000 pg/mL). Results expressed as mean±SE (n=6). Untreated cells (mauve), treated cells (plum).

After 10 days of cytokine treatment of MIN-6 cells there was a significant decrease in insulin response to a glucose stimulus when compared to the control MIN-6 cells (P=0.0009). Insulin secretion of untreated MIN-6 cells in response to 20 mM glucose increased more than 5-fold over 1 h when compared to basal levels (692±78 ng/well/h) (P=0.0002) (FIG. 27a). The treated MIN-6 cells did not release significantly higher levels of insulin to the glucose stimulus compared to basal levels (P=0.60) (FIG. 27a). This was because the cells exhibited reduced viability after 10 days of co-incubation with cytokines, whereas control cells continued in log growth. Therefore, at day 10 there were more control cells and hence greater insulin storage. This data showed that the control cells responded to the 20 mM glucose stimulus, confirming that MIN-6 cells constituted an appropriate β-cell model.

The effect of the cytokines on glucose-responsiveness was also determined for the Huh7ins and Melligen cells. Untreated Huh7ins and Melligen cells gave a 5-fold increase in insulin secretion when stimulated with 20 mM glucose, with return to basal levels of insulin secretion (0.13±0.014 pmol/well/h) upon removal of the glucose stimulus (FIGS. 27b and c). Huh7ins and Melligen cells incubated with cytokines for 10 days showed a 4.5-fold increase in insulin secretion upon the 20 mM glucose stimulus and a return to basal levels of secretion (0.06±0.006 pmol/well/h) within 1 h after stimulation (FIGS. 27b and c). The amount of insulin secreted by the treated Huh7ins and Melligen cells during the stimulus was not significantly different to the result obtained for the untreated Huh7ins and Melligen cells respectively. This indicates that Huh7ins and Melligen cells retain the ability to respond to a glucose stimulus even after 10 days of cytokine treatment.

Figure 28:
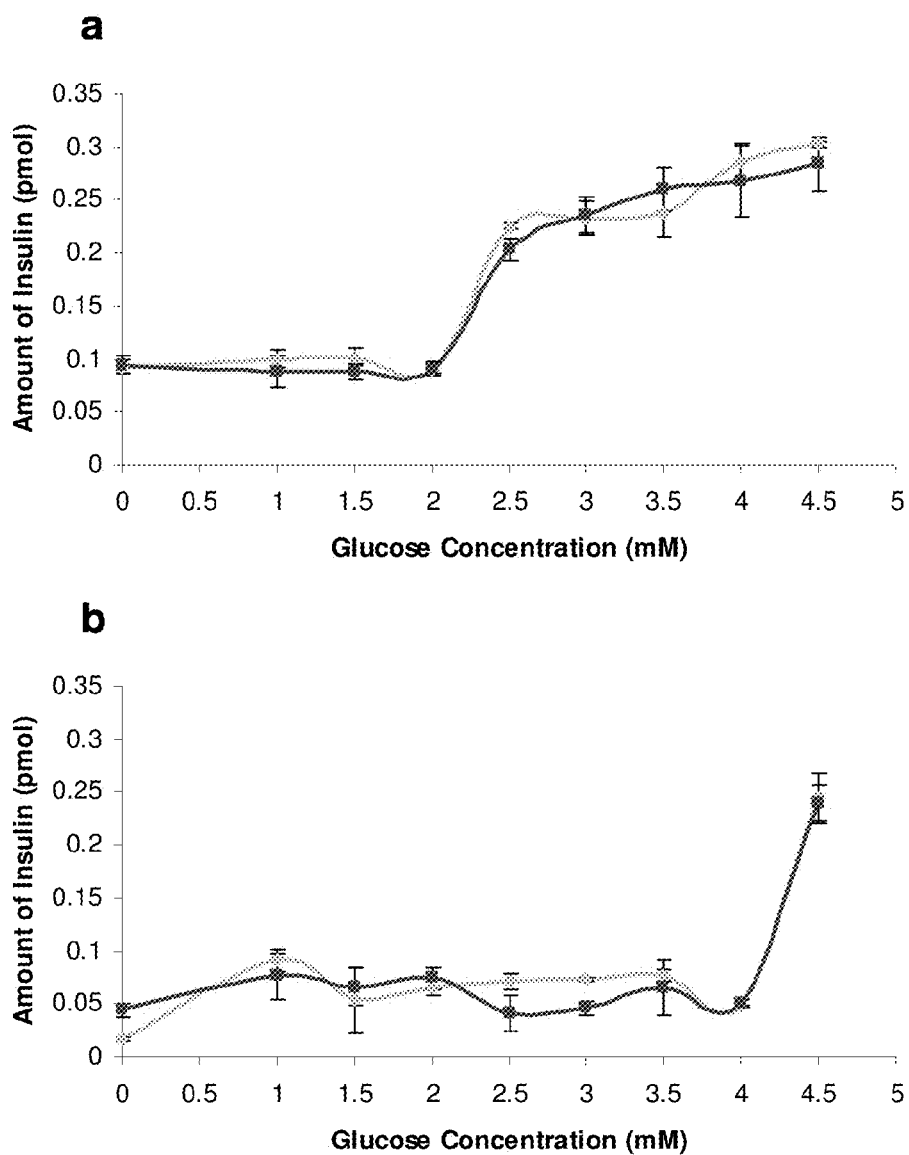
FIG. 28 is a graphical representation showing a 10-day cytokine treatment did not affect (a) Huh7ins and (b) Melligen cell's responsiveness to glucose in the millimolar range. Melligen cells secrete insulin in response to 4.25 mM glucose (the physiological range) and Huh7ins cells to 2.5 mM glucose.

Huh7ins and Melligen cells were cultured for 10 days with and without cytokines. At day 10, the cells were stimulated with increasing concentrations of glucose in basal medium. Huh7ins cells secreted increased amounts of insulin in response to 2.5 mM glucose and Melligen cells at 4.25 mM glucose. In both cell lines there was no significant difference observed between cytokine treated and untreated cells at any glucose concentration ($P>0.05$) (FIG. 28).

Example 5

Analysis of Expression of β-Cell Transcription Factors in Melligen Cells

Figure 29:
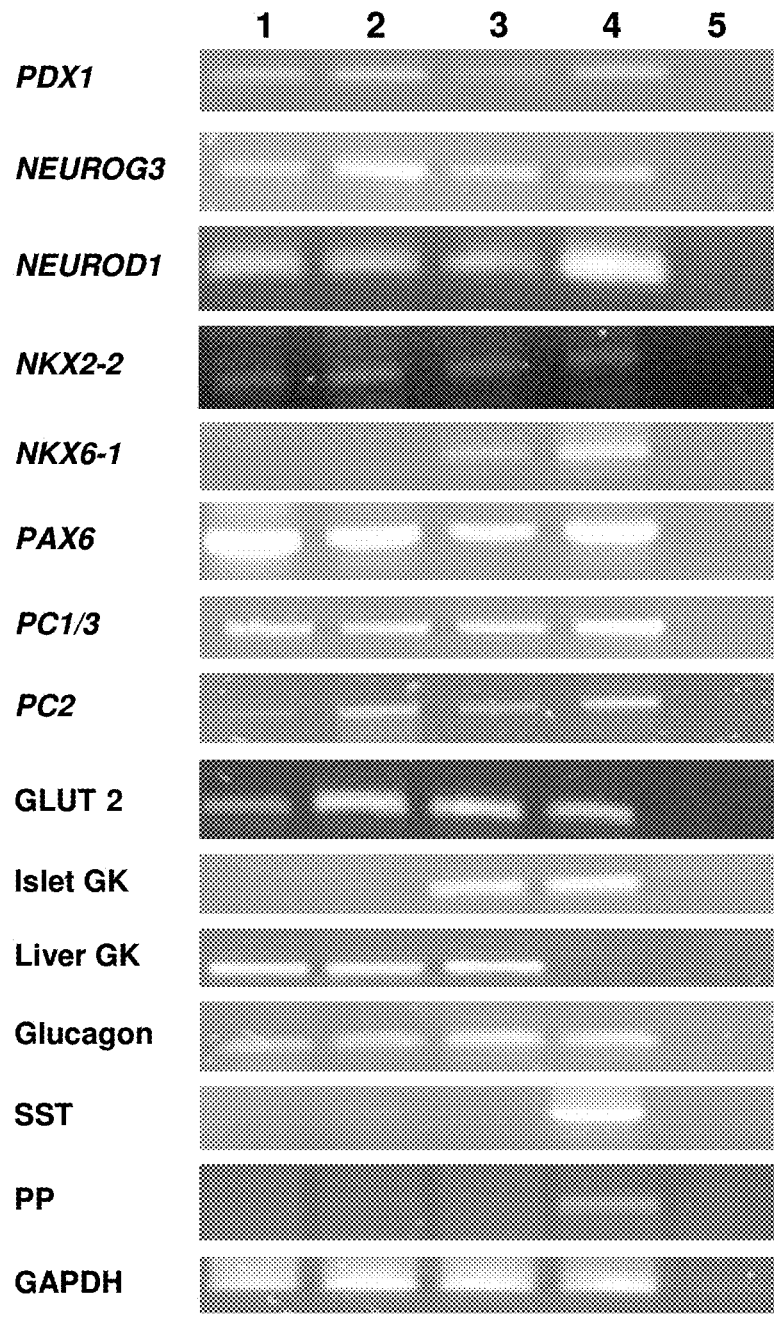
FIG. 29 is an image of β-cell transcription factors, pancreatic hormones, proinsulin convertase, and factors of the glucose sensing apparatus expressed in transfected liver cell lines. RT-PCR analysis for β-cell transcription factors [PDX-1, NEUROG3, NEUROD1, NKX2-2, NKX6-1, Pax6]; pancreatic hormones [glucagon, somatostatin (SST) and pancreatic polypeptide (PP)]; GLUT2 and Glucokinase (GK) [islet and liver form]; proinsulin convertases [PC1/3 and PC2] in Huh7 cells (lane 1), Huh7ins cells (lane 2), Melligen cells (lane 3), human islet (lane 4, the positive control), and water (lane 5, the negative control).

In this study, the level of pancreatic transdifferentiation that has occurred in Huh7ins and Melligen cells was detected. The expression of selected β-cell transcription factors, pancreatic hormones, and components of the glucose sensing apparatus [(GLUT2 and glucokinase (GK)] of pancreatic cells in the Huh7ins and Melligen cells together with the parent cell line Huh7 was analysed (FIG. 29).

Methods

RT-PCR

The RNA obtained from the cell lines was used to reverse transcribe complimentary DNA (cDNA) by using the reverse transcription reagents (Promega, U.S.A), which were made up to a 40 μL reaction mixture, containing RT buffer, Random primers, RNase inhibitor, dNTP mixture, Reverse transcriptase, RNase-free $dH_2O$. The volume for each reagent is listed in Table 2. All reagents were spun down to mix and incubated at 37° C. for 1 hour; this was followed by a 99° C. heat shock for 1 minute. The tubes were immediately transferred to ice and were ready to use for further amplification.

TABLE 2

| CONTENTS OF REVERSE TRANSCRIPTION MIXTURE | |
|---|---|
| Reagents | Volume (uL) |
| 5x AMP RT Buffer | 8 |
| Random Primers (500 μg/mL) | 3 |
| RNase Inhibitor (40 units/uL reaction) | 1 |
| dNTP mixture (10 mM) | 4 |
| Reverse Transcriptase (10 units) | 1.5 |
| Template RNA | 3 |
| RNase-free $dH_2O$ | 19.5 |
| Total Volume | 40 |

The possibility of cDNA contamination in total isolated RNA was excluded, due to the addition of 1.5 μL of DNase (1 unit/μL) to 60 μL of mRNA preparation. The sample was also examined following electrophoresis in a 1.5% agarose gel.

Specific final primer sequences are listed in Table 3, including: PDX1, NEUROG3, NEUROD1, NKX2-2, NKX6-1, PAX6, PC1/3, PC2, liver GK, islet GK, GLUT2, glucagon, somatostatin (SST), and pancreatic polypeptide (PP). These primers were diluted to 1 μg/μL, and further diluted 1:8 for PCR reactions.

TABLE 3

LIST OF GENE-SPECIFIC PRIMERS: THE SEQUENCES, THE SIZES OF PRODUCTS, AND ANNEALING TEMPERATURE.

| Gene | Forward | Reverse | Annealing temp.(° C.) | References |
|---|---|---|---|---|
| PDX-1 * (262 bp) | 5'CCCATGGATGAAGT CTACC3' (SEQ ID NO: 6) | 5'GTCCTCCTCCTTTTT CCAC3' (SEQ ID NO: 7) | 60 | Street et al., 2004 |
| Ngn3 (286 bp) | 5'AGACGACGCGAAGC TCACC3' (SEQ ID NO: 8) | 5'AAGCCAGACTGCCT GGGCT3' (SEQ ID NO: 9) | 69 | Heremans et al., 2002 |
| NeuroD (139 bp) | 5'TCACTGCTCAGGAC CTACTAA3' (SEQ ID NO: 10) | 5'CTCCTCGTCCTGAGA ACTG3' (SEQ ID NO: 11) | 53 | Westernman et al., 2004 |
| Nkx2.2 (329 bp) | 5'TGCAGCACATGCAG TACAACG3' (SEQ ID NO: 12) | 5'TCCCAAGGTTCAGA AGGAGAGG3' (SEQ ID NO: 13) | 56 | Heremans et al., 2002 |
| Nkx6.1 (284 bp) | 5'TCTTCTGGCCCGGGG TGATG3' (SEQ ID NO: 14) | 5'AGCCGCGTGCTTCTT CCTCC3' (SEQ ID NO: 15) | 58 | Heremans et al., 2002 |

TABLE 3-continued

LIST OF GENE-SPECIFIC PRIMERS: THE SEQUENCES, THE SIZES OF PRODUCTS, AND ANNEALING TEMPERATURE.

| Gene | Forward | Reverse | Annealing temp.(° C.) | References |
|---|---|---|---|---|
| Pax6 (301 bp) | 5'CAAAAGTCCAAGTG CTGGACAA3' (SEQ ID NO: 16) | 5'CCCATCTGTTGCTTT TCGCT3' (SEQ ID NO: 17) | 56.1 | Heremans et al., 2002 |
| PC 1/3 (404 bp) | 5'CTCCTAAAAGACTT GCGGAATCAC3' (SEQ ID NO: 18) | 5'TCCACACAGGCACT AAGAAAGACTG3' (SEQ ID NO: 19) | 51.9 | Zalzman et al., 2005 |
| PC 2 (572 bp) | 5'GCGGGATTACCAGT CCAAGTTG3' (SEQ ID NO: 20) | 5'TGTGCTTTCAGAGAT GTGGCG3' (SEQ ID NO: 21) | 55.3 | Zalzman et al., 2005 |
| GLUT2 (180 bp) | 5'TTGGTGTGATCAAT GCACCT3' (SEQ ID NO: 22) | 5'GCCACAGTCTCTTCC TCAGC3' (SEQ ID NO: 23) | 56 | Designed |
| Liver GK (186 bp) | 5'CTGCCTCCCAAAGC ATCTAC3' (SEQ ID NO: 24) | 5'GATCTTGGTCTGGG CATGTT3' (SEQ ID NO: 25) | 58 | Designed |
| Islet GK (176 bp) | 5'TCAGAAGCCTACTG GGGAAG3' (SEQ ID NO: 26) | 5'CTTCTGCATCCGTCT CATCA3' (SEQ ID NO: 27) | 68 | Designed |
| Glucagon (22 1 bp) | 5'CCCAAGATTTTGTGC AGTGGTT3' (SEQ ID NO: 28) | 5'GCGGCCAAGTTCTT CAACAAT3' (SEQ ID NO: 29) | 56 | Heremans et al., 2002 |
| Somatostatin (348 bp) | 5'ATGCTGTCCTGCCGC CTCCAG3' (SEQ ID NO: 30) | 5'ACAGGATGTGAAAG TCTTCCA3' (SEQ ID NO: 31) | 61 | Monges et al., 1996 |
| Pancreatic polypeptide (267 bp) | 5'CAATGCCACACCAG AGCAGATG3' (SEQ ID NO: 32) | 5'TGGGAGCAGGGAGC AAGC3' (SEQ ID NO: 33) | 60 | Zalzman et al., 2005 |

Real Time PCR

Real-time PCR was performed to determine the level of expression of some factors that were detected by RT-PCR in different cell lines, and to evaluate the effect of the overexpression of human islet GK in Melligen cells (FIG. 30).

Quantitative real time PCR was performed by using a Prism 7500 (ABI). Platinum SYBR Green qPCR supermix-UDG kit (Invitrogen) was used as amplification reagents. The primers are listed in Table 3.

Amplification conditions included initiation 50° C. for 2 min and denatured at 96° C. for 10 min, followed by 40 cycles and each cycle included denaturation at 96° C. 35 seconds, annealing at 58° C. (for human islet glucokinase cDNA) or 66.5° C. (for liver glucokinase gene) 35 seconds and extension at 72° C. 35 seconds.

Relative quantitative analysis was performed according to the comparative $C_T$ value by using the arithmetic formula $2^-(\Delta\Delta Ct)$. The cDNA levels were normalized to house keeping gene (human GAPDH).

Western Blot

Western analysis was performed for PDX1 as previously described in Huh7, Huh7ins and Melligen cells using human PDX1 (rabbit anti human, 1:1000 dilution, Chemicon) and secondary antibody to rabbit (Upstate, USA).

Results

Human Islet and Liver Glucokinase Genes in Different Cell Types.

Level of Expression of Liver Glucokinase in Melligen and Huh7ins Cells

As liver GK has found to be endogenously expressed in all the liver-derived cell lines by RT-PCR, the difference in the level of expression was further determined by real-time PCR among the cell lines. There was a significantly ($p<0.0001$) higher expression in Melligen cells compared to the Huh7ins cells with empty vector (no islet GK) (FIG. 31a). No significant difference ($p=0.268$) in the expression of liver GK was seen in the Huh7ins cells with empty vector (carry no islet GK) compared to the Huh7ins cells (FIG. 31b). Relative quantitative analysis performed according to the comparative $C_T$ value by using the arithmetic formula $2^-(\Delta\Delta Ct)$, showed that Melligen cells liver glucokinase expression was 5.133-fold higher expression than that of Huh7ins cells with vector only.

Level of Expression for β-Cell Transcription Factor, PDX1

Figure 32:
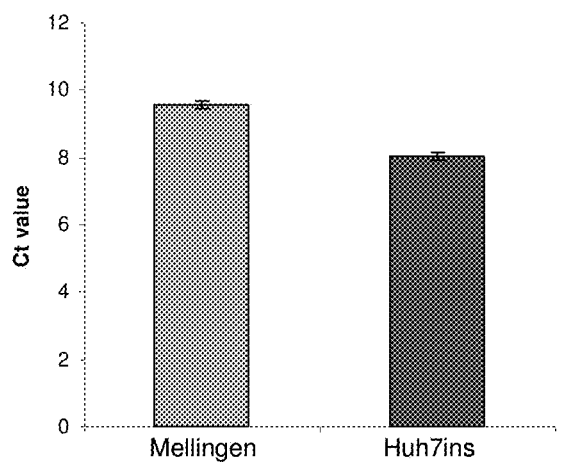
FIG. 32 is a graphical representation of real-time PCR expression of β-cell transcription factor, PDX-1: Melligen cells and Huh7ins cells. The level of gene expression was expressed as the corrected mean Ct value ±SE of individual cell lines (n=8).

While the expression of PDX-1 at the mRNA level was shown in the Huh7, Huh7ins, and Melligen cells by RT-PCR, real-time PCR analysis was performed to determine if any difference in the level of expression occurred among the cell lines. The paired t-test showed there was a significant difference ($p<0.0001$) in expression of PDX-1 in Melligen cells when compared to Huh7ins cells, Melligen cells had 2.908-fold higher expression than the Huh7ins cells according to the $C_T$ value (FIG. 32).

Figure 33:
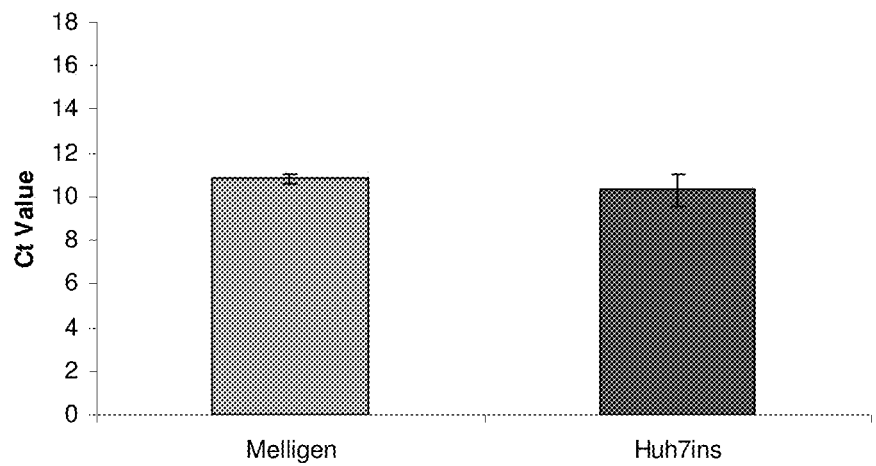
FIG. 33 is a graphical representation of real-time PCR expression of β-cell transcription factor, NEUROD1: in Melligen cells and Huh7ins cells. The level of gene expression was expressed as the corrected mean Ct value ±SE of individual cell lines (n=8).

Real-time PCR analysis indicated there was no significant difference in the expression of NEUROD, seen between Melligen cells and Huh7ins cells (FIG. 33).

Level of Expression for the Glucose Transporter, GLUT2

To determine whether overexpression of human insulin and human islet GK respectively in the Huh7ins and Melligen cells had any effect on GLUT2 expression at the mRNA level, real-time PCR experiments were performed on the cDNAs obtained from the Huh7, Huh7ins, and Melligen cells. FIG. 34 demonstrates that the level of expression for GLUT2 in Melligen cells was significantly (p<0.0001) higher compared to Huh7 and Huh7ins cells. There was no significant difference (p=0.013) in expression of GLUT2 between Huh7 and Huh7ins cells.

Western Analysis

Figure 35:
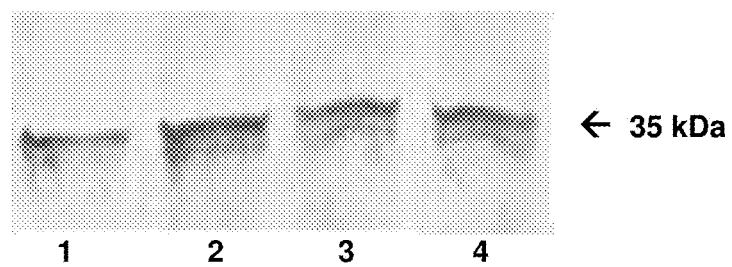
FIG. 35 is an image of qualitative western blot analysis for the expression of PDX-1 in: Huh7 (lane 1), Huh7ins (lane 2), Melligen (lane 3), and the positive control, human islet cells (lane 4).

The specific PDX-1 protein was revealed by western blotting analysis in Huh7, Huh7ins, and Melligen cells was detected at 35 kDa (FIG. 35).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Auricchio, A. et al., 2002, Constitutive and regulated expression of processed insulin following in vivo hepatic gene transfer, *Gene Therapy* 9: 963-71.

Bartlett, R. J. et al., 1998, Toward engineering skeletal muscle to release peptide hormone from the human preproinsulin gene, *Transplant Proc.* 30(2):451.

Beckman, J. A., Creager, M. A., and Libby, P. 2002. Diabetes and atherosclerosis: epidemiology, pathophysiology, and management. *JAMA* 287:2570-2581.

Ber, I. et al., 2003, Functional, persistent, and extended liver to pancreas transdifferentiation. *Journal of Biological Chemistry* 278: 31950-31957.

Bochan, M. R. et al., 1998, Stable transduction of human pancreatic adenocarcinoma cells, rat fibroblasts, and bone marrow-derived stem cells with recombinant adeno-associated virus containing the rat preproinsulin II gene, *Transplant Proc.* 30(2):453-4.

Cardozo, A. K. et al., 2001, A comprehensive analysis of cytokine-induced and nuclear factor-kappa B-dependent genes in primary rat pancreatic beta-cells, *J Biol Chem.* 276(52):48879-86.

Cheung, A. T. et al., 2000, Glucose-dependent insulin release from genetically engineered K cells, *Science* 290 (5498):1959-62.

de la Luna, S., et al., 1988, *Gene* 62:121-128.

Efrat S., 2004, Regulation of insulin secretion: insights from engineered beta-cell lines, *Ann NY Acad Sci.* 1014:88-96. Review.

Falqui, L. et al., 1999, Reversal of diabetes in mice by implantation of human fibroblasts genetically engineered to release mature human insulin, *Human Gene Therapy* 10 (11):1741-1742.

Falqui, L. et al., 1999, Reversal of diabetes in mice by implantation of human fibroblasts genetically engineered to release mature human insulin, *Hum Gene Ther.* 10(11): 1753-62.

Ferber, S. et al., 2000, Pancreatic and duodenal homeobox gene 1 induces expression of insulin genes in liver and ameliorates streptozotocin-induced hyperglycaemia, *Natural Medicine* 6(5):568-572.

Hathout, E. et al., 2003, Islet transplant: an option for childhood diabetes?, *Arch Dis Child.* 88(7):591-4. Review.

Heremans, Y. et al., 2002, Recapitulation of embryonic neuroendocrine differentiation in adult human pancreatic duct cells expression neurogenin 3, *The Journal of Cell Biology* 159(2):303-311.

Huang, M. T. F. and Gorman, C. M., 1990, *Nucleic Acids Res.* 18:937-947

Hughes, S. D. et al., 1992, Engineering of glucose-stimulated insulin secretion and biosynthesis in non-islet cells, *Proc Natl Acad Sci USA*. 89(2):688-92.

Imai, J. et al., 2004, Constitutively active PDX1 induced efficient insulin production in adult murine liver, *Biochemical and Biophysical Research Communications* 326:402-409.

Jackson, R. J. et al., 1990, *Trends Biochem. Sci.* 15:477-483

Janeesens and Tschopp, 2006, Signals from within: the DNA-damage-induced NF-κB response, *Cell Death and Differentiation*, Review, 13: 773-784.

Jang, S. K. et al., 1988, *J. Virol.* 62:2636-2643

Karasik, A. et al., 2005, Cell-replacement therapy for diabetes: Generating functional insulin-producing tissue from adult human liver cells, *PNAS* 102 (22):7964-7969.

Kasten-Jolly, J. et al., 1997, Reversal of hyperglycaemia in diabetic NOD mice by human proinsulin gene therapy, *Transplantation Proceedings* 29: 2216-2218.

Kim and Park, 2001, Modulated insulin delivery from glucose-sensitive hydrogel dosage forms, *J Control Release* 77(1-2):39-47.

Kojima, H. et al., 2003, NeuroD-betacellulin gene therapy induces islet neogenesis in the liver and reverse diabetes in mice, *Nature Medicine* 9(5): 596-603.

Kolodka, T. M. et al., 1995, Gene therapy for diabetes mellitus in rats by hepatic expression of insulin, *Proceedings of the National Academy of Sciences of the United States of America* 92: 3293-3297.

Kutlu, B. et al., 2003, Molecular regulation of monocyte chemoattractant protein-1 expression in pancreatic beta-cells, *Diabetes* 52(2):348-55.

Kuwajima, M. et al. 1996. The glucose phosphorylating capacity of liver as measured by three independent assays: implication for the mechanism of hepatic glycogen synthesis. *J Biol. Chem.* 261: 8849-53.

Levine and Leibowitz, 1999, Towards gene therapy of diabetes mellitus, *Mol Med Today* 5(4):165-71. Review.

Lipes, M. A. et al., 1996, Insulin-secreting non-islet cells are resistant to autoimmune destruction, *Proc Natl Acad Sci USA*. 93(16):8595-600.

Mandrup-Poulsen T., 2001, beta-cell apoptosis: stimuli and signalling, *Diabetes* 50 Suppl 1:S58-63. Review.

McAlister, V. C. et al., 2000, Sirolimus-tacrolimus combination immunosuppression, *Lancet.* 355:376-377.

Monges, G. et al., 1996, Gastrointestinal hormone mRNA expression in human colonic adenocarcinomas, hepatic metastases and cell lines, *J Clin Pathol: Mol Pathol.* 49:Mi 59-Mi65.

Nakayama, M. et al., 2005, Prime role for an insulin epitope in the development of type 1 diabetes in NOD mice, *Nature* 435(7039):220-3.

Ortis, F. et al., 2006, Cytokine-induced proapoptotic gene expression in insulin-producing cells is related to rapid, sustained, and nonoscillatory nuclear factor-kappaB activation, *Mol Endocrinol.* 20(8): 1867-79.

Permutt, M A et al., 1989, Cloning and functional expression of a human pancreatic islet glucose-transporter, *Proc Natl Acad Sci USA,* 86:8688-8692

Pinkse, G. G. et al., 2005, Autoreactive CD8 T cells associated with beta cell destruction in type 1 diabetes, *Proc Natl Acad Sci USA*. 102(51):18425-30.

Rees, S. et al., 1996, *BioTechniques* 20:102-104

Sapir, T. et al., 2005, Cell-replacement therapy for diabetes: Generating functional insulin-producing tissue from adult human liver cells. *PNAS* 102 (22):7964-7969.

Seewaldt, S. et al., 2000, Virus-induced autoimmune diabetes: most beta-cells die through inflammatory cytokines and not perforin from autoreactive (anti-viral) cytotoxic T-lymphocytes, *Diabetes* 49(11): 1801-9.

Selden, R. F. et al., 1987, Regulation of insulin-gene expression. Implication for gene therapy, *The New England Journal of Medicine* 317 (17): 1067-1076.

Simpson, A. M. et al., 1993, Transformation of pituitary and fibroblast cell lines using human insulin cDNA and a dexamethasone-inducible promoter, *Transplantation Proceedings* 25:2915-2916.

Tabiin, M. T. et al., 2001, Susceptibility of insulin-secreting hepatocytes to the toxicity of pro-inflammatory cytokines, *J Autoimmun.* 17(3):229-42.

Taniguchi, H. et al., 1997, Constant delivery of proinsulin by encapsulation of transfected cells, *J Surg Res.* 70(1):41-5.

Truong, W. et al., 2005, Clinical islet transplantation at the University of Alberta—the Edmonton experience, *Clin Transpl.* 153-72.

Tuch, B. E. et al., 2003, Function of a genetically modified human liver cell line that stores, processes and secretes insulin, *Gene Ther.* 10(6):490-503.

Verge, C. F. et al., 1996, Prediction of type I diabetes in first-degree relatives using a combination of insulin, GAD, and ICA512bdc/IA-2 autoantibodies, *Diabetes* 45(7):926-33.

Vermes, I. et al., 1995, A novel assay for apoptosis. Flow cytometric detection of phosphatidylserine expression on early apoptotic cells using fluorescein labelled Annexin V, *J Immunol Methods* 184(1):39-51.

Vollenweider, F. et al., 1992, Processing of proinsulin by transfected hapatoma (FAO) cells, *Journal of Biological Chemistry* 267:14629-14623.

Westerman, B. A. et al., 2004, NEUROD1 acts in vitro as an upstream regulator of NEUROD2 in trophoblast cells, *Biochimica et Biophysica Acta* 1676: 96-103.

Wilson, J. E. 1984. Regulation of mammalian hexokinase activity. In: *Regulation of carbohydrate metabolism*. Beitner R ed. Boca Raton, Fla., CRC Press. P. 45-85.

Wong, R. Y. L. et al., 1999, Expression of human insulin in haematopoietic mononuclear cells: potential gene therapy for type I diabetes, *7th World Congress of the International Pancreas and Islet Transplant Association, Sydney* 7: 122.

Zalzman, M. et al., 2003, Reversal of hyperglycemia in mice by using human expandable insulin-producing cells differentiated from fetal liver progenitor cells, *PNAS* 100 (12):7253-7258.

---

The invention claimed is:

1. An isolated genetically modified mammalian hepatocyte comprising a nucleic acid molecule encoding a human pancreatic islet glucokinase, wherein said genetically modified mammalian hepatocyte produces insulin in response to extracellular glucose levels that are equivalent to physiological glucose levels in the range of 3-8 mM.

2. The isolated genetically modified hepatocyte of claim 1, wherein the isolated genetically modified mammalian hepatocyte produces insulin in response to extracellular glucose levels in the range of 3.5-7 mM.

3. The isolated genetically modified hepatocyte of claim 1, wherein the isolated genetically modified mammalian hepatocyte produces insulin in response to extracellular glucose levels in the range of 4-6 mM.

4. The isolated genetically modified hepatocyte of claim 1, wherein the isolated genetically modified mammalian hepatocyte produces insulin in response to extracellular glucose levels in the range of 4-5 mM.

* * * * *